United States Patent
Biber et al.

(10) Patent No.: US 11,337,973 B2
(45) Date of Patent: May 24, 2022

(54) SUBSTITUTED [1,2,4]TRIAZOLO[4,3-A]PYRAZINES AS PROLYL ENDOPEPTIDASE INHIBITORS

(71) Applicants: Bayer Aktiengesellschaft, Leverkusen (DE); Bayer Pharma Aktiengesellschaft, Berlin (DE)

(72) Inventors: Nicole Biber, Wuppertal (DE); Damian Brockschnieder, Haan (DE); Florian Kölling, Wuppertal (DE); Jörg Meding, Wuppertal (DE); Hideki Miyatake Ondozabal, Berlin (DE); Thomas Neubauer, Wuppertal (DE); Martina Schäfer, Berlin (DE); Dmitry Zubov, Remscheid (DE); Carsten Terjung, Bochum (DE)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/761,713

(22) PCT Filed: Oct. 31, 2018

(86) PCT No.: PCT/EP2018/079851
§ 371 (c)(1),
(2) Date: May 5, 2020

(87) PCT Pub. No.: WO2019/091847
PCT Pub. Date: May 16, 2019

(65) Prior Publication Data
US 2020/0375986 A1 Dec. 3, 2020

(30) Foreign Application Priority Data

Nov. 7, 2017 (EP) .................... 17200382.4

(51) Int. Cl.
*A61K 31/4985* (2006.01)
*C07D 487/04* (2006.01)
*A61P 11/00* (2006.01)
*A61K 45/06* (2006.01)

(52) U.S. Cl.
CPC .......... *A61K 31/4985* (2013.01); *A61K 45/06* (2013.01); *A61P 11/00* (2018.01); *C07D 487/04* (2013.01)

(58) Field of Classification Search
CPC .................... A61K 31/4985; C07D 487/04

USPC .......................................... 514/249; 544/350
See application file for complete search history.

(56) References Cited

U.S. PATENT DOCUMENTS 10,722,501 B2   7/2020   Biber et al.

FOREIGN PATENT DOCUMENTS

WO   WO-2019091847 A1 *   5/2019   ........... C07D 487/04

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Haffner, C.D. et al. (2008). "Pyrrolidinyl pyridone and pyrazinone analogues as potent inhibitors of prolyl oligopeptidase POP)," Bioorganic & Midicinal Chemistry Letter, 18: 4360-4363.
International Search Report dated Dec. 19, 2018, for PCT Patent Application No. PCT/EP2018/079851 filed on Oct. 31, 2018, three pages.
Mariaule, G. et al. (2016). "3-Oxo-hexahydro-1H-isoindole-4-carboxylic Acid as a Drug Chiral Bicyclic Scaffold Structure-Based Design and Preparation of Conformationally Constrained Covalent and Noncovalent Prolyl Oligopeptidase Inhibitors," Journal of Medicinal Chemistry, 59:4221-4234.
U.S. Appl. No. 16/897,059, filed Jun. 9, 2020, for Biber et al. (U.S. Patent Application is not submitted herewith pursuant to the waiver of 37 C.F.R. § 1.98(a)(2)(iii) issued by the Office on Sep. 21, 2004.).

* cited by examiner

*Primary Examiner* — Douglas M Willis
(74) *Attorney, Agent, or Firm* — Morrison & Foerster LLP

(57) ABSTRACT

The invention relates to prolyl endopeptidase (PREP) inhibitors of formula (I) which contain a condensed 2,4-dihydro-3H-1,2,4-triazol-3-one ring system, methods for producing same, the use thereof alone or in combinations for treating and/or preventing diseases, and the use thereof for producing drugs for treating and/or preventing diseases, in particular for treating and/or preventing inflammatory lung diseases (COPD).

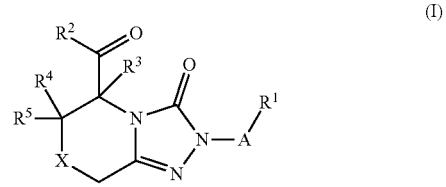

31 Claims, No Drawings

SUBSTITUTED [1,2,4]TRIAZOLO[4,3-A]PYRAZINES AS PROLYL ENDOPEPTIDASE INHIBITORS

CROSS REFERENCE TO RELATED APPLICATIONS

This application is a national stage application under 35 U.S.C. § 371 of International Application No. PCT/EP2018/079851, filed internationally on Oct. 31, 2018, which claims the benefit of European Application No. 17200382.4, filed Nov. 7, 2017.

BACKGROUND OF THE INVENTION

The present application relates to novel substituted 2,4-dihydro-3H-1,2,4-triazol-3-ones, to processes for preparation thereof, to the use thereof, alone or in combinations, for treatment and/or prophylaxis of diseases, and to use thereof for production of medicaments for treatment and/or prophylaxis of diseases, especially for treatment and/or prophylaxis of pulmonary inflammation disorders.

The enzyme prolyl endopeptidase (PREP, prolyl oligopetidase, PE, POP) is a serine protease which cleaves peptides up to a length of 30 amino acids beyond the amino acid proline [Moriyama et al., J. Biochem. 1988, 104:112-117]. PREP is expressed and secreted constitutively in all organs and tissue, by cells including leukocytes and epithelial cells. Release is increased on contact with irritant, inflammatory substances [Szul et al., Am. J. Respir. Cell Mol. Biol. 2016, 54:359-369]. While PREP in the central nervous system is involved in the degradation of peptidic neurotransmitters, PREP in the entire periphery, including in the lung, is an enzyme which cleaves degradation products of collagen inter alia in degenerative and inflammatory processes. Because of the high content of proline and glycine in the amino acid sequence of collagen, tripeptides having the sequence proline-glycine-proline (PGP) are formed therein by the degradation of the collagen fragments [Weathington et al., Nat. Med. 2006, 12:317-323]. Significantly elevated PGP concentrations have been described in sputum from patients having chronic pulmonary inflammation disorders, such as chronic obstructive pulmonary disease (COPD) or cystic fibrosis (mucoviscidosis, CF) [O'Reilly et al., Respir. Res. 2009, 10:38 doi:10.1186/1465-9921-10-38; Gaggar et al., J. Immunol. 2008, 180:5662-5669]. PGP, which is produced by PREP, is a chemokine for neutrophil granulocytes (neutrophils for short), meaning that PGP leads to migration of neutrophils into tissue having elevated PGP concentrations. There are pointers that the mechanism of this attraction of neutrophils is based on direct stimulation of the neutrophils via PGP-sensitive receptors on the neutrophil cell membrane (e.g. CXCR1, CXCR2) or is brought about indirectly through the release of further chemokines, for example interleukins (e.g. interleukin-8, CXCL8), by other cell types (e.g. macrophages, epithelial cells). The chemokine effect of PGP on neutrophils has been repeatedly demonstrated in vitro and in vivo [Weathington et al., Nat. Med. 2006, 12:317-323; De Kruijf et al., Eur. J. Pharmacol. 2010, 643:29-33; Overbeek et al., Eur. J. Pharmacol. 2011, 668:428-434; Braber et al., Eur. J. Pharmacol. 2011, 668:443-449]. In an animal experiment, the effect of PGP has been eliminated by the addition of a complementary tripeptide (threonine-arginine-threonine, RTR) and by the administration of a CXCR2 receptor blocker. It has been shown that repeated application of PGP to the lungs of mice can trigger lung emphysema. In addition, cigarette smoke increases the PGP concentration in the lungs of mice exposed to cigarette smoke. The simultaneous administration of PGP-neutralizing RTR can eliminate the abovementioned cigarette smoke-induced effects [Braber et al., Eur J. Pharmacol. 2011, 668:443-449; Braber et al., Am. J. Physiol. Lung Cell Mol. Pysiol. 2011, 300:L255-L265].

Chronic obstructive pulmonary disease (COPD) is a lung disease associated with chronic bronchitis, breathlessness, coughing and expectoration, and with the decline of lung tissue (emphysema). Lung function is increasingly restricted owing to the obstructive change in the bronchia and as a result of the loss of functional lung tissue as the disorder progresses. Hyperinflation of the lung is a common consequence of the hindered exhalation.

The most common cause of the occurrence of COPD is chronic inhalation of cigarette smoke. In addition, on a global scale, with regional differences, 10% to 40% of patients develop COPD which is not attributable to cigarette smoke but probably to exposure to environmental poisons, for example smoke from coal or wood fires or diesel exhaust gases [Salvi, Clin. Chest Med. 2014, 35:17-27].

At present, only treatment of the symptoms of COPD is possible. COPD patients primarily receive bronchia-widening medicaments which make it easier to breathe. The use of inflammation-inhibiting medicaments has been limited to date.

As well as the chronic symptoms described, COPD patients frequently suffer from acute onset of time-limited deteriorations in their state of health, which is impaired in any case, and these necessitate additional treatment [Ewig, Klinikarzt 2013, 42:182-187]. The treatment of these disease episodes, referred to as acute exacerbations, has to date been restricted to the administration of oxygen and systemically administered corticosteroids.

In a clinical COPD study, it was shown that roflumilast (an anti-inflammatory PDE4 inhibitor) leads to a decrease in the concentration of PGP in the sputum and serum of the COPD patients treated [Wells et al., Am. J. Respir. Crit. Care Med. 2015, 192:934-942].

Elevated pro-inflammatory PGP concentrations have additionally been described, inter alia, in shock lung (acute respiratory syndrome, ARDS) and in corneal injury to the eye [Hahn et al., Sci. Adv. 2015, 1: e1500175; Pfister et al., Invest. Ophthalmol. Vis. Sci. 1998, 39:1744-1750]. Here too, a pro-inflammatory effect of PGP is formulated, which leads firstly to elevated permeability of vessels, and secondly, as already described above, to increasing recruitment of neutrophils (neutrophilia) and hence to increased inflammation. Since the formation of PGP in inflammatory processes is directly linked to the destruction of tissue, and PGP in turn promotes the inflammation, the involvement of PGP in self-sustaining chronic inflammation processes is probable. Particular mention should be made here of COPD and acute exacerbations of COPD (AE-COPD), which are based on chronic inflammation [Russell et al., Curr Opin Pilm Med. 2016, 22:91-99; Anzueto, Eur. Respir. Rev. 2010, 19:113-118]. But there are also other chronic inflammation disorders and wound-healing disorders of the lung and other tissues and organs, for example of the skin, the eye, the blood vessels, connective tissue, the skeleton and the musculature, that could also profit from a reduction in the PGP concentration as a result of the PREP inhibition.

Potential fields of use for PREP inhibitors are acute and chronic pathological processes involving PREP or substrates and products of PREP. Since this anti-inflammatory effect of the PREP inhibitors probably does not intervene directly in the function of the immune system, and therefore possibly no immunosuppressive effect is to be expected, one advantage of PREP inhibition could be that fewer side effects could occur in this regard in treated patients than with conventional immunomodulatory principles of action. Since PGP is formed from collagen fragments by means of the PREP enzyme which is expressed constitutively, i.e. is constantly present, and PGP production is therefore not controlled or regulated by the immune system, it is to be expected that the anti-inflammatory effect will also occur in patients where efficacy with respect to corticosteroids is reduced, for instance due to resistances. Corticosteroid resistances are described, particularly in COPD patients, in stable phases outside acute exacerbations. Furthermore, an additive or synergistic efficacy of the combination with corticosteroids is also to be expected in the event that corticosteroids are fully effective, and in the event that their effect is restricted or greatly reduced. A combination with all other inflammatory mechanisms of action is likewise possible.

Since PGP, the formation of which is prevented by PREP inhibition, probably plays a leading role in the inflammation process in all disorders with inflammatory components and the involvement of collagen or fragments thereof, PREP inhibition can have positive effects on many disorders such as autoimmune disorders, chronic inflammation disorders such as rheumatoid disorders, infection events, degenerative processes (skin, organs, bones, musculature).

The problem addressed by the present invention was that of identifying and providing novel compounds of low molecular weight that act as potent inhibitors of the enzyme prolyl endopeptidase (PREP, prolyl oligopeptidase, PE, POP), and, in the event of acute or chronic, pathological or inflammatory-degenerative processes, via the reduction in PREP-dependent PGP production, particularly reduce the recruitment of neutrophil granulocytes in organs, especially in the lung.

The application WO2006052962A2 describes bicyclic triazoles for controlling disorders that occur via integrin inhibition. 1,2-Dihydro-3H-indazol-3-ones as NOX inhibitors for controlling diseases such as COPD, Alzheimer's, inflammatory or fibrotic disorders are known from WO2011062864A2.

DETAILED DESCRIPTION OF THE INVENTION

The present invention provides compounds of the general formula (I)

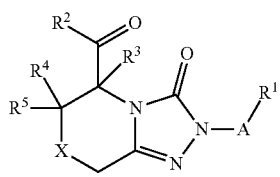

in which
A is $(C_1-C_4)$-alkylene or $CD_2$,
where $(C_1-C_4)$-alkylene may be substituted by hydroxyl and $(C_1-C_4)$-alkoxy and up to pentasubstituted by fluorine,
or
is a group of the formula

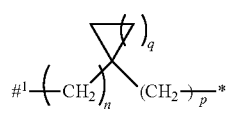

in which
n is 0 or 1,
p is 0 or 1,
q is 1 or 2, where
¹ marks the bond to the nitrogen atom of the 5-oxo-4,5-dihydro-1H-1,2,4-triazol-1-yl ring,
* marks the bond to $R^1$,
X is a group of the formula

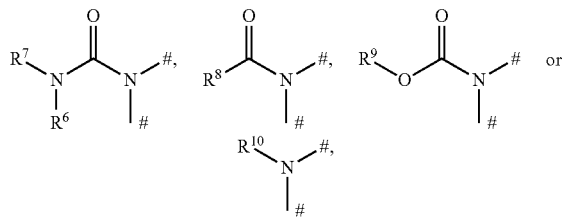

where
marks the bond to the respective carbon atom of the ring,
$R^6$ is $(C_1-C_6)$-alkyl, $(C_3-C_6)$-cycloalkyl, phenyl or 5- to 6-membered heteroaryl,
  in which $(C_1-C_6)$-alkyl may be substituted by hydroxyl, cyano or $(C_1-C_4)$-alkoxy or up to pentasubstituted by fluorine,
  in which $(C_3-C_6)$-cycloalkyl may be substituted by 1 to 3 substituents selected independently from the group of halogen, cyano, trifluoromethyl, $(C_1-C_4)$-alkyl and $(C_1-C_4)$-alkoxy,
  in which phenyl may be substituted by 1 to 3 substituents selected independently from the group of halogen, cyano, trifluoromethyl, $(C_1-C_4)$-alkyl and $(C_1-C_4)$-alkoxy,
  in which 5- to 6-membered heteroaryl may be substituted by 1 to 3 substituents selected independently from the group of halogen, cyano, trifluoromethyl, $(C_1-C_4)$-alkyl and $(C_1-C_4)$-alkoxy,
$R^7$ is hydrogen or $(C_1-C_4)$-alkyl,
  in which $(C_1-C_4)$-alkyl may be up to pentasubstituted by fluorine,
$R^8$ is $(C_1-C_4)$-alkyl, $(C_3-C_6)$-cycloalkyl, phenyl or 5- to 6-membered heteroaryl,
  in which $(C_1-C_4)$-alkyl may be substituted by hydroxyl, cyano or $(C_1-C_4)$-alkoxy or up to pentasubstituted by fluorine,
  in which $(C_3-C_6)$-cycloalkyl may be substituted by 1 to 3 substituents selected independently from the group of halogen, cyano, trifluoromethyl, $(C_1-C_4)$-alkyl and $(C_1-C_4)$-alkoxy,
  in which phenyl may be substituted by 1 to 3 substituents selected independently from the group of halogen, cyano, trifluoromethyl, $(C_1-C_4)$-alkyl and $(C_1-C_4)$-alkoxy,
  in which 5- to 6-membered heteroaryl may be substituted by 1 to 3 substituents selected independently from the group of halogen, cyano, trifluoromethyl, $(C_1-C_4)$-alkyl and $(C_1-C_4)$-alkoxy,
$R^9$ is $(C_1-C_4)$-alkyl, $(C_3-C_6)$-cycloalkyl or phenyl,
  in which $(C_1-C_4)$-alkyl may be up to pentasubstituted by fluorine,
  in which $(C_3-C_6)$-cycloalkyl may be substituted by 1 to 3 substituents selected independently from the group of halogen, cyano, trifluoromethyl, $(C_1-C_4)$-alkyl and $(C_1-C_4)$-alkoxy,
  in which phenyl may be substituted by 1 to 3 substituents selected independently from the group of halogen, cyano, trifluoromethyl, $(C_1-C_4)$-alkyl and $(C_1-C_4)$-alkoxy, $R^{10}$ is hydrogen, $(C_1-C_4)$-alkyl, $(C_3-C_6)$-cycloalkyl or phenyl,
  in which $(C_1-C_4)$-alkyl may be substituted by hydroxyl, cyano, $(C_1-C_4)$-alkoxy or $(C_3-C_6)$-cycloalkyl or up to pentasubstituted by fluorine,
    in which $(C_3-C_6)$-cycloalkyl may be up to tetrasubstituted by fluorine,
  in which $(C_3-C_6)$-cycloalkyl may be substituted by 1 to 3 substituents selected independently from the group of halogen, cyano, trifluoromethyl, $(C_1-C_4)$-alkyl and $(C_1-C_4)$-alkoxy,
  in which phenyl may be substituted by 1 to 3 substituents selected independently from the group of halogen, cyano, trifluoromethyl, $(C_1-C_4)$-alkyl and $(C_1-C_4)$-alkoxy,
  in which 5- to 6-membered heteroaryl may be substituted by 1 to 3 substituents selected independently from the group of halogen, cyano, trifluoromethyl, $(C_1-C_4)$-alkyl and $(C_1-C_4)$-alkoxy,
or
is oxygen,
$R^1$ is $(C_3-C_7)$-cycloalkyl, phenyl or 5- to 10-membered heteroaryl,
  where $(C_3-C_7)$-cycloalkyl may be substituted by 1 to 3 substituents selected independently from the group of halogen, cyano, trifluoromethyl, $(C_1-C_4)$-alkyl and $(C_1-C_4)$-alkoxy,
    in which $(C_1-C_4)$-alkyl may be up to pentasubstituted by fluorine,
  where phenyl is substituted by 1 to 4 substituents selected independently from the group of halogen, cyano, $(C_1-C_4)$-alkyl, $(C_3-C_6)$-cycloalkyl, trifluoromethyl, $(C_1-C_4)$-alkoxy, $(C_3-C_5)$-cycloalkoxy, monofluoromethoxy, difluoromethoxy, trifluoromethoxy, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_5)$-cycloalkylaminocarbonyl, $(C_1-C_4)$-alkylsulfanyl, $(C_1-C_4)$-alkylsulfonyl, $(C_1-C_4)$-alkylsulfonimidoyl, $(C_1-C_4)$-cycloalkylsulfonyl, aminosulfonyl, mono-$(C_1-C_4)$-alkylaminosulfonyl, di-$(C_1-C_4)$-alkylaminosulfonyl, $(C_1-C_4)$-alkylsulfinyl, amino, mono-$(C_1-C_4)$-alkylamino or di-$(C_1-C_4)$-alkylamino,
or
where 5- to 10-membered heteroaryl may be substituted by 1 to 4 substituents selected independently from the group of halogen, cyano, $(C_1-C_4)$-alkyl, $(C_3-C_6)$-cycloalkyl, trifluoromethyl, $(C_1-C_4)$-alkoxy, $(C_3-C_5)$-cycloalkoxy, difluoromethoxy, trifluoromethoxy, 2,2,2-trifluoroethoxy, phenyl, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_5)$-cycloalkylaminocarbonyl, $(C_1-C_4)$-alkylsulfanyl, $(C_1-C_4)$-alkylsulfonyl, $(C_1-C_4)$-alkylsulfonimidoyl, $(C_1-C_4)$-cycloalkylsulfonyl, aminosulfonyl, mono-$(C_1-C_4)$-alkylaminosulfonyl, di-$(C_1-C_4)$-alkylaminosulfonyl, $(C_1-C_4)$-alkylsulfinyl, amino, mono-$(C_1-C_4)$-alkylamino or di-$(C_1-C_4)$-alkylamino,
  in which phenyl may be substituted by methyl, ethyl, chlorine, fluorine or methoxy,
$R^2$ is a group of the formula

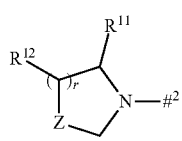

where
$\#^2$ marks the bond to the carbonyl carbon atom,
r is 0 or 1,
Z is O, $NR^{14}$, S, SO, $SO_2$ or $CR^{13A}R^{13B}$,
  in which
  $R^{13A}$ is hydrogen, halogen, cyano, $(C_1-C_4)$-alkyl, $(C_3-C_6)$-cycloalkyl, trifluoromethyl, difluoromethyl, fluoromethyl, hydroxyl, $(C_1-C_4)$-alkoxy, $(C_3-C_5)$-cycloalkoxy, difluoromethoxy, trifluoromethoxy or 2,2,2-trifluoroethoxy,
    in which $(C_1-C_4)$-alkyl may be substituted by hydroxyl, amino, mono-$(C_1-C_4)$-alkylamino or di-$(C_1-C_4)$-alkylamino,
  $R^{13B}$ is hydrogen, fluorine or $(C_1-C_4)$-alkyl,
    in which $(C_1-C_4)$-alkyl may be up to pentasubstituted by fluorine,
  $R^{14}$ is hydrogen or methyl,
$R^{11}$ is hydrogen, cyano, $(C_1-C_4)$-alkyl, acetyl or formyl,
  in which $(C_1-C_4)$-alkyl may be substituted by hydroxyl or up to pentasubstituted by fluorine,
  in which acetyl may be substituted by hydroxyl or up to trisubstituted by fluorine,
$R^{12}$ is hydrogen, fluorine or $(C_1-C_4)$-alkyl,
or
$R^{11}$ and $R^{12}$ together with the carbon atoms to which they are bonded form a cyclopropyl or cyclobutyl ring,
  in which the cyclopropyl or cyclobutyl ring may be up to disubstituted by fluorine,
or
$R^{12}$ and $R^{13A}$ together with the carbon atoms to which they are bonded form a cyclopropyl or cyclobutyl ring,
  in which the cyclopropyl or cyclobutyl ring may be up to disubstituted by fluorine,
or
$R^{13A}$ and $R^{13B}$ together with the carbon atom to which they are bonded form a cyclopropyl or cyclobutyl ring,
  in which the cyclopropyl or cyclobutyl ring may be up to disubstituted by fluorine,
where $R^{12}$, $R^{13A}$ and $R^{13B}$ are hydrogen when $R^{11}$ is not hydrogen,
where $R^{11}$ is hydrogen when one of the $R^{12}$, $R^{13A}$ or $R^{13B}$ substituents is not hydrogen,
or
is a group of the formula

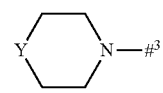

where
$\#^3$ marks the bond to the carbonyl carbon atom,
Y is $NR^{15}$, $CR^{16A}R^{16B}$, oxygen or sulfur,
  in which
  $R^{15}$ is hydrogen or methyl,
  $R^{16A}$ is hydrogen or methyl,
  $R^{16B}$ is hydrogen or methyl;
$R^3$ is hydrogen,
$R^4$ is hydrogen or $(C_1-C_4)$-alkyl,
  in which $(C_1-C_4)$-alkyl may be substituted by $(C_1-C_4)$-alkoxy, hydroxyl, mono-$(C_1-C_4)$-alkylamino or di-$(C_1-C_4)$-alkylamino and up to pentasubstituted by fluorine,
$R^5$ is hydrogen,
and the salts, solvates and solvates of the salts of the compounds of the formula (I).

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are cited below as working examples and the salts, solvates and solvates of the salts thereof if the compounds that are encompassed by formula (I) and are mentioned below are not already salts, solvates and solvates of the salts.

Preferred salts in the context of the present invention are physiologically acceptable salts of the compounds of the invention. Also encompassed are salts which are not themselves suitable for pharmaceutical applications but can be used, for example, for isolation or purification of the compounds of the invention.

Physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatographic processes are preferably used for this purpose, especially HPLC chromatography on an achiral or chiral phase. In the case of carboxylic acids as intermediates or end products, separation is alternatively also possible via diastereomeric salts using chiral amine bases.

If the compounds of the invention can occur in tautomeric forms, the present invention encompasses all the tautomeric forms.

The compounds of the general formula (I) may take the form of isotopic variants. The invention therefore encompasses one or more isotopic variants of the compounds of the general formula (I), especially deuterium-containing compounds of the general formula (I).

The term "isotopic variant" of a compound or reagent is defined as a compound with an unnatural fraction of one or more isotopes from which such a compound is constituted.

The term "isotopic variant of the compound of the general formula (I)" is defined as a compound of the general formula (I) with an unnatural fraction of one or more isotopes from which such a compound is formed.

The expression "unnatural fraction" is understood to mean a fraction of such an isotope higher than its natural frequency. The natural frequencies of isotopes to be employed in this connection can be found in "Isotopic Compositions of the Elements 1997", Pure Appl. Chem., 70(1), 217-235, 1998.

Examples of such isotopes are stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I.

With regard to the treatment and/or prophylaxis of the disorders specified here, the isotopic variant(s) of the compounds of the general formula (I) preferably contain deuterium ("deuterium-containing compounds of the general formula (I)"). Isotopic variants of the compounds of the general formula (I) into which one or more radioactive isotopes such as $^3$H or $^{14}$C have been incorporated are beneficial, for example, in medicament and/or substrate tissue distribution studies. Because of their easy incorporability and detectability, these isotopes are particularly preferred. It is possible to incorporate positron-emitting isotopes such as $^{18}$F or $^{11}$C into a compound of the general formula (I). These isotopic variants of the compounds of the general formula (I) are suitable for use in in vivo imaging applications. Deuterium-containing and $^{13}$C-containing compounds of the general formula (I) can be used within preclinical or clinical studies in mass spectrometry analyses.

Isotopic variants of the compounds of the general formula (I) can generally be prepared by processes known to those skilled in the art as described in the schemes and/or examples described here, by replacing a reagent with an isotopic variant of the reagent, preferably a deuterium-containing reagent. According to the desired deuteration sites, in some cases, deuterium from D$_2$O can either be incorporated directly into the compounds or into reagents which can be used for the synthesis of such compounds. Another useful reagent for incorporation of deuterium into molecules is deuterium gas. A rapid route to the incorporation of deuterium is the catalytic deuteration of olefinic bonds and acetylenic bonds. For direct exchange of hydrogen for deuterium in hydrocarbons containing functional groups, it is also possible to use metal catalysts (i.e. Pd, Pt and Rh) in the presence of deuterium gas. Various deuterated reagents and synthesis units are commercially available from companies like, for example, C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of the general formula (I)" is defined as a compound of the general formula (I) in which one or more hydrogen atoms have been replaced by one or more deuterium atoms and in which the frequency of deuterium in every deuterated position in the compound of the general formula (I) is higher than the natural frequency of deuterium, which is about 0.015%. More particularly, in a deuterium-containing compound of the general formula (I), the frequency of deuterium in every deuterated position in the compound of the general formula (I) is higher than 10%, 20%, 30%, 40%, 50%, 60%, 70% or 80%, preferably higher than 90%, 95%, 96% or 97%, even further preferably higher than 98% or 99%, in this position or these positions. It will be apparent that the frequency of deuterium in every deuterated position is independent of the frequency of deuterium in other deuterated positions.

Through the selective incorporation of one or more deuterium atoms into a compound of the general formula (I), it is possible to alter the physicochemical properties (for example acidity [C. L. Perrin, et al., *J. Am. Chem. Soc.*, 2007, 129, 4490], basicity [C. L. Perrin et al., *J. Am. Chem. Soc.*, 2005, 127, 9641], lipophilicity [B. Testa et al., Int. J. Pharm., 1984, 19(3), 271]) and/or the metabolic profile of the molecule and cause changes in the ratio of parent compound to metabolites or the amounts of metabolites formed. Such changes may lead to particular therapeutic benefits and therefore be preferable under particular circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent compound and metabolites can have important consequences with respect to the pharmacodynamics, tolerability and efficacy of a deuterium-containing compound of the general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. Examples of this deuterium effect are ML-337 (C. J. Wenthur et al., J. Med. Chem., 2013, 56, 5208) and odanacatib (K. Kassahun et al., WO2012/112363). Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

The present invention additionally also encompasses prodrugs of the compounds of the invention. The term "prodrugs" in this context denotes compounds which may themselves be biologically active or inactive but are converted (for example metabolically or hydrolytically) to compounds of the invention during their residence time in the body.

In the context of the present invention, unless specified otherwise, the substituents are defined as follows:

Alkyl in the context of the invention is a straight-chain or branched alkyl radical having the particular number of carbon atoms specified. Preferred examples include: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl, 1,4-dimethylpentyl, 4,4-dimethylpentyl and 1,4,4-trimethylpentyl.

Alkylcarbonyl in the context of the invention is a straight-chain or branched alkyl radical having the particular number of carbon atoms specified and a carbonyl group attached to the carbon atom. Preferred examples include: methylcarbonyl, ethylcarbonyl, n-propylcarbonyl, isopropylcarbonyl and tert-butylcarbonyl.

Alkoxy in the context of the invention is a straight-chain or branched alkoxy radical having the particular number of carbon atoms specified. Preferred examples include: methoxy, ethoxy, n-propoxy, isopropoxy, n-butoxy and tert-butoxy.

Cycloalkoxy in the context of the invention is a monocyclic saturated alkyl radical which has the particular number of ring carbon atoms specified and is joined via an oxygen atom. Preferred examples include: cyclopropyloxy, cyclobutyloxy, cyclopentyloxy and cyclohexyloxy.

Cycloalkyl or carbocycle in the context of the invention is a monocyclic saturated alkyl radical having the particular number of ring carbon atoms specified. Preferred examples include: cyclopropyl, cyclobutyl, cyclopentyl, cyclohexyl and cycloheptyl.

Cycloalkylcarbonyl in the context of the invention is a monocyclic saturated alkyl radical having the particular number of ring carbon atoms specified and a carbonyl group attached to the carbon atom. Preferred examples include: cyclopropylcarbonyl, cyclobutylcarbonyl, cyclopentylcarbonyl, cyclohexylcarbonyl and cycloheptylcarbonyl.

Alkoxycarbonyl in the context of the invention is a straight-chain or branched alkoxy radical having the particular number of carbon atoms specified and a carbonyl group attached to the oxygen atom. Preferred examples include: methoxycarbonyl, ethoxycarbonyl, n-propoxycarbonyl, isopropoxycarbonyl and tert-butoxycarbonyl.

Heterocycle or heterocyclyl in the context of the invention is a monocyclic or bicyclic, saturated heterocycle which has the particular number of ring atoms specified, contains one or two ring heteroatoms from the group of N, O, S, SO and $SO_2$ and is joined via a ring carbon atom or optionally a ring nitrogen atom. Examples include: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

Azaheterocyclyl in the context of the invention is a monocyclic or bicyclic, saturated or partly unsaturated heterocycle which has the particular number of ring atoms specified, contains a nitrogen atom and may additionally contain one or two further ring heteroatom(s) from the group of N, O, S, SO and/or $SO_2$, and is joined via a ring nitrogen atom. Examples include: pyrrolidinyl, pyrazolidinyl, piperidinyl, piperazinyl, morpholinyl, thiomorpholinyl, 1,1-dioxothiomorpholinyl, hexahydroazepinyl, hexahydro-1,4-diazepinyl, 1,2,3,4-tetrahydroisoquinolinyl, 1,2,3,4- tetrahydroquinolinyl, indolinyl, 8-azabicyclo[3.2.1]octanyl, 9-azabicyclo[3.3.1]nonanyl, 3-azabicyclo[4.1.0]heptanyl and quinuclidinyl.

Heteroaryl in the context of the invention is a monocyclic or bicyclic aromatic heterocycle (heteroaromatic) which has the particular number of ring atoms specified, contains up to four identical or different ring heteroatoms from the group of N, O and S and is joined via a ring carbon atom or optionally via a ring nitrogen atom. Preferred examples include: furyl, pyrrolyl, thienyl, pyrazolyl, imidazolyl, quinolinyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl and triazinyl.

Monoalkylaminocarbonyl in the context of the invention is an amino group which is joined via a carbonyl group and has a straight-chain or branched alkyl substituent having the particular number of carbon atoms specified. Preferred examples include: methylaminocarbonyl, ethylaminocarbonyl, n-propylaminocarbonyl, isopropylaminocarbonyl, n-butylaminocarbonyl, tert-butylaminocarbonyl, n-pentylaminocarbonyl and n-hexylaminocarbonyl.

Dialkylaminocarbonyl in the context of the invention is an amino group which is joined via a carbonyl group and has two identical or different, straight-chain or branched alkyl substituents each having the particular number of carbon atoms specified. Preferred examples include: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl, N-tert-butyl-N-methylaminocarbonyl, N-n-pentyl-N-methylaminocarbonyl and N-n-hexyl-N-methylaminocarbonyl.

Monoalkylaminosulfonyl in the context of the invention is an amino group which is joined via a sulfonyl group and has a straight-chain or branched alkyl substituent having the particular number of carbon atoms specified. Preferred examples include: methylaminosulfonyl, ethylaminosulfonyl, n-propylaminosulfonyl, isopropylaminosulfonyl, n-butylaminosulfonyl, tert-butylaminosulfonyl, n-pentylaminosulfonyl and n-hexylaminosulfonyl.

Dialkylaminocarbonyl in the context of the invention is an amino group which is joined via a sulfonyl group and has two identical or different, straight-chain or branched alkyl substituents each having the particular number of carbon atoms specified. Preferred examples include: N,N-dimethylaminosulfonyl, N,N-diethylaminosulfonyl, N-ethyl-N-methylaminosulfonyl, N-methyl-N-n-propylaminosulfonyl, N-n-butyl-N-methylaminosulfonyl, N-tert-butyl-N-methylaminosulfonyl, N-n-pentyl-N-methylaminosulfonyl and N-n-hexyl-N-methylaminosulfonyl.

Monoalkylamino in the context of the invention is an amino group having a linear or branched alkyl substituent having the particular number of carbon atoms specified. Preferred examples include: methylamino, ethylamino, n-propylamino, isopropylamino, n-butylamino, tert-butylamino, n-pentylamino and n-hexylamino.

Dialkylamino in the context of the invention is an amino group having two identical or different, straight-chain or branched alkyl substituents each having the particular number of carbon atoms specified. Preferred examples include: N,N-dimethylamino, N,N-diethylamino, N-ethyl-N-methylamino, N-methyl-N-n-propylamino, N-n-butyl-N-methylamino, N-tert-butyl-N-methylamino, N-n-pentyl-N-methylamino and N-n-hexyl-N-methylamino.

Halogen in the context of the invention includes fluorine, chlorine, bromine and iodine. Preference is given to chlorine or fluorine.

An oxo group in the context of the invention is an oxygen atom attached to a carbon atom via a double bond.

In the formulae of the group that A, X and $R^2$ can represent, the end point of the line marked by a symbol $\#^1$ or $\#^2$ or $\#^3$ or $\#^4$ or $\#^5$ or * or  or * does not represent a carbon atom or a $CH_2$ group, but is part of the bond to the respective atom to which A, X and $R^2$ are bonded.

When radicals in the compounds of the invention are substituted, the radicals may be mono- or polysubstituted, unless specified otherwise. In the context of the present invention, all radicals which occur more than once are defined independently of one another. Substitution by one or two identical or different substituents is preferred. Very particular preference is given to substitution by one substituent.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, preference is given to compounds of the general formula (I) in which
A is $(C_1-C_4)$-alkylene,
X is a group of the formula

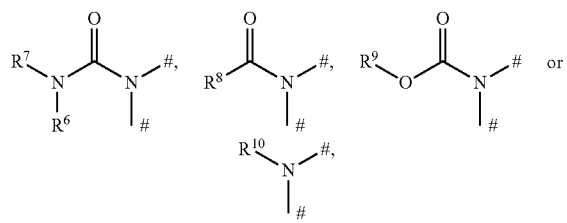

where
\# marks the bond to the respective carbon atom of the ring,
$R^6$ is $(C_1-C_6)$-alkyl, $(C_3-C_5)$-cycloalkyl, phenyl or 6-membered heteroaryl,
in which $(C_1-C_6)$-alkyl may be up to trisubstituted by fluorine,
in which $(C_3-C_5)$-cycloalkyl may be up to trisubstituted by fluorine,
in which phenyl may be substituted by 1 to 2 substituents selected independently from the group of fluorine, chlorine, bromine, cyano, trifluoromethyl, methyl, ethyl, methoxy and ethoxy,
in which 6-membered heteroaryl may be substituted by 1 to 2 substituents selected independently from the group of fluorine, chlorine, cyano, trifluoromethyl, methyl, ethyl, methoxy and ethoxy, R⁷ is hydrogen or methyl,
   in which methyl may be up to trisubstituted by fluorine,
R⁸ is $(C_1-C_4)$-alkyl, $(C_3-C_6)$-cycloalkyl, phenyl or 6-membered heteroaryl,
   in which $(C_1-C_6)$-alkyl may be up to trisubstituted by fluorine,
   in which $(C_3-C_5)$-cycloalkyl may be up to trisubstituted by fluorine,
R⁹ is $(C_1-C_4)$-alkyl or phenyl,
   in which $(C_1-C_4)$-alkyl may be up to trisubstituted by fluorine,
R¹⁰ is hydrogen, $(C_1-C_4)$-alkyl, $(C_3-C_6)$-cycloalkyl or phenyl,
   in which $(C_1-C_4)$-alkyl may be substituted by cyclopropyl or cyclobutyl or up to pentasubstituted by fluorine,
      in which cyclopropyl or cyclobutyl may be up to disubstituted by fluorine,
   in which $(C_3-C_6)$-cycloalkyl may be up to trisubstituted by fluorine,
   in which phenyl may be substituted by 1 to 3 substituents selected independently from the group of fluorine, chlorine, bromine, cyano, trifluoromethyl, methyl, ethyl, methoxy and ethoxy,
or
is oxygen,
R¹ is phenyl or 6-membered heteroaryl,
where phenyl is substituted by 1 to 3 substituents selected independently from the group of fluorine, chlorine, bromine, cyano, methyl, ethyl, cyclopropyl, trifluoromethyl, methoxy, ethoxy, monofluoromethoxy, difluoromethoxy, trifluoromethoxy, hydroxycarbonyl, hydroxycarbonyl, methoxycarbonyl, ethoxycarbonyl, tert-butoxycarbonyl, methylaminocarbonyl, dimethylaminocarbonyl,
where 6-membered heteroaryl is substituted by 1 to 3 substituents selected independently from the group of fluorine, chlorine, bromine, cyano, methyl, ethyl, cyclopropyl, trifluoromethyl, methoxy, ethoxy, monofluoromethoxy, difluoromethoxy, trifluoromethoxy, hydroxycarbonyl, hydroxycarbonyl, methoxycarbonyl, ethoxycarbonyl, tert-butoxycarbonyl, methylaminocarbonyl, dimethylaminocarbonyl,
R² is a group of the formula

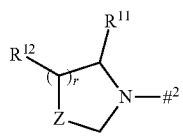

where
² marks the bond to the carbonyl carbon atom,
r is 1,
Z is $CR^{13A}R^{13B}$,
   in which
      $R^{13A}$ is hydrogen, fluorine, methyl, trifluoromethyl, difluoromethyl, fluoromethyl, hydroxyl, methoxy, difluoromethoxy or trifluoromethoxy,
      $R^{13B}$ is hydrogen or fluorine,
R¹¹ is hydrogen,
R¹² is hydrogen or fluorine,
R³ is hydrogen,
R⁴ is hydrogen, fluorine or methyl,
in which methyl may be up to trisubstituted by fluorine,
R⁵ is hydrogen,
and the salts, solvates and solvates of the salts of the compounds of the formula (I).

Particular preference in the context of the present invention is given to compounds of the general formula (I) in which
A is —CH₂—,
X is a group of the formula

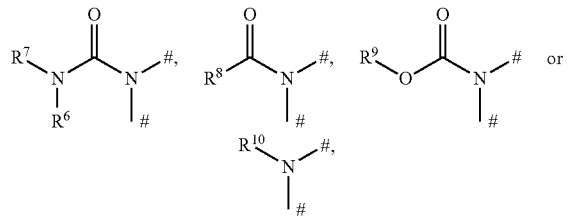

where
marks the bond to the respective carbon atom of the ring,
R⁶ is $(C_1-C_4)$-alkyl, cyclopropyl or phenyl,
   in which $(C_1-C_4)$-alkyl may be up to trisubstituted by fluorine,
   in which phenyl is substituted by 1 or 2 substituents selected independently from the group of chlorine and trifluoromethyl,
R⁷ is hydrogen,
R⁸ is methyl, ethyl, propyl, 3,3,3-trifluoropropyl or cyclopropyl,
R⁹ is tert-butyl,
R¹⁰ is hydrogen, methyl, ethyl, 2,2,2-trifluoroethyl, cyclopropyl or cyclobutyl,
   in which methyl may be substituted by cyclopropyl,
      in which cyclopropyl may be up to disubstituted by fluorine,
R¹ is phenyl or pyridyl,
where phenyl may be substituted by 1 or 2 substituents selected independently from the group of fluorine, methyl and trifluoromethyl,
where pyridyl may be substituted by 1 or 2 substituents selected independently from the group of fluorine, chlorine and trifluoromethyl,
R² is a group of the formula

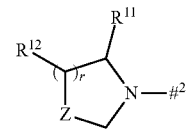

where
² marks the bond to the carbonyl carbon atom,
r is 1,
Z is $CR^{13A}R^{13B}$,
   in which
      $R^{13A}$ is hydrogen or fluorine,
      $R^{13B}$ is hydrogen,
R¹¹ is hydrogen,
R¹² is hydrogen or fluorine,
R³ is hydrogen,
R⁴ is hydrogen or methyl,
R⁵ is hydrogen,
and the salts, solvates and solvates of the salts of the compounds of the formula (I).

In the context of the present invention, preference is also given to compounds of the general formula (I) in which
A is —CH$_2$—,
and the solvates, salts and solvates of the salts thereof.

In the context of the present invention, preference is also given to compounds of the general formula (I) in which
X is a group of the formula

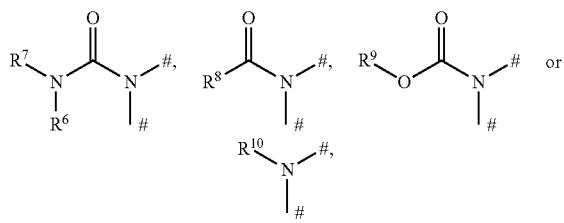

where
marks the bond to the respective carbon atom of the ring,
R$^6$ is (C$_1$-C$_4$)-alkyl, cyclopropyl or phenyl,
  in which (C$_1$-C$_4$)-alkyl may be up to trisubstituted by fluorine,
  in which phenyl is substituted by 1 or 2 substituents selected independently from the group of chlorine and trifluoromethyl,
R$^7$ is hydrogen,
R$^8$ is methyl, ethyl, propyl, 3,3,3-trifluoropropyl or cyclopropyl,
R$^9$ is tert-butyl,
R$^{10}$ is hydrogen, methyl, ethyl, 2,2,2-trifluoroethyl, cyclopropyl or cyclobutyl,
  in which methyl may be substituted by cyclopropyl,
    in which cyclopropyl may be up to disubstituted by fluorine,
and the solvates, salts and solvates of the salts thereof.

In the context of the present invention, preference is also given to compounds of the formula (I) in which
X is a group of the formula

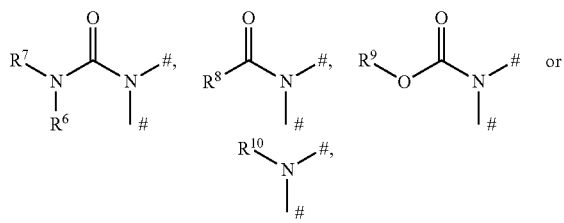

where
marks the bond to the respective carbon atom of the ring,
R$^6$ is (C$_1$-C$_4$)-alkyl, cyclopropyl or phenyl,
  in which (C$_1$-C$_4$)-alkyl may be up to trisubstituted by fluorine,
  in which phenyl is substituted by 1 or 2 substituents selected independently from the group of chlorine and trifluoromethyl,
R$^7$ is hydrogen,
R$^8$ is 3,3,3-trifluoropropyl or cyclopropyl,
R$^9$ is tert-butyl,
R$^{10}$ is hydrogen, methyl, 2,2,2-trifluoroethyl or cyclobutyl,
  in which methyl may be substituted by cyclopropyl,
    in which cyclopropyl may be up to disubstituted by fluorine,
and the solvates, salts and solvates of the salts thereof.

In the context of the present invention, preference is also given to compounds of the formula (I) in which
X is a group of the formula

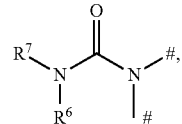

where
marks the bond to the respective carbon atom of the ring,
R$^6$ is (C$_1$-C$_4$)-alkyl, cyclopropyl or phenyl,
  in which (C$_1$-C$_4$)-alkyl may be up to trisubstituted by fluorine,
  in which phenyl is substituted by 1 or 2 substituents selected independently from the group of chlorine and trifluoromethyl,
R$^7$ is hydrogen,
and the solvates, salts and solvates of the salts thereof.

In the context of the present invention, preference is also given to compounds of the formula (I) in which
X is a group of the formula

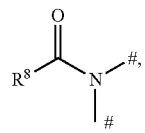

where
marks the bond to the respective carbon atom of the ring,
R$^8$ is 3,3,3-trifluoropropyl or cyclopropyl,
and the solvates, salts and solvates of the salts thereof.

In the context of the present invention, preference is also given to compounds of the formula (I) in which
X is a group of the formula

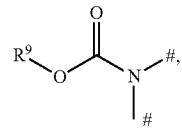

where
marks the bond to the respective carbon atom of the ring,
R$^9$ is tert-butyl,
and the solvates, salts and solvates of the salts thereof.

In the context of the present invention, preference is also given to compounds of the formula (I) in which
X is a group of the formula

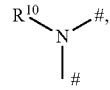

where
marks the bond to the respective carbon atom of the ring,
R$^{10}$ is hydrogen, methyl, 2,2,2-trifluoroethyl or cyclobutyl,
  in which methyl may be substituted by cyclopropyl,
    in which cyclopropyl may be up to disubstituted by fluorine,
and the solvates, salts and solvates of the salts thereof.

In the context of the present invention, preference is also given to compounds of the formula (I) in which
$R^1$ is phenyl or pyridyl,
where phenyl may be substituted by 1 or 2 substituents selected independently from the group of fluorine, methyl and trifluoromethyl,
where pyridyl may be substituted by 1 or 2 substituents selected independently from the group of fluorine, chlorine and trifluoromethyl,
and the solvates, salts and solvates of the salts thereof.

In the context of the present invention, preference is also given to compounds of the formula (I) in which
$R^1$ is phenyl,
where phenyl may be substituted by 1 or 2 substituents selected independently from the group of fluorine, methyl and trifluoromethyl,
and the solvates, salts and solvates of the salts thereof.

In the context of the present invention, preference is also given to compounds of the formula (I) in which
$R^1$ is pyridyl,
where pyridyl may be substituted by 1 or 2 substituents selected independently from the group of fluorine, chlorine and trifluoromethyl,
and the solvates, salts and solvates of the salts thereof.

In the context of the present invention, preference is also given to compounds of the formula (I) in which
$R^2$ is a group of the formula

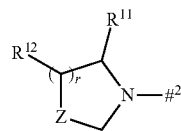

where
$^2$ marks the bond to the carbonyl carbon atom,
r is 1,
Z is $CR^{13A}R^{13B}$,
in which
$R^{13A}$ is hydrogen or fluorine,
$R^{13B}$ is hydrogen,
$R^{11}$ is hydrogen,
$R^{12}$ is hydrogen or fluorine, In the context of the present invention, preference is also given to compounds of the formula (I) in which
$R^3$ is hydrogen,
and the solvates, salts and solvates of the salts thereof.

In the context of the present invention, preference is also given to compounds of the formula (I) in which
$R^4$ is hydrogen or methyl,
and the solvates, salts and solvates of the salts thereof.

In the context of the present invention, preference is also given to compounds of the formula (I) in which
$R^5$ is hydrogen,
and the solvates, salts and solvates of the salts thereof.

The invention further provides a process for preparing the compounds of the formula (I) according to the invention, characterized in that
[A] a compound of the formula (II)

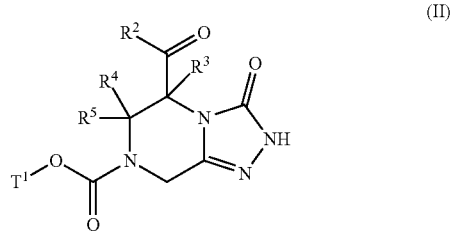

in which $R^1$, $R^2$, $R^3$, $R^4$ and $R^5$ each have the definitions given above, and
$T^1$ is ($C_1$-$C_4$)-alkyl or benzyl,
is reacted in an inert solvent in the presence of a suitable base with a compound of the formula (III)

in which
A and $R^1$ have the definitions given above,
and
$X^1$ is a suitable leaving group, especially chlorine, bromine, iodine, mesylate {(methylsulfonyl)oxy}, triflate {[(trifluoromethyl)sulfonyl]oxy}, nonaflate {[(nonafluorobutyl)sulfonyl]oxy}, nosylate {[(4-nitrophenyl)sulfonyl]oxy} or tosylate {[(4-methylphenyl)sulfonyl]oxy},
to give a compound of the formula (IV)

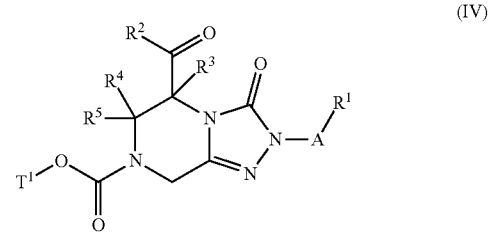

in which A, $R^1$, $R^2$, $R^3$, $R^4$, $R^5$ and $T^1$ each have the definitions given above,
then the latter are optionally converted by removing the "$T^1$" group in an inert solvent in the presence of a suitable base or acid to a compound of the formula (V)

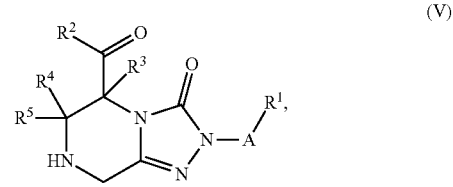

in which A, $R^1$, $R^2$, $R^3$, $R^4$ and $R^5$ each have the definitions given above, and the latter are then reacted, optionally in an inert solvent,
[A1] in the presence of a suitable base, with a compound of the formula (VI)

in which
$R^{10}$ has the definitions given above,
and
$X^2$ is a suitable leaving group, especially chlorine, bromine, iodine, mesylate {(methylsulfonyl)oxy}, triflate {[(trifluoromethyl)sulfonyl]oxy}, nonaflate {[(nonafluorobutyl)sulfonyl]oxy}, nosylate {[(4-nitrophenyl) sulfonyl]oxy} or tosylate {[(4-methylphenyl)sulfonyl] oxy}, and then any protecting groups present are detached by methods known to those skilled in the art, and the resulting compounds of the formula (I) are optionally converted with the appropriate (i) solvents and/or (ii) acids or bases to the solvates, salts and/or solvates of the salts thereof, or

[A2] in the presence of a suitable base, with a compound of the formula (VII)

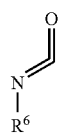

(VII)

in which

R$^6$ has the definitions given above, and then any protecting groups present are detached by methods known to those skilled in the art, and the resulting compounds of the formula (I) are optionally converted with the appropriate (i) solvents and/or (ii) acids or bases to the solvates, salts and/or solvates of the salts thereof, or

[A3] in the presence of a suitable base, with a compound of the formula (VIII)

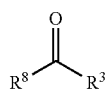

(VIII)

in which

R$^8$ has the definitions given above, and

X$^3$ is a suitable leaving group, especially chlorine, bromine or hydroxyl, and then any protecting groups present are detached by methods known to those skilled in the art, and the resulting compounds of the formula (I) are optionally converted with the appropriate (i) solvents and/or (ii) acids or bases to the solvates, salts and/or solvates of the salts thereof, or

[B] a compound of the formula (IX)

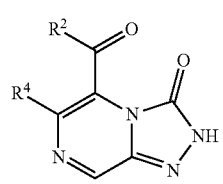

(IX)

in which R$^2$, R$^4$ and R$^5$ each have the definitions given above, is reacted in an inert solvent in the presence of a suitable base with a compound of the formula (III)

(III)

in which

A and R$^1$ have the definitions given above, and

X$^1$ is a suitable leaving group, especially chlorine, bromine, iodine, mesylate {(methylsulfonyl)oxy}, triflate {[(trifluoromethyl)sulfonyl]oxy}, nonaflate {[(non-afluorobutyl)sulfonyl]oxy}, nosylate {[(4-nitrophenyl) sulfonyl]oxy} or tosylate {[(4-methylphenyl)sulfonyl] oxy}, to give a compound of the formula (X)

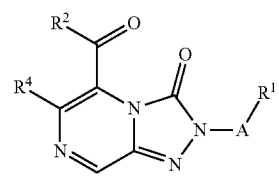

(X)

in which A, R$^1$, R$^2$ and R$^4$ each have the definitions given above, and then, in a suitable solvent, hydrogenated in the presence of a palladium catalyst in a hydrogen atmosphere, and the resulting compound of the formula (V)

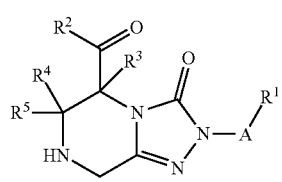

(V)

is converted as described under [A] and then any protecting groups present are detached by methods known to those skilled in the art, and the resulting compounds of the formula (I) are optionally converted with the appropriate (i) solvents and/or (ii) acids or bases to the solvates, salts and/or solvates of the salts thereof.

The compounds of the formulae (III), (VI), (VII) and (VIII) are commercially available or known from the literature, or can be prepared in analogy to processes known from the literature.

Inert solvents for the process step (II)+(III)→(IV) or (IX)+(III)→(X) are, for example, halohydrocarbons such as dichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, alcohols such as methanol, ethanol, n-propanol, isopropanol, n-butanol, 2,2,2-trifluoroethanol, or other solvents such as acetone, methyl ethyl ketone, ethyl acetate, acetonitrile, N,N-dimethylformamide, N,N-dimethylacetamide, dimethyl sulfoxide, N,N'-dimethylpropyleneurea (DMPU), N-methylpyrrolidone (NMP) or pyridine. It is equally possible to use mixtures of the solvents mentioned. Preference is given to using dimethylformamide or acetonitrile.

Suitable bases for the process step (II)+(III)→(IV) or (IX)+(III)→(X) are the customary inorganic or organic bases. These preferably include lithium, sodium, potassium, alkali metal hydroxides, for example lithium hydroxide, sodium hydroxide or potassium hydroxide, alkoxides such as potassium tert-butoxide, methoxide, ethoxide, alkali metal or alkaline earth metal carbonates such as lithium carbonate, sodium carbonate, potassium carbonate, calcium carbonate or cesium carbonate, optionally with addition of an alkali metal iodide, for example sodium iodide or potassium iodide, or organic amines such as triethylamine, N-methylmorpholine, N-methylpiperidine, N,N-diisopropylethylamine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using cesium carbonate.

The reaction is generally conducted within a temperature range from 0° C. to +120° C., preferably at +20° C. to +80° C., most preferably at room temperature, optionally in a microwave. The reaction can be conducted at standard, elevated or reduced pressure (for example from 0.5 to 5 bar).

The hydrolysis of the esters in the compounds (IV) to give compounds of the formula (V) is effected by customary methods, by treating the esters in inert solvents with acids or bases, in which latter case the salts formed at first are converted to the free carboxylic acids by treating with acid. In the case of the tert-butyl esters, the ester hydrolysis is preferably effected with acids.

Suitable inert solvents for these reactions are water or the organic solvents customary for ester cleavage. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichloromethane, dimethylformamide or dimethyl sulfoxide. It is equally possible to use mixtures of the solvents mentioned. In the case of a basic ester hydrolysis, preference is given to using mixtures of water with dioxane, tetrahydrofuran, methanol and/or ethanol and/or n-propanol. In the case of the reaction with trifluoroacetic acid preference is given to using dichloromethane, and in the case of the reaction with hydrogen chloride preference is given to using tetrahydrofuran, diethyl ether, dioxane or water.

Suitable bases are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates, such as sodium carbonate, potassium carbonate or calcium carbonate. Particular preference is given to sodium hydroxide or lithium hydroxide.

Suitable acids for the ester hydrolysis are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, optionally with addition of water. Preference is given to hydrogen chloride or trifluoroacetic acid in the case of the tert-butyl esters and to hydrochloric acid in the case of the methyl esters.

The ester hydrolysis is generally effected within a temperature range from 0° C. to +100° C., preferably at +0° C. to +50° C., more preferably at room temperature.

These conversions can be performed at atmospheric, elevated or reduced pressure (for example from 0.5 to 5 bar). In general, standard pressure is employed in each case.

Inert solvents for the reaction (V)+(VI)→(I) are, for example, halohydrocarbons such as dichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, alcohols such as methanol, ethanol, n-propanol, isopropanol, n-butanol, 2,2,2-trifluoroethanol, or other solvents such as acetone, methyl ethyl ketone, ethyl acetate, acetonitrile, N,N-dimethylformamide, N,N-dimethylacetamide, dimethyl sulfoxide, N,N'-dimethylpropyleneurea (DMPU), N-methylpyrrolidone (NMP) or pyridine. It is equally possible to use mixtures of the solvents mentioned. Preference is given to using dimethylformamide or acetonitrile.

Suitable bases for the process step (V)+(VI)→(I) are the customary inorganic or organic bases. These preferably include lithium, sodium, potassium, alkali metal hydroxides, for example lithium hydroxide, sodium hydroxide or potassium hydroxide, alkoxides such as potassium tert-butoxide, methoxide, ethoxide, alkali metal or alkaline earth metal carbonates such as lithium carbonate, sodium carbonate, potassium carbonate, calcium carbonate or cesium carbonate, optionally with addition of an alkali metal iodide, for example sodium iodide or potassium iodide, or organic amines such as triethylamine, N-methylmorpholine, N-methylpiperidine, N,N-diisopropylethylamine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using cesium carbonate.

The reaction is generally conducted within a temperature range from 0° C. to +120° C., preferably at +20° C. to +80° C., most preferably at room temperature, optionally in a microwave. The reaction can be conducted at standard, elevated or reduced pressure (for example from 0.5 to 5 bar).

Inert solvents for the reaction (V)+(VII)→(I) are, for example, halohydrocarbons such as dichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, alcohols such as methanol, ethanol, n-propanol, isopropanol, n-butanol, 2,2,2-trifluoroethanol, or other solvents such as acetone, methyl ethyl ketone, ethyl acetate, acetonitrile, N,N-dimethylformamide, N,N-dimethylacetamide, dimethyl sulfoxide, N,N'-dimethylpropyleneurea (DMPU), N-methylpyrrolidone (NMP) or pyridine. It is equally possible to use mixtures of the solvents mentioned. Preference is given to using dimethylformamide or acetonitrile.

Suitable bases for the process step (V)+(VII)→(I) are the customary inorganic or organic bases. These preferably include lithium, sodium, potassium, alkoxides such as potassium tertbutoxide, methoxide, ethoxide, alkali metal or alkaline earth metal carbonates such as lithium carbonate, sodium carbonate, potassium carbonate, calcium carbonate or cesium carbonate, optionally with addition of an alkali metal iodide, for example sodium iodide or potassium iodide, or organic amines such as triethylamine, N-methylmorpholine, N-methylpiperidine, N,N-diisopropylethylamine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using cesium carbonate.

The reaction is generally conducted within a temperature range from 0° C. to +120° C., preferably at +20° C. to +80° C., most preferably at room temperature, optionally in a microwave. The reaction can be conducted at standard, elevated or reduced pressure (for example from 0.5 to 5 bar).

Inert solvents for the amide coupling (V)+(VIII)→(I) when $X^3$ is hydroxyl are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulfoxide, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

Suitable for use as condensing agents for the amide formation (V)+(VIII)→(I) when $X^3$ is hydroxyl are, for example, carbodiimides such as N,N'-diethyl-, N,N'-dipropyl-, N,N'-diisopropyl, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline or isobutyl chloroformate, propanephosphonic anhydride (T3P), 1-chloro-N,N,2-trimethylprop1-ene-1-amine, diethyl cyanophosphonate, bis(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), 0-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate or sodium hydrogencarbonate or potassium hydrogencarbonate, or organic bases such as trialkylamines, for example triethylamine, N-methylmorpholine, N-methylpiperidine or N,N-diisopropylethylamine. Preference is given to using HATU.

The condensations (V)+(VIII)→(I) when $X^3$ is hydroxyl is generally conducted within a temperature range from −20° C. to +100° C., preferably at 0° C. to +60° C. The conversion can be effected at standard, elevated or reduced pressure (for example from 0.5 to 5 bar). In general, standard pressure is employed.

Alternatively, the carboxylic acid of the formula (VIII, when $X^3$ is hydroxyl) can also first be converted to the corresponding carbonyl chloride and the latter can then be reacted directly or in a separate reaction with an amine of the formula (VI) to the compounds of the invention. The formation of carbonyl chlorides from carboxylic acids is effected by the methods known to those skilled in the art, for example by treatment with thionyl chloride or oxalyl chloride, in the presence of a suitable base, for example in the presence of pyridine, and optionally with addition of dimethylformamide, optionally in a suitable inert solvent.

Inert solvents for the reaction (V)+(VIII)→(I) when $X^3$ is chlorine or bromine are, for example, halohydrocarbons such as dichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, alcohols such as methanol, ethanol, n-propanol, isopropanol, n-butanol, 2,2,2-trifluoroethanol, or other solvents such as acetone, methyl ethyl ketone, ethyl acetate, acetonitrile, N,N-dimethylformamide, N,N-dimethylacetamide, dimethyl sulfoxide, N,N'-dimethylpropyleneurea (DMPU), N-methylpyrrolidone (NMP) or pyridine. It is equally possible to use mixtures of the solvents mentioned. Preference is given to using dichloromethane.

Suitable bases for the process step (V)+(VIII)→(I) when $X^3$ is chlorine or bromine are the customary inorganic or organic bases. These preferably include lithium, sodium, potassium, alkali metal hydroxides, for example alkoxides such as potassium tert-butoxide, methoxide, ethoxide, alkali metal or alkaline earth metal carbonates such as lithium carbonate, sodium carbonate, potassium carbonate, calcium carbonate or cesium carbonate, optionally with addition of an alkali metal iodide, for example sodium iodide or potassium iodide, or organic amines such as triethylamine, N-methylmorpholine, N-methylpiperidine, N,N-diisopropylethylamine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using cesium carbonate.

The reaction is generally conducted within a temperature range from 0° C. to +120° C., preferably at +20° C. to +80° C., most preferably at room temperature, optionally in a microwave. The reaction can be conducted at standard, elevated or reduced pressure (for example from 0.5 to 5 bar).

Inert solvents for the process step (X)→(V) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, ethyl acetate, acetonitrile, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

The process step (X)→(V) is generally conducted within a temperature range from −20° C. to +100° C., preferably at 0° C. to +60° C. The conversion can be effected at standard or elevated hydrogen pressure (for example from 1.0 to 100 bar). In general, elevated hydrogen pressure is employed.

The compounds of the formula (II) can be prepared by reacting a compound of the formula (XI)

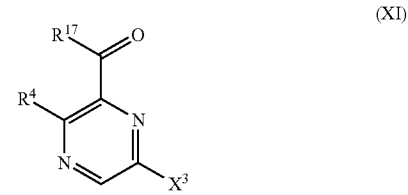

in which $R^{17}$ is hydroxyl, chlorine, bromine or iodine $X^3$ is fluorine, chlorine, bromine or iodine, and $R^4$ has the definitions given above, in an inert solvent under amide coupling conditions, with an amine of the formula (VI-A) or (VI-B)

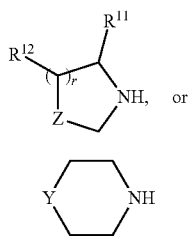
(XII-A)

or

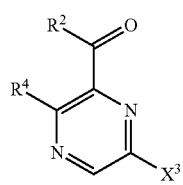
(XII-B)

in which Y, Z, $R^{11}$ and $R^{12}$ each have the definitions given above,
to give a compound of the formula (XIII)

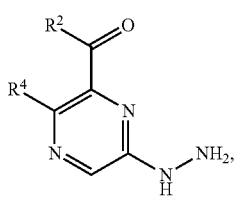
(XIII)

in which
$X^3$ is fluorine, chlorine, bromine or iodine,
and $R^4$ and $R^2$ each have the definitions given above,
and
[A4] these are converted in an inert solvent, optionally in the presence of a suitable base and optionally of a palladium catalyst, with hydrazine hydrate or a suitable hydrazine derivative to a compound of the formula (XIV)

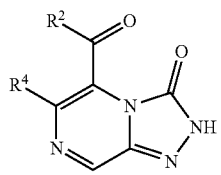
(XIV)

in which
$R^2$ and $R^4$ each have the definitions given above,
and these are cyclized in a suitable solvent with a phosgene derivative to give a compound of the formula (IX)

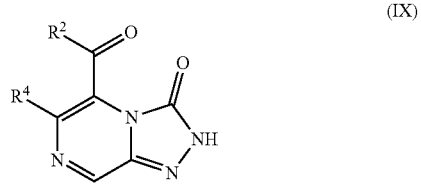
(IX)

in which $R^2$ and $R^4$ each have the definitions given above,
and then hydrogenated in a suitable solvent in the presence of a palladium catalyst and di-tertbutyl dicarbonate in a hydrogen atmosphere, and the resulting compounds of the formulae (II) are optionally converted with the appropriate (i) solvents and/or (ii) acids or bases to the solvates, salts and/or solvates of the salts thereof,
or
[A5] these are converted in an inert solvent in the presence of a suitable base and optionally of a palladium catalyst with a compound of the formula XII

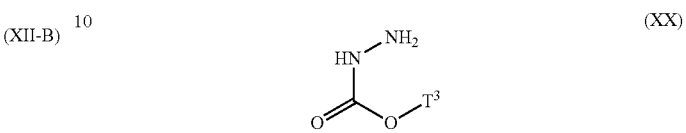
(XX)

in which
$T^3$ is benzyl or tert-butyl,
to give a compound of the formula (XXI)

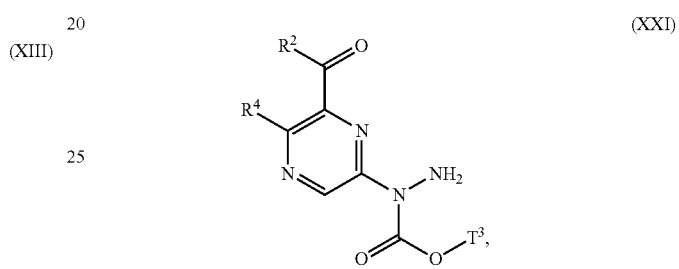
(XXI)

in which
$R^2$, $R^4$ and $T^3$ each have the definitions given above,
the protecting group $T^3$ is detached in a suitable inert solvent by hydrogenolysis in the presence of a palladium catalyst and the resulting compound of the formula (XIV)

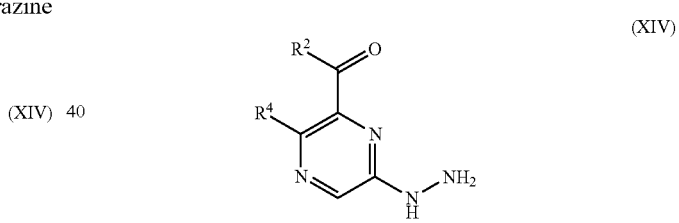
(XIV)

is cyclized in a suitable solvent with a phosgene derivative of the formula (IX)

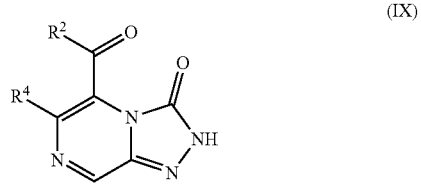
(IX)

in which $R^2$ and $R^4$ each have the definitions given above,
and then hydrogenated in a suitable solvent in the presence of a palladium catalyst and di-tertbutyl dicarbonate in a hydrogen atmosphere,
and the resulting compounds of the formulae (II) are optionally converted with the appropriate (i) solvents and/or (ii) acids or bases to the solvates, salts and/or solvates of the salts thereof.

The compounds of the formulae (XI), (XII-A) and (XII-B) are commercially available or known from the literature, or can be prepared in analogy to processes known from the literature.

The processes described are illustrated by way of example by the schemes below (Schemes 1-2):

Scheme 1

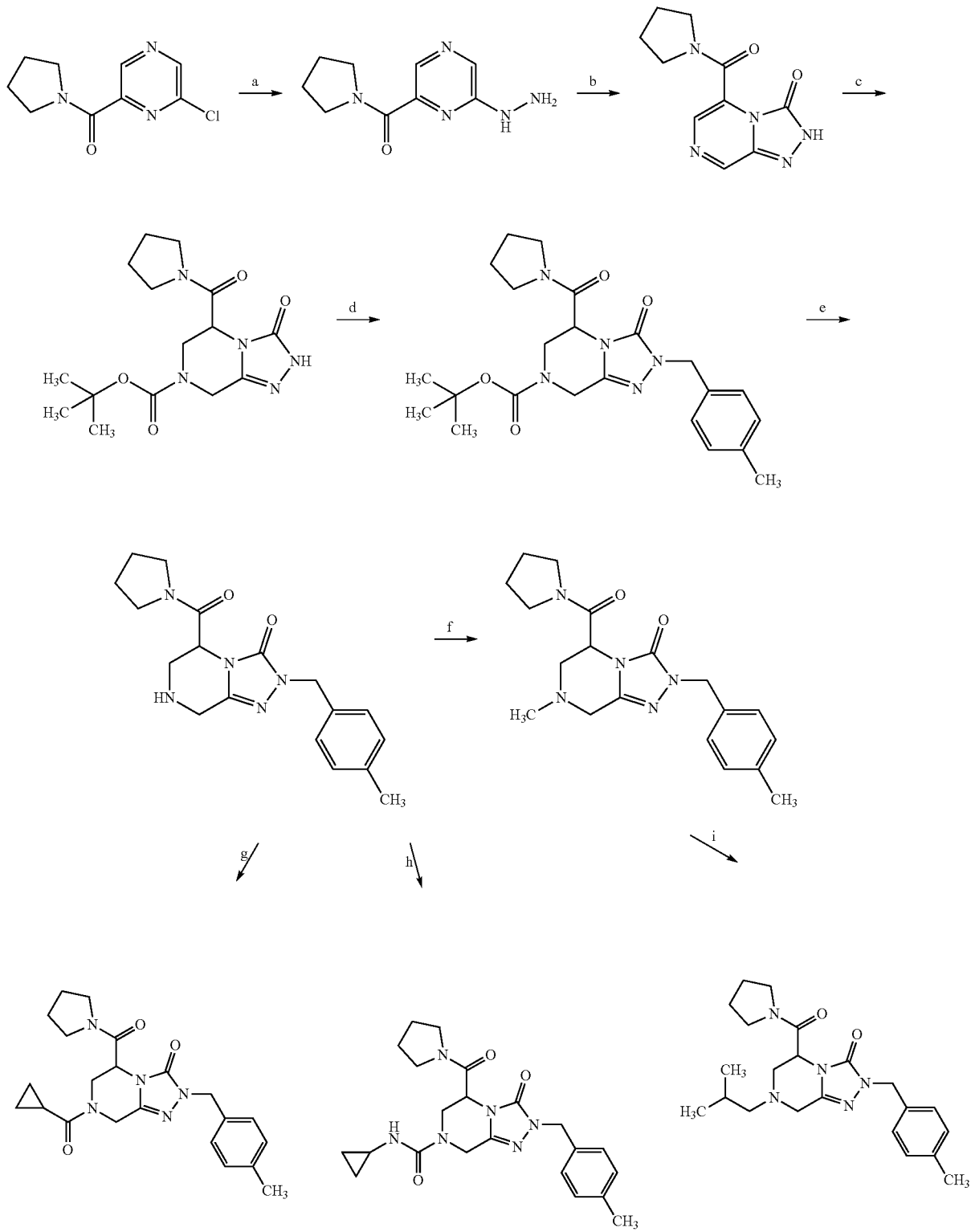

a) hydrazine hydrate, ethanol, 80° C.; b) carbonyldiimidazole, THF, RT; c) Pd/C 5%, 1 bar $H_2$ in 1,4-dioxane, di-tert-butyl dicarbonate, RT; d) cesium carbonate, 1-(bromomethyl)-3,5-dichlorobenzene in acetonitrile, RT; e) trifluoroacetic acid, dichloromethane, RT; f) iodomethane, N,N-diisopropylethylamine, THF, RT; g) cyclopropanecarbonyl chloride, N,N-diisopropylethylamine, THF, RT; h) isocyanatocyclopropane, dichloromethane, RT; i) 2-methylpropanal, sodium triacetoxyborohydride, acetic acid, THF, RT.

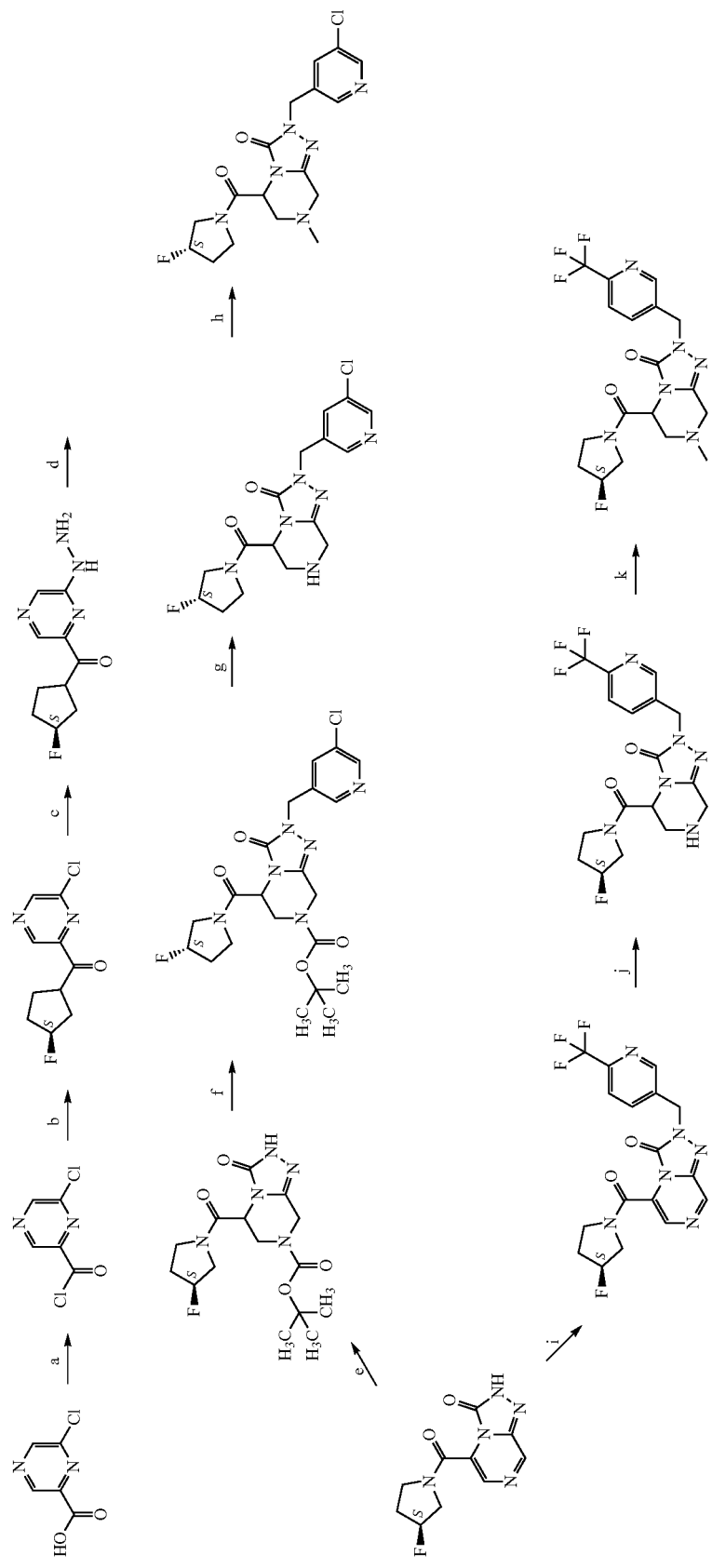

Scheme 2 a) thionyl chloride, 90° C.; b) (3S)-3-fluoropyrrolidine hydrochloride, N,N-diisopropylethylamine, dichloromethane, RT; c) hydrazine hydrate, ethanol, 80° C.; d) carbonyldiimidazole, THF, RT; e) Pd/C 5%, 1 bar H₂ in 1,4-dioxane, di-tert-butyl dicarbonate, RT f) cesium carbonate, 3-chloro-5-(chloromethyl)pyridine, acetonitrile, RT; g) trifluoroacetic acid, dichloromethane, RT; h) iodomethane, N,N-diisopropylethylamine, THF, RT; i) cesium carbonate, 5-(chloromethyl)-2-(trifluoromethyl)pyridine hydrochloride, acetonitrile, RT; i) Pd/C 10%, 1 bar H₂ in methanol/ethanol, 95° C.; k) formaldehyde, sodium triacetoxyborohydride, acetic acid, THF, RT.

Inert solvents for the amide coupling (XI)+(XII-A)→(XIII) or (XI)+(XII-B)→(XIII) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulfoxide, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

Suitable condensing agents for the amide formation (XI)+(XII-A)→(XIII) or (XI)+(XII-B)→(XIII) are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline or isobutyl chloroformate, propanephosphonic anhydride (T3P), 1-chloro-N,N,2-trimethylprop-1-ene-1-amine, diethyl cyanophosphonate, bis(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), 0-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate or sodium hydrogencarbonate or potassium hydrogencarbonate, or organic bases such as trialkylamines, for example triethylamine, N-methylmorpholine, N-methylpiperidine or N,N-diisopropylethylamine. Preference is given to using HATU.

The condensations (XI)+(XII-A)→(XIII) or (XI)+(XII-B)→(XIII) is generally conducted within a temperature range from –20° C. to +100° C., preferably at 0° C. to +60° C. The conversion can be effected at standard, elevated or reduced pressure (for example from 0.5 to 5 bar). In general, standard pressure is employed.

Alternatively, the carboxylic acid of the formula (XI, when $R^{17}$ is hydroxyl) can also first be converted to the corresponding carbonyl chloride and the latter can then be reacted directly or in a separate reaction with an amine of the formula (VI) to the compounds of the invention. The formation of carbonyl chlorides from carboxylic acids is effected by the methods known to those skilled in the art, for example by treatment with thionyl chloride or oxalyl chloride, in the presence of a suitable base, for example in the presence of pyridine, and optionally with addition of dimethylformamide, optionally in a suitable inert solvent.

Process step (XIII)→(XIV) is carried out in a solvent which is inert under the reaction conditions. Suitable solvents are, for example, ethers such as 1,4-dioxane, tetrahydrofuran, 2-methyltetrahydrofuran, diethyl ether, di-n-butyl ether, glycol dimethyl ether or diethylene glycol dimethyl ether, alcohols such as methanol, ethanol, tert-butanol or amyl alcohols or other solvents such as dimethylformamide (DMF), dimethyl sulfoxide (DMSO), dimethylacetamide (DMA), toluene or acetonitrile. It is equally possible to use mixtures of the solvents mentioned. Preference is given to ethanol.

The process step (XIII)→(XIV) is generally conducted within a temperature range from 0° C. to +200° C., preferably at +10° C. to +150° C. The conversions can also be effected in closed vessels (microwave tubes) in the microwave. The conversion can be effected at standard, elevated or reduced pressure (for example from 0.5 to 5 bar). Operations generally take place at standard pressure or in closed vessels (microwave tubes) below or above the boiling point of the solvent used. Preference is given to reactions in closed vessels (microwave tubes), at temperatures above the boiling point of the solvent and under elevated pressure, with or without use of a microwave.

Inert solvents for the process step (XIV)→(IX) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulfoxide, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

Examples of suitable phosgene derivatives used for the process step (XIV)→(IX) are, for example, N,N-carbonyldiimidazole (CDI), trichloromethyl chlorocarbonate (diphosgene), bis(trichloromethyl) carbonate (triphosgene) or aryl chloroformate. Preference is given to using N,N'-carbonyldiimidazole (CDI).

The process step (XIV)→(IX) is generally conducted within a temperature range from –20° C. to +100° C., preferably at 0° C. to +60° C. The conversion can be effected at standard, elevated or reduced pressure (for example from 0.5 to 5 bar). In general, standard pressure is employed.

Inert solvents for the process step (IX)→(II) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, ethyl acetate, acetonitrile, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

The process step (IX)→(II) is generally conducted within a temperature range from –20° C. to +100° C., preferably at 0° C. to +60° C. The conversion can be effected at standard or elevated hydrogen pressure (for example from 1.0 to 100 bar). In general, elevated hydrogen pressure is employed.

Any hydroxyl, amino and/or amido groups present in the starting compounds of formulae (II) can, if appropriate or necessary, also be used in temporarily protected form and then released again at the end of the particular reaction sequence [with regard to the suitability, introduction and removal of such protecting groups see, for example, T. W.

Greene and P. G. M. Wuts, *Protective Groups in Organic Synthesis*, Wiley, New York, 1999].

Further compounds of the invention can optionally also be prepared by conversions of functional groups of individual substituents, especially those listed for $R^1$, $R^2$, $R^4$, proceeding from the compounds of the formula (I) obtained by above processes. These conversions are conducted by customary methods known to those skilled in the art and include, for example, reactions such as nucleophilic and electrophilic substitutions, oxidations, reductions, hydrogenations, transition metal-catalyzed coupling reactions, eliminations, alkylation, amination, esterification, ester hydrolysis, etherification, ether hydrolysis, formation of carbonamides, dehydrations, and introduction and removal of temporary protective groups.

Detailed procedures can also be found in the Experimental part, in the section on the preparation of the starting compounds and intermediates.

Inventive compounds of the formula (I) in which X is oxygen can be prepared as shown in the scheme below (Scheme 3).

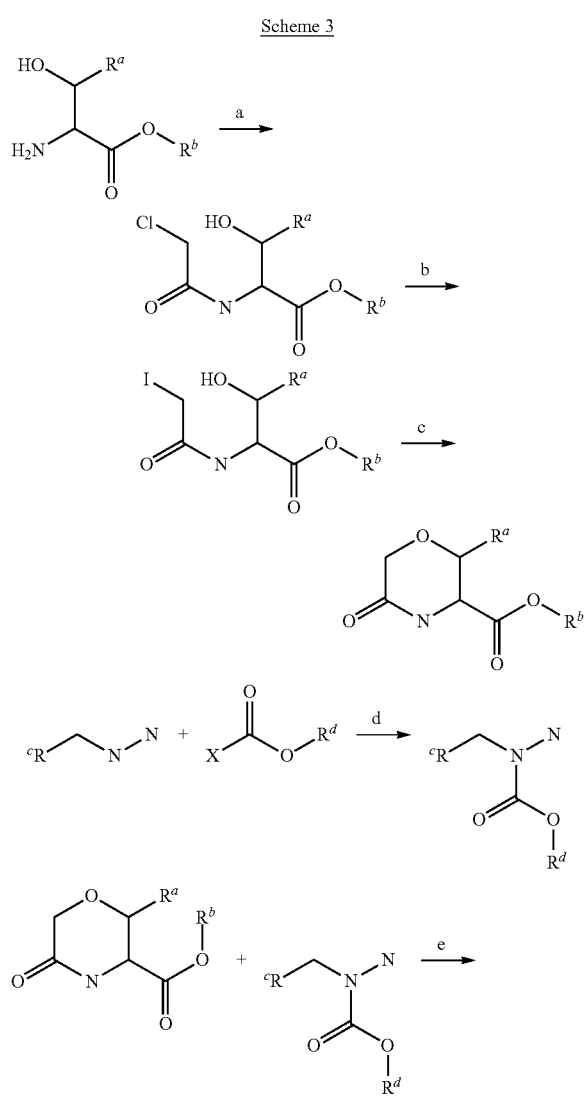

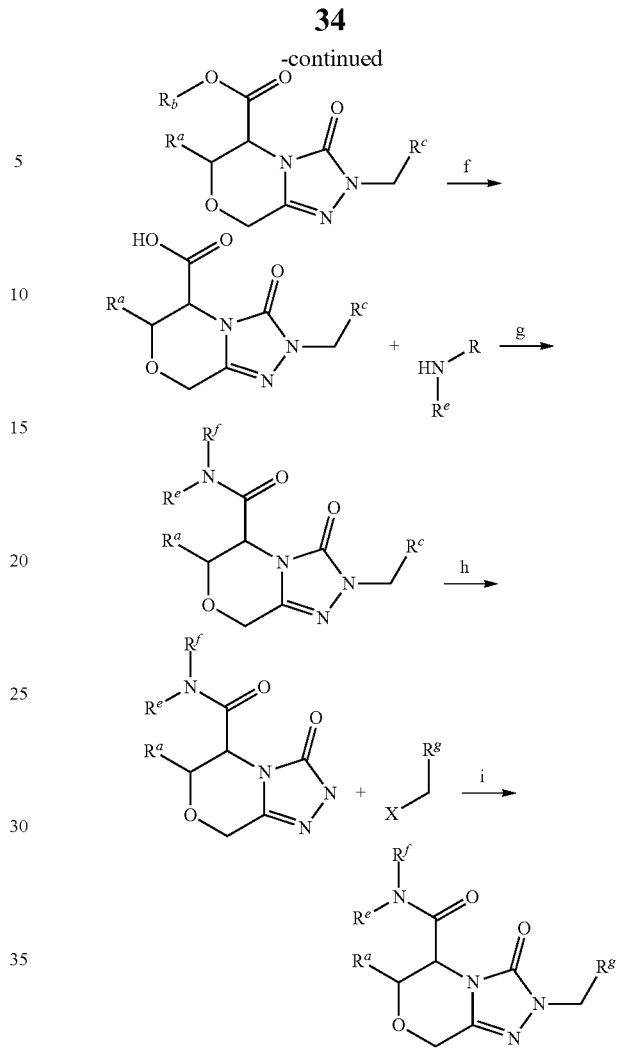

a) chloroacetyl chloride, triethylamine, THF, 0° C.;
b) sodium iodide, acetonitrile, RT;
c) silver(I)oxide, dichloromethane, RT, in the dark
d) triethylamine, dichloromethane, -78° C.,
e) trimethyloxonium tetrafluoroborate, dichloromethane, DMF, RT-150° C.;
f) lithium hydroxide, THF, RT;
g) diisopropylethylamine, THF, RT;
h) TFA, 150° C. microwave;
i) cesium carbonate, acetonitrile, RT The compounds of the invention have valuable pharmacological properties and can be used for prevention and treatment of diseases in humans and animals.

The compounds of the invention are potent, chemically stable inhibitors of human prolyl endopeptidase (PREP, PE, prolyl oligopeptidase, POP) and are therefore suitable for treatment and/or prevention of disorders and pathological processes, especially those in which PREP or the PREP product PGP (proline-glycine-proline) is involved in the course of an infectious or noninfectious inflammation event and/or tissue or vessel reconstruction.

In the context of the present invention, these especially include disorders of the respiratory pathway and the lung, such as chronic obstructive pulmonary disease (COPD), cystic fibrosis (mucoviscidosis, CF), asthma and the group of interstitial lung diseases (ILDs), and disorders of the cardiovascular system such as arteriosclerosis and myocarditis.

The forms of COPD especially include pulmonary emphysema induced by cigarette smoke, chronic bronchitis (CB), pulmonary hypertension in COPD (PH-COPD), bronchiectasis (BE) and combinations thereof, especially in acute exacerbating stages of the disease (AE-COPD).

The forms of asthma include asthmatic disorders of different severity with intermittent or persistent character, such as refractory asthma, bronchial asthma, allergic asthma, intrinsic asthma, extrinsic asthma and medicament- or dust-induced asthma.

The group of interstitial lung diseases (ILDs) includes idiopathic pulmonary fibrosis (IPF), pulmonary sarcoidosis and acute interstitial pneumonia, non-specific interstitial pneumonia, lymphoid interstitial pneumonia, respiratory bronchiolitis with interstitial pulmonary disorder, cryptogenic organizing pneumonia, desquamative interstitial pneumonia and non-classifiable idiopathic interstitial pneumonia, and also granulomatous interstitial pulmonary disorders, interstitial pulmonary disorders of known cause and other interstitial pulmonary disorders of unknown cause.

The compounds of the invention can also be used for treatment and/or prevention of further disorders of the respiratory pathways and of the lung, for example of pulmonary arterial hypertension (PAH) and other forms of pulmonary hypertension (PH), of bronchiolitis obliterans syndrome (BOS), of acute respiratory distress syndrome (ARDS), of acute lung damage (ALI), alpha-1 antitrypsin deficiency (AATD) and cystic fibrosis (CF), of various forms of bronchitis (chronic bronchitis, infectious bronchitis, eosinophilic bronchitis), of bronchiectasis, pneumonia, farmer's lung and related diseases, cough- and cold-type diseases having infectious and noninfectious causes (chronic inflammatory cough, iatrogenic cough), mucous membrane inflammation (including medicamentous rhinitis, vasomotor rhinitis and seasonally dependent allergic rhinitis, for example hay fever), and polyps.

The compounds of the invention can additionally be used for treatment and/or prevention of cardiovascular disorders such as, for example, high blood pressure (hypertension), heart failure, coronary heart disease, stable and unstable angina pectoris, renal hypertension, peripheral and cardial vascular disorders, arrhythmias, atrial and ventricular arrhythmias and impaired conduction such as, for example, atrioventricular blocks degrees I-III, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore for treatment and/or prevention of thromboembolic disorders and ischemias such as myocardial ischemia, myocardial infarction, stroke, cardiac hypertrophy, transient and ischemic attacks, preeclampsia, inflammatory cardiovascular disorders, spasms of the coronary arteries and peripheral arteries, edema formation such as, for example, pulmonary edema, cerebral edema, renal edema or edema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischemic cardiomyopathy, dilatative cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds of the invention are also suitable for treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis.

The present invention also encompasses the use of the compounds of the invention for treatment and/or prevention of sequelae of renal insufficiency, for example hypertension, pulmonary edema, heart failure, uremia, anemia, electrolyte disturbances (for example hyperkalemia, hyponatremia) and disturbances in bone and carbohydrate metabolism.

In addition, the compounds of the invention are suitable for treatment and/or prevention of disorders of the urogenital system, for example benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence, for example mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds of the invention can also be used for treatment of disorders of the female reproductive system, such as uterine myoma, endometriosis, dysmenorrhea and premature contractions. In addition, they are suitable for prophylaxis or treatment of hirsutism or hypertrichosis.

In addition, the compounds of the invention have antiinflammatory action and can therefore be used as antiinflammatory agents for treatment and/or prevention of sepsis (SIRS), multiple organ failure (MODS, MOF), inflammation disorders of the kidney, chronic intestinal inflammations (IBD, Crohn's disease, ulcerative colitis), pancreatitis, peritonitis, cystitis, urethritis, prostatitis, epidimytitis, oophoritis, salpingitis, vulvovaginitis, rheumatoid disorders, osteoarthritis, inflammation disorders of the central nervous system, multiple sclerosis, inflammatory skin disorders and eye inflammation disorders.

The compounds of the invention are also suitable for treatment and/or prevention of fibrotic disorders of the internal organs, for example the lung, the heart, the kidney, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphea, keloids, hypertrophic scarring, nevi, diabetic retinopathy, proliferative vitroretinopathy and disorders of the connective tissue (for example sarcoidosis). The compounds of the invention can likewise be used for promotion of wound healing, for controlling postoperative scarring, for example following glaucoma operations and cosmetically for aging or keratinized skin.

The compounds of the invention can also be used for treatment and/or prevention of anemias such as hemolytic anemias, in particular hemoglobinopathies such as sickle cell anemia and thalassemias, megaloblastic anemias, iron deficiency anemias, anemias owing to acute blood loss, displacement anemias and aplastic anemias.

Moreover, the compounds of the invention are suitable for treatment of cancers, for example skin cancer, brain tumors, breast cancer, bone marrow tumors, leukemias, liposarcomas, carcinomas of the gastrointestinal tract, of the liver, the pancreas, the lung, the kidney, the ureter, the prostate and the genital tract and also of malignant tumors of the lymphoproliferative system, for example Hodgkin's and non-Hodgkin's lymphoma.

In addition, the compounds of the invention can be used for treatment and/or prevention of arteriosclerosis, impaired lipid metabolism and dyslipidemias (hypolipoproteinemia, hypertriglyceridemias, hyperlipidemia, combined hyperlipidemias, hypercholesterolemia, abetalipoproteinemia, sitosterolemia), xanthomatosis, Tangier disease, adiposity, obesity, metabolic disorders (metabolic syndrome, hyperglycemia, insulin-dependent diabetes, non-insulin-dependent diabetes, gestation diabetes, hyperinsulinemia, insulin resistance, glucose intolerance and diabetic sequelae, such as retinopathy, nephropathy and neuropathy), of disorders of the gastrointestinal tract and the abdomen (glossitis, gingivitis, periodontitis, esophagitis, eosinophilic gastroenteritis, mastocytosis, Crohn's disease, colitis, proctitis, anus pruritis, diarrhea, celiac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, various forms of dermatitis, such as, for example, dermatitis abacribus, actinic dermatitis, allergic dermatitis, ammonia dermatitis, facticial dermatitis, autogenic dermatitis, atopic dermatitis, dermatitis calorica, dermatitis combustionis, dermatitis congelationis, dermatitis cosmetica, dermatitis escharotica, exfoliative dermatitis, dermatitis gangraenose, stasis dermatitis, dermatitis herpetiformis, lichenoid dermatitis, dermatitis inearis, dermatitis maligna, medicinal eruption dermatitis, dermatitis palmaris and plantaris, parasitic dermatitis, photoallergic contact dermatitis, phototoxic dermatitis, dermatitis pustularis, seborrheic dermatitis, sunburn, toxic dermatitis, Meleney's ulcer, dermatitis veneata, infectious dermatitis, pyrogenic dermatitis and perioral dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of eye inflammation diseases (saccoidosis, blepharitis, conjunctivitis, iritis, uveitis, chorioiditis, ophthalmitis), viral diseases (caused by influenza, adeno and corona viruses, such as, for example, HPV, HCMV, HIV, SARS), of disorders of the skeletal bone and the joints and also the skeletal muscle (multifarious forms of arthritis, such as, for example, arthritis alcaptonurica, arthritis ankylosans, arthritis dysenterica, arthritis exsudativa, arthritis fungosa, arthritis gonorrhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, hemophilic arthritis, juvenile chronic arthritis, rheumatoid arthritis and metastatic arthritis, furthermore Still syndrome, Felty syndrome, Sjörgen syndrome, Clutton syndrome, Poncet syndrome, Pott syndrome and Reiter syndrome, multifarious forms of arthropathies, such as, for example, arthropathia deformans, arthropathia neuropathica, arthropathia ovaripriva, arthropathia psoriatica and arthropathia tabica, systemic scleroses, multifarious forms of inflammatory myopathies, such as, for example, myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also the Gunther syndrome and the Munchmeyer syndrome), of inflammatory changes of the arteries (multifarious forms of arteritis, such as, for example, endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, such as, for example, cataract, cachexia, osteoporosis, gout, incontinence, lepra, Sezary syndrome and paraneoplastic syndrome, for rejection reactions after organ transplants and for wound healing and angiogenesis in particular in the case of chronic wounds.

Because of their profile of biochemical and pharmacological properties, the compounds of the invention are especially suitable for treatment and/or prevention of pulmonary inflammation disorders, particularly of chronic-obstructive pulmonary disease (COPD), of pulmonary emphysema, of chronic bronchitis, of bronchiectasis, of pulmonary hypertension in COPD (PH-COPD), of acute exacerbation in COPD, of cystic fibrosis (mucoviscidosis, CF), of asthma, and idiopathic pulmonary fibrosis (IPF), of bronchiolitis obliterans syndrome (BOS), of arteriosclerosis, of myocarditis, and of skin and eye inflammation disorders or inflammation disorders of the internal organs.

Because of their profile of biochemical and pharmacological properties, the compounds of the invention are very particularly suitable for treatment and/or prevention of pulmonary inflammation disorders, particularly of chronic-obstructive lung disease (COPD), of pulmonary emphysema, of chronic bronchitis, of bronchiectasis, of pulmonary hypertension in COPD (PH-COPD), of acute exacerbation in COPD, of cystic fibrosis (mucoviscidosis, CF), of asthma, and idiopathic pulmonary fibrosis (IPF) and of bronchiolitis obliterans syndrome (BOS).

The aforementioned well-characterized diseases in humans can also occur with comparable etiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a method of treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further active ingredients, especially for treatment and/or prevention of the aforementioned disorders.

Preferred examples of combination active ingredients suitable for this purpose include:
- organic nitrates and NO donors, for example sodium nitroprusside, nitroglycerin, isosorbide mononitrate, isosorbide dinitrate, molsidomine or SIN-1, and inhaled NO;
- compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;
- NO- and heme-independent activators of soluble guanylate cyclase (sGC), such as in particular the compounds described in WO 01/19355, WO 01/19776, WO 01/19778, WO 01/19780, WO 02/070462 and WO 02/070510;
- NO-independent but heme-dependent stimulators of soluble guanylate cyclase (sGC), such as in particular riociguat and the compounds described in WO 00/06568, WO 00/06569, WO 02/42301, WO 03/095451, WO 2011/147809, WO 2012/004258, WO 2012/028647 and WO 2012/059549;
- prostacyclin analogs and IP receptor agonists, by way of example and with preference iloprost, beraprost, treprostinil, epoprostenol or selexipag;
- endothelin receptor antagonists, by way of example and with preference bosentan, darusentan, ambrisentan or sitaxsentan;
- compounds which inhibit human neutrophile elastase (HNE), by way of example and with preference sivelestat or DX-890 (reltran);
- compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;
- compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);
- compounds which block the binding of serotonin to its receptors, by way of example and with preference antagonists of the 5-HT$_{2B}$ receptor such as PRX-08066;
- antagonists of growth factors, cytokines and chemokines, by way of example and with preference antagonists of TGF-β, CTGF, IL-1, IL-4, IL-5, IL-6, IL-8, IL-13 and integrins;
- Rho kinase-inhibiting compounds, by way of example and with preference fasudil, Y-27632, SLx-2119, BF-66851, BF-66852, BF-66853, KI-23095 or BA-1049;
- compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;
- compounds which influence the energy metabolism of the heart, by way of example and with preference etomoxir, dichloroacetate, ranolazine or trimetazidine;
- anti-obstructive agents as used, for example, for treatment of chronic obstructive pulmonary disease (COPD) or bronchial asthma, by way of example and with preference from the group of the inhalatively or systemically administered agonists of the 0-adrenergic receptor (0-mimetics) and the inhalatively administered anti-muscarinergic substances;

antiinflammatory, immunomodulating, immunosuppressive and/or cytotoxic agents, by way of example and with preference from the group of the systemically or inhalatively administered corticosteroids and also acetylcysteine, montelukast, azathioprine, cyclophosphamide, hydroxycarbamide, azithromycin, pirfenidone or etanercept;

antifibrotic agents, by way of example and with preference adenosine A2b receptor antagonists, sphingosine-1-phosphate receptor 3 (S1P3) antagonists, autotaxin inhibitors, lysophosphatidic acid receptor 1 (LPA-1) and lysophosphatidic acid receptor 2 (LPA-2) antagonists, lysyl oxidase (LOX) inhibitors, lysyl oxidase-like 2 inhibitors, CTGF inhibitors, IL-13 antagonists, $\alpha_v\beta_6$-integrin antagonists, TGF-$\beta$ antagonists, inhibitors of the Wnt signaling pathway or CCR2 antagonists;

antithrombotic agents, by way of example and with preference from the group of platelet aggregation inhibitors, the anticoagulants and the profibrinolytic substances;

hypotensive active compounds, by way of example and with preference from the group of the calcium antagonists, angiotensin AII antagonists, ACE inhibitors, vasopeptidase inhibitors, endothelin antagonists, renin inhibitors, $\alpha$-receptor blockers, $\beta$-receptor blockers, mineralocorticoid receptor antagonists and also the diuretics;

lipid metabolism modifiers, by way of example and with preference from the group of the thyroid receptor agonists, cholesterol synthesis inhibitors, by way of example and with preference HMG-CoA reductase or squalene synthesis inhibitors, of the ACAT inhibitors, CETP inhibitors, MTP inhibitors, PPAR-$\alpha$, PPAR-$\gamma$ and/or PPAR-$\delta$ agonists, cholesterol absorption inhibitors, lipase inhibitors, polymeric bile acid adsorbents, bile acid reabsorption inhibitors and lipoprotein(a) antagonists; and/or chemotherapeutics like those employed, for example, for the therapy of neoplasms in the lung or other organs.

In a preferred embodiment of the invention, the compounds of the invention are administered in combination with a $\beta$-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds of the invention are administered in combination with an antimuscarinergic substance, by way of example and with preference ipratropium bromide, tiotropium bromide or oxitropium bromide.

In a preferred embodiment of the invention, the compounds of the invention are administered in combination with a corticosteroid, by way of example and with preference prednisone, prednisolone, methylprednisolone, triamcinolone, dexamethasone, beclomethasone, betamethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, $\alpha$-receptor blockers, $\beta$-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an $\alpha_1$ receptor blocker, by way of example and with preference prazosin.

In a preferred embodiment of the invention, the compounds of the invention are administered in combination with a $\beta$ receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan, embursaran, irbesartan, olmesartan, eprosartan or azilsartan or a dual angiotensin AII antagonist/NEP inhibitor, for example and with preference LCZ696 (valsartan/sacubitril).

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-α, PPAR-γ and/or PPAR-δ agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-γ agonist, by way of example and with preference pioglitazone or rosiglitazone.

In a preferred embodiment of the invention, the compounds of the invention are administered in combination with a PPAR-δ agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, byway of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, byway of example and with preference gemcabene calcium (CI-1027) or nicotinic acid.

Particular preference is given to combinations of the compounds of the invention with one or more further active ingredients selected from the group consisting of PDE 5 inhibitors, sGC activators, sGC stimulators, prostacyclin analogs, IP receptor agonists, endothelin antagonists, compounds that inhibit the signal transduction cascade and pirfenidone.

The present invention further provides medicaments which comprise at least one compound of the invention, typically together with one or more inert, non-toxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally). Administration forms suitable for parenteral administration include inter alia preparations for injection and infusion in the form of solutions, suspensions, emulsions, lyophilizates or sterile powders.

For the other administration routes, suitable examples are inhalation medicaments (including powder inhalers, nebulizers, dosage aerosols), nasal drops, solutions or sprays; tablets for lingual, sublingual or buccal administration, films/oblates or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral and parenteral administration are preferred, especially oral, intravenous and intrapulmonary (inhalative) administration.

The compounds of the invention can be converted to the administration forms mentioned. This can be accomplished in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavor and/or odor correctors.

In general, it has been found to be advantageous in the case of parenteral administration to administer amounts of about 0.001 to 1 mg/kg, preferably about 0.01 to 0.5 mg/kg body weight to achieve effective results. In the case of oral administration the dosage is about 0.01 to 100 mg/kg, preferably about 0.01 to 20 mg/kg and most preferably 0.1 to 10 mg/kg body weight. In the case of intrapulmonary administration, the amount is generally about 0.1 to 50 mg per inhalation.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the aforementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

The present invention further provides medicaments pharmaceutical compositions which comprise at least one compound of the invention, typically together with one or more inert, non-toxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, nasal, sublingual, lingual, buccal, rectal, vaginal, dermal, transdermal, conjunctival or otic route, or as an implant or stent.

The compounds of the invention can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous, intravitreal or intraperitoneal route). Administration forms suitable for parenteral administration include inter alia preparations for injection and infusion in the form of solutions, suspensions, emulsions, lyophilizates or sterile powders.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, eye drops, eye ointments, eyewashes, ocular inserts, ear drops, sprays, powders, washes or tampons, vaginal capsules, aqueous suspensions (lotions, shaking mixtures), lipophilic suspensions, emulsions, microemulsions, ointments, creams, transdermal therapeutic systems (for example patches), milk, pastes, foams, dusting powders, implants or stents.

The compounds of the invention can be converted to the administration forms mentioned. This can be accomplished in a manner known per se by mixing with pharmaceutically suitable excipients. These excipients include fillers and carriers (for example cellulose, microcrystalline cellulose, for example Avicel®, lactose, mannitol, starch, calcium phosphates, for example Di-Cafos®), ointment bases (for example vaseline, paraffins, triglycerides, waxes, wool wax, wool wax alcohols, lanolin, hydrophilic ointment, polyethylene glycols), suppository bases (for example polyethylene glycols, cocoa butter, hard fat), solvents (e.g. water, ethanol, isopropanol, glycerol, propylene glycol, mid-chain triglycerides fatty oils, liquid polyethylene glycols, paraffins), surfactants, emulsifiers, dispersants or wetting agents (for example sodium dodecylsulfate, lecithin, phospholipids, fatty alcohols, for example Lanette®, sorbitan fatty acid esters, for example Span®, polyoxyethylene sorbitan fatty acid esters, for example Tween®, polyoxyethylene fatty acid glycerides, for example Cremophor®, polyoxyethylene fatty acid esters, polyoxyethylene fatty alcohol ethers, glycerol fatty acid esters, poloxamers, for example Pluronic®), buffer substances, and also acids and bases (for example phosphates, carbonates, citric acid, acetic acid, hydrochloric acid, sodium hydroxide, ammonium carbonate, trometamol, triethanolamine), isotonizing agents (for example glucose, sodium chloride), adsorbents (for example finely divided silicas), viscosity-increasing agents, gel formers, thickeners or binders (for example polyvinylpyrrolidone, methyl cellulose, hydroxypropyl methyl cellulose, hydroxypropyl cellulose, carboxymethyl cellulose-sodium, starch, carbomers, polyacrylic acids, for example Carbopol®, alginates, gelatins), disintegrants (for example modified starch, carboxymethyl cellulose-sodium, sodium starch glycolate, for example Explotab®, crosslinked polyvinylpyrrolidone, croscarmellose-sodium, for example AcDiSol®), flow regulators, lubricants, glidants and mold release agents (for example magnesium stearate, stearic acid, talc, finely divided silicas, for example Aerosil®), coating agents (for example sugar, shellac) and film formers for films or diffusion membranes with fast or modified dissolution (for example polyvinylpyrrolidones, for example Kollidon®, polyvinyl alcohol, hydroxypropyl methyl cellulose, hydroxypropyl cellulose, ethyl cellulose, hydroxypropyl methyl cellulose phthalate, cellulose acetate, cellulose acetate phthalate, polyacrylates, polymethacrylates, for example Eudragit®), capsule materials (e.g. gelatins, hydroxypropyl methyl cellulose), synthetic polymers (for example polylactides, polyglycolides, polyacrylates, polymethacrylates, for example Eudragit®, polyvinylpyrrolidones, for example Kollidon®, polyvinyl alcohols, polyvinyl acetate, polyethylene oxides, polyethylene glycols and the copolymers and block copolymers thereof), plasticizers (for example polyethylene glycols, propylene glycol, glycerol, triacetin, triacetyl citrate, dibutyl phthalate), penetration enhancers, stabilizers (e.g. antioxidants, for example ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), dyes (e.g. inorganic pigments, for example iron oxides, titanium dioxide), aromas, sweeteners, flavor and/or odor correctors.

Preference is given to oral or parenteral administration, especially oral administration.

The compounds of the invention can be converted to the administration forms mentioned. This can be accomplished in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavor and/or odor correctors.

In the case of parenteral administration, it has generally been found to be advantageous to administer amounts of about 0.1 to 6 mg/kg to achieve effective results. In the case of oral administration, the dose is about 0.1 to 10 mg/kg of body weight.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the aforementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for liquid/liquid solutions are based in each case on volume.

A. EXAMPLES

| Abbreviations and acronyms: | |
|---|---|
| Ac | acetyl |
| aq. | aqueous, aqueous solution |
| boc | tert-butoxycarbonyl |
| br.d | broad doublet |
| br.m | broad multiplet (NMR) |
| br.s | broad singlet (NMR) |
| br.t | broad triplet (NMR) |
| c | concentration |
| cat. | catalytic |
| d | doublet (NMR) |
| de | diastereomeric excess |
| TLC | thin layer chromatography |
| DCI | direct chemical ionization (in MS) |
| dd | doublet of doublets (NMR) |
| ddd | doublet of doublet of doublets (NMR) |
| dist. | distilled |
| DIAD | diisopropyl azodicarboxylate |
| DIEA | N,N-diisopropylethylamine |
| DMAP | 4-N,N-dimethylaminopyridine |
| DMF | dimethylformamide |
| DMSO | dimethyl sulfoxide |
| DSC | differential scanning calorimetry |
| dt | doublet of triplets (NMR) |
| EDC | N'-(3-dimethylaminopropyl)-N-ethylcarbodiimide hydrochloride |
| ee | enantiomeric excess |
| ent | enantiomerically pure, enantiomer |
| eq. | equivalent(s) |
| ESI | electrospray ionization (in MS) |
| Et | ethyl |
| GC-MS | gas chromatography-coupled mass spectrometry |
| h | hour(s) |
| HATU | O-(7-azabenzotriazol-1-yl)-N,N,N',N'-tetramethyluronium hexafluorophosphate |
| HBTU | O-(benzotriazol-1-yl)-N,N,N',N'-tetramethyluronium hexafluorophosphate |
| HOBt | 1-hydroxy-1H-benzotriazole hydrate |
| HPLC | high-pressure, high-performance liquid chromatography |
| ID | internal diameter |
| iPr | isopropyl |
| J | coupling constant (NMR) |
| conc. | concentrated |
| LC-MS | liquid chromatography-coupled mass spectrometry |
| m | multiplet (NMR) |
| Me | methyl |
| min | minute(s) |
| MPLC | medium-pressure liquid chromatography |
| MS | mass spectrometry |
| MTBE | methyl tert-butyl ether |
| NMR | nuclear magnetic resonance spectrometry |
| Pd/C | palladium on activated charcoal |
| Ph | phenyl |
| PyBOP | benzotriazol-1-yloxytris(pyrrolidino)phosphonium hexafluorophosphate |
| quant. | quantitative (in yield) |
| rac | racemic, racemate |
| RT | room temperature |
| Rt | retention time (in HPLC) |
| Schmp. | melting point |
| SFC | supercritical fluid chromatography |
| t | triplet (NMR) |
| tBu | tert-butyl |
| tert. | tertiary |
| TFA | trifluoroacetic acid |
| TFAA | trifluoroacetic anhydride |
| THF | tetrahydrofuran |

-continued

| Abbreviations and acronyms: | |
|---|---|
| TPPO | triphenylphosphine oxide |
| UV | ultraviolet spectrometry |
| cf. | see |
| v/v | volume to volume ratio (of a solution) |

HPLC, GC-MS and LC-MS Methods

Method 1:

Instrument: Waters ACQUITY SQD UPLC System; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 2:

MS instrument type: Thermo Scientific FT-MS; UHPLC+ instrument type: Thermo Scientific UltiMate 3000; column: Waters, HSST3, 2.1×75 mm, C18 1.8 μm; eluent A: 1 l of water+0.01% formic acid; eluent B: 1 l of acetonitrile+ 0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm Method 3:

Instrument: Agilent MS Quad 6150; HPLC: Agilent 1290; column: Waters Acquity UPLC HSS T3 1.8μ 50×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 4:

Instrument: Thermo DFS, Trace GC Ultra; column: Restek RTX-35, 15 m×200 μm×0.33 μm; constant flow rate of helium: 1.20 ml/min; oven: 60° C.; inlet: 220° C.; gradient: 60° C., 30° C./min→300° C. (hold for 3.33 min).

Further Details:

In the case of purifications of compounds of the invention by chromatography, particularly by column chromatography, prepacked silica gel cartridges, for example Biotage SNAP cartridges, KP-Sil® or KP-NH®, are used in combination with a Biotage system (SP4® or Isolera Four®).

Eluents employed are gradients of hexane/ethyl acetate or dichloromethane/methanol.

In the case of purifications of compounds of the invention by preparative HPLC by the above-described methods in which the eluents contain additives, for example trifluoroacetic acid, formic acid or ammonia, the compounds of the invention can be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

Furthermore, amidines can be present as free compounds or partially (depending on the preparation if acetic acid is involved) as acetate salts or acetate solvates.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x hydrochloric acid, "x $CF_3COOH$", "x $Na^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Furthermore, the secondary amides according to the invention may be present as rotational isomers/isomer mixtures, in particular in NMR studies. Purity figures are generally based on corresponding peak integrations in the LC/MS chromatogram, but may additionally also have been determined with the aid of the $^1$H NMR spectrum. If no purity is indicated, the purity is generally 100% according to automated peak integration in the LC/MS chromatogram, or the purity has not been determined explicitly.

Stated yields in % of theory are generally corrected for purity if a purity of <100% is indicated.

In solvent-containing or contaminated batches, the formal yield may be ">100%"; in these cases the yield is not corrected for solvent or purity.

In all $^1$H NMR spectra data, the chemical shifts δ[ppm] =are stated in ppm.

The multiplicities of proton signals in $^1$H NMR spectra reported in the paragraphs which follow represent the signal form observed in each case and do not take account of any higher-order signal phenomena. In general, the stated chemical shift refers to the center of the signal in question. In the case of broad multiplets, an interval is given. Signals obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet) or are not listed.

Melting points and melting ranges, if stated, are uncorrected.

The $^1$H NMR data of selected synthesis intermediates and working examples are stated in the form of $^1$H NMR peak lists. For each signal peak, first the δ[ppm]=value in ppm and then the signal intensity in round brackets are listed. The δ[ppm]=value/signal intensity number pairs for different signal peaks are listed with separation from one another by commas. The peak list for an example therefore takes the following form: δ[ppm]=$_1$ (intensity$_1$), δ[ppm]=$_2$ (intensity$_2$), . . . , δ[ppm]=$_i$ (intensity$_i$), . . . , δ[ppm]=$_n$ (intensity$_n$).

The intensity of sharp signals correlates with the height of the signals in a printed example of an NMR spectrum in cm and shows the true ratios of the signal intensities in comparison with other signals. In the case of broad signals, several peaks or the middle of the signal and the relative intensity thereof may be shown in comparison to the most intense signal in the spectrum. The lists of the $^1$H NMR peaks are similar to the conventional $^1$H NMR printouts and thus usually contain all peaks listed in a conventional NMR interpretation. In addition, like conventional $^1$H NMR printouts, they may show solvent signals, signals of stereoisomers of the target compounds which are likewise provided by the invention, and/or peaks of impurities. The peaks of stereoisomers of the target compounds and/or peaks of impurities usually have a lower intensity on average than the peaks of the target compounds (for example with a purity of >90%). Such stereoisomers and/or impurities may be typical of the particular preparation process. Their peaks can thus help in identifying reproduction of our preparation process with reference to "by-product fingerprints". An expert calculating the peaks of the target compounds by known methods (MestreC, ACD simulation, or using empirically evaluated expected values) can, if required, isolate the peaks of the target compounds, optionally using additional intensity filters. This isolation would be similar to the peak picking in question in conventional 1H NMR interpretation. A detailed description of the presentation of NMR data in the form of peak lists can be found in the publication "Citation of NMR Peaklist Data within Patent Applications" (cf. Research Disclosure Database Number 605005, 2014, Aug. 1, 2014 or http://www.researchdisclosure.com/searching-disclosures). In the peak picking routine described in Research Disclosure Database Number 605005, the parameter "MinimumHeight" can be set between 1% and 4%. Depending on the type of chemical structure and/or depending on the concentration of the compound to be analyzed, it may be advisable to set the parameters "MinimumHeight" to values of <1%.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

In the intermediates and working examples described hereinafter, a "5RS" identifier in the IUPAC name of the example in question, in conjunction with the term "racemate", means that this is a racemic mixture of the 5R enantiomer (→1st letter after the position number in "5RS") with the corresponding 5S enantiomers (→2nd letter after the position number). The "5RS" identifier in conjunction with the statements "enantiomer 1" and "enantiomer 2" means that these are the two enantiomers in separate, isolated form, without having undertaken an assignment of the absolute configuration (5R or 5S) to these enantiomers. Similar identifiers such as "5SR" that arise from the altered priority and/or sequence of named constituents owing to the IUPAC nomenclature rules should be interpreted in an analogous manner according to these instructions.

In the intermediates and working examples described hereinafter, a "5RS,7RS" identifier in the IUPAC name of the example in question, in conjunction with the term "racemate", means that this is a racemic mixture of the 5R,7R enantiomer (→1st letter in each case after the position number in "5RS,7RS") with the corresponding 5S,7S enantiomer (→2nd letter in each case after the position number). The "5RS,7RS" identifier in conjunction with the statements "enantiomer 1" and "enantiomer 2" means that these are the two enantiomers in separate, isolated form, without having undertaken an assignment of the absolute configuration (5R,7R or 5S,7S) to these enantiomers. Similar identifiers such as "5SR,7SR" that arise from the altered priority and/or sequence of named constituents owing to the IUPAC nomenclature rules should be interpreted in an analogous manner according to these instructions.

The (5S) configuration was assigned on the basis of crystal structure elucidation for Example 26, 108, 113, 157, 237, 358 and 454. In analogy, the (5S) configuration was assigned for examples 183-188, 190-219, 275-279, 342-402, 404-415, 418-563.

Starting Materials and Intermediates:

Intermediate 1

Methyl 3-fluoro-2-(trifluoromethyl)isonicotinate

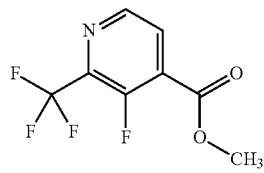

3-Fluoro-2-(trifluoromethyl)isonicotinic acid (1.00 g, 4.78 mmol) was dissolved in methanol (10 ml), and sulfuric acid (310 µl, 5.7 mmol) was added. The reaction mixture was heated to 60° C. for 30 minutes and then stirred at room temperature overnight. The reaction mixture was concentrated under reduced pressure and the residue was dissolved in ethyl acetate and washed with saturated sodium hydrogencarbonate solution. The organic phase was dried over sodium sulfate and filtered and the filtrate was concentrated. 890 mg (70% purity, 58% of theory) of the title compound were obtained.

LC-MS (Method 3): $R_t$=1.15 min; MS (ESIpos): m/z=224 $[M+H]^+$

Intermediate 2

[3-Fluoro-2-(trifluoromethyl)pyridin-4-yl]methanol

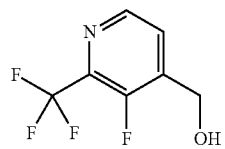

Methyl 3-fluoro-2-(trifluoromethyl)isonicotinate (890 mg, 70% purity, 3.99 mmol) was dissolved in methanol (5.0 ml), and sodium borohydride (166 mg, 4.39 mmol) was added in portions at 0° C. After stirring overnight, the reaction mixture was admixed at room temperature with saturated aqueous ammonium chloride solution and the methanol was removed under reduced pressure. The residue was admixed with ethyl acetate and water. The aqueous phase was extracted three times with ethyl acetate. The combined organic phases were dried over sodium sulfate and filtered, and the filtrate was concentrated. 420 mg (54% of theory) of the title compound were obtained. The compound was converted further directly.

Intermediate 3

4-(Chloromethyl)-3-fluoro-2-(trifluoromethyl)pyridine hydrochloride

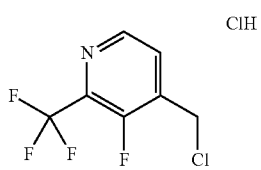 [SMILES: Cl ; Fc1c(CCl)ccnc1C(F)(F)F]

[3-Fluoro-2-(trifluoromethyl)pyridin-4-yl]methanol (420 mg, 2.15 mmol) was dissolved in dichloromethane (10 ml), and thionyl dichloride (310 µl, 4.3 mmol) was added at room temperature. After the reaction mixture had been stirred at room temperature overnight, thionyl dichloride (310 µl, 4.3 mmol) again and a drop of dimethylformamide were added. The reaction mixture was stirred at room temperature for one hour and then thionyl dichloride (620 µl, 8.6 mmol) and one drop of dimethylformamide were added again. After stirring at room temperature again for 2 hours, the solvent was removed under reduced pressure. 379 mg (70% of theory) of the title compound were obtained.

GC-MS (Method 4): $R_t$=2.74 min; MS (ESIpos): m/z=213 [M+H]$^+$

Intermediate 4

(6-Hydrazinopyrazin-2-yl)(pyrrolidin-1-yl)methanone

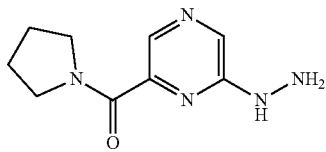 [SMILES: NNc1cncc(C(=O)N2CCCC2)n1]

A solution of (6-chloropyrazin-2-yl)(pyrrolidin-1-yl)methanone (710 mg, 3.35 mmol), hydrazine hydrate (1.6 ml, 34 mmol) and ethanol (7.1 ml) was stirred under reflux for 2 h. The solvent was removed under reduced pressure. The residue was taken up in saturated aqueous sodium hydrogencarbonate solution and then extracted with dichloromethane. The aqueous phase was saturated with sodium chloride and reextracted with dichloromethane and ethyl acetate. The organic phases were combined, dried over magnesium sulfate and concentrated under reduced pressure, and 275 mg (36% of theory) of the title compound were obtained.

$^1$H-NMR (400 MHz, DMSO-d6) δ [ppm]: 8.19-8.10 (m, 2H), 7.95 (s, 1H), 4.28 (s, 2H), 3.67-3.54 (m, 2H), 3.46 (t, 2H), 1.88-1.76 (m, 4H).

Intermediate 5

5-(Pyrrolidin-1-ylcarbonyl)[1,2,4]triazolo[4,3-a]pyrazin-3(2H)-one

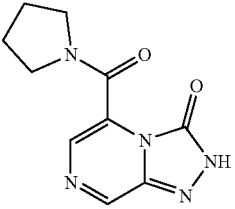 [SMILES: O=C(c1cncc2n[nH]c(=O)n12)N1CCCC1]

To an initial charge of (6-hydrazinopyrazin-2-yl)(pyrrolidin-1-yl)methanone (94.0 mg, 454 µmol) in THF (1.0 ml) was added di-1H-imidazol-1-ylmethanone (88.3 mg, 544 µmol), and the mixture was stirred at room temperature overnight. The solvent was removed under reduced pressure and the residue was purified via chromatography (silica gel, dichloromethane/methanol 90/10).

The product-containing fractions were concentrated under reduced pressure, and 83.5 mg (76% of theory) of the title compound were obtained.

$^1$H-NMR (400 MHz, DMSO-d6) δ [ppm]: 1.801 (2.45), 1.816 (4.36), 1.832 (4.48), 1.843 (4.50), 1.857 (5.35), 1.873 (5.56), 1.891 (3.10), 1.906 (0.80), 3.163 (2.40), 3.175 (2.34), 3.218 (0.57), 3.246 (4.88), 3.262 (10.52), 3.278 (5.58), 3.441 (5.00), 3.458 (8.29), 3.475 (4.14), 4.075 (0.53), 4.088 (0.53), 5.754 (1.55), 7.025 (0.48), 7.455 (16.00), 8.878 (13.88), 13.046 (1.65).

Intermediate 6 tert-Butyl (5RS)-3-oxo-5-(pyrrolidin-1-ylcarbonyl)-2,5,6,8-tetrahydro[1,2,4]triazolo[4,3-a]pyrazine-7(3H)-carboxylate (Racemate)

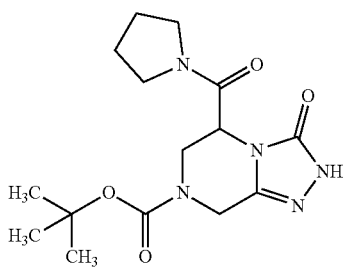 [SMILES: CC(C)(C)OC(=O)N1Cc2n[nH]c(=O)n2C(C(=O)N2CCCC2)C1]

To an initial charge of palladium on charcoal (200 mg, 10%) under argon was added 5-(pyrrolidin-1-ylcarbonyl)[1,2,4]triazolo[4,3-a]pyrazin-3(2H)-one (250 mg, 1.07 mmol) in 1,4-dioxane (15 ml). After addition of di-tert-butyl dicarbonate (250 µl, 1.1 mmol), the reaction mixture was stirred in a hydrogen atmosphere (3 bar) at room temperature overnight. The suspension was diluted with ethyl acetate and filtered through kieselguhr and washed through with dichloromethane/methanol 90/10. The reaction mixture was concentrated, and 351 mg (92% of theory) of the title compound were obtained.

LC-MS (Method 1): $R_t$=0.60 min; MS (ESIneg): m/z=336 [M−H]$^−$ $^1$H-NMR (400 MHz, DMSO-d6) δ [ppm]: 1.110 (0.50), 1.349 (7.03), 1.468 (16.00), 1.574 (1.67), 1.784 (0.62), 1.807 (0.48), 1.935 (0.71), 1.951 (0.79), 3.335 (0.50), 3.352 (0.42), 3.479 (0.41), 3.567 (1.03), 4.286 (0.42), 4.322 (0.41), 4.723 (0.75), 11.548 (1.35).

Intermediate 7 tert-Butyl (5RS)-3-oxo-5-(pyrrolidin-1-ylcarbonyl)-2,5,6,8-tetrahydro[1,2,4]triazolo[4,3-a]pyrazine-7(3H)-carboxylate (Enantiomer 1)

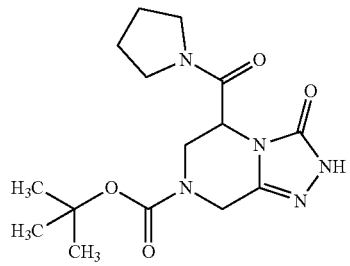 [SMILES: CC(C)(C)OC(=O)N1Cc2n[nH]c(=O)n2C(C(=O)N2CCCC2)C1]

tert-Butyl (5RS)-3-oxo-5-(pyrrolidin-1-ylcarbonyl)-2,5,6,8-tetrahydro[1,2,4]triazolo[4,3-a]pyrazine-7(3H)-carboxylate (racemate) was separated by chiral preparative liquid chromatography [sample preparation: 155 mg dissolved in 4 ml of ethanol and 2 ml of dichloromethane; injection volume: 0.3 ml; column: Daicel Chirapak® IF 5 μm, 250×20 mm; eluent: n-heptane/ethanol: isocratic 50% ethanol, flow rate: 15.0 ml/min; temperature 30° C.; UV detection: 220 nm]. After the separation, 47.0 mg of enantiomer 1, which eluted first, and 54.0 mg of enantiomer 2, which eluted later, were isolated.

Enantiomer 1:

Analytical chiral HPLC: $R_t$=6.84 min, e.e.=100% [column: Daicel Chiralpak® IF 5 μm 250×4.6 mm; eluent: n-heptane/ethanol 1.1; flow rate: 1 ml/min; UV detection: 220 nm]

LC-MS (Method 1): $R_t$=0.59 min; MS (ESIpos): m/z=338 [M+H]$^+$ $^1$H-NMR (400 MHz, DMSO-d6) δ [ppm]: −0.008 (0.64), 0.008 (0.52), 1.349 (16.00), 1.760 (0.54), 1.772 (0.81), 1.789 (1.09), 1.807 (0.92), 1.825 (0.65), 1.844 (0.61), 1.859 (0.56), 1.936 (1.59), 1.951 (1.69), 3.280 (0.68), 3.335 (0.49), 3.353 (0.64), 3.462 (0.81), 3.479 (0.92), 3.517 (0.65), 3.554 (0.52), 3.648 (0.84), 4.051 (0.60), 4.093 (0.70), 4.286 (0.97), 4.322 (0.93), 4.723 (1.73), 4.781 (0.68), 4.823 (0.58), 11.547 (2.68).

Intermediate 8 tert-Butyl (5RS)-3-oxo-5-(pyrrolidin-1-ylcarbonyl)-2,5,6,8-tetrahydro[1,2,4]triazolo[4,3-a]pyrazine-7(3H)-carboxylate (Enantiomer 2)

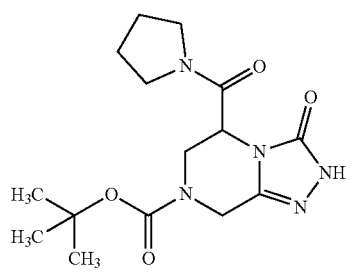 [SMILES: CC(C)(C)OC(=O)N1Cc2n[nH]c(=O)n2C(C(=O)N2CCCC2)C1]

tert-Butyl (5RS)-3-oxo-5-(pyrrolidin-1-ylcarbonyl)-2,5,6,8-tetrahydro[1,2,4]triazolo[4,3-a]pyrazine-7(3H)-carboxylate (racemate) was separated by chiral preparative liquid chromatography [sample preparation: 155 mg dissolved in 4 ml of ethanol and 2 ml of dichloromethane; injection volume: 0.3 ml; column: Daicel Chirapak® IF 5 μm, 250×20 mm; eluent: n-heptane/ethanol: isocratic 50% ethanol, flow rate: 15.0 ml/min; temperature 30° C.; UV detection: 220 nm]. After the separation, 47.0 mg of enantiomer 1, which eluted first, and 54.0 mg of enantiomer 2, which eluted later, were isolated.

Enantiomer 2:

Analytical chiral HPLC: $R_t$=10.28 min, e.e.=99% [column: Daicel Chiralpak® IF 5 μm 250×4.6 mm; eluent: n-heptane/ethanol 1.1; flow rate: 1 ml/min; UV detection: 220 nm]

LC-MS (Method 1): $R_t$=0.59 min; MS (ESIneg): m/z=336 [M−H]$^-$ $^1$H-NMR (400 MHz, DMSO-d6) δ [ppm]: 0.008 (0.93), 1.349 (16.00), 1.512 (0.94), 1.788 (1.33), 1.806 (0.99), 1.826 (0.73), 1.951 (1.74), 3.335 (0.96), 3.352 (0.82), 3.481 (0.94), 3.558 (0.52), 3.648 (0.86), 4.052 (0.59), 4.080 (0.62), 4.094 (0.72), 4.286 (0.98), 4.323 (0.92), 4.724 (1.70), 4.782 (0.71), 4.824 (0.58), 11.547 (1.12).

Intermediate 9

6-Chloropyrazine-2-carbonyl chloride

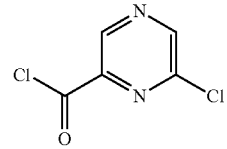

To an initial charge of thionyl chloride (23 ml, 320 mmol) was gradually added 6-chloropyrazine-2-carboxylic acid (5.00 g, 31.5 mmol). The reaction mixture was stirred at 90° C. for 2 hours. The volatile constituents were removed under reduced pressure and the residue was twice taken up in toluene and concentrated. The residue was directly reacted further without further purification.

Intermediate 10

(6-Chloropyrazin-2-yl)[(3S)-3-fluoropyrrolidin-1-yl]methanone

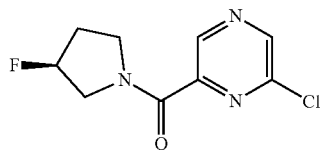 [SMILES: O=C(c1cncc(Cl)n1)N1CC[C@H](F)C1]

6-Chloropyrazine-2-carbonyl chloride (5.58 g, 31.5 mmol) was dissolved in dichloromethane (50 ml), and (3S)-3-fluoropyrrolidine hydrochloride (4.36 g, 34.7 mmol) was added. Subsequently, N,N-diisopropylethylamine (16 ml, 95 mmol) was added dropwise (exothermic). The reaction mixture was stirred at room temperature overnight and then diluted with water and dichloromethane. The phases were separated and the aqueous phase was extracted with dichloromethane. The combined organic phases were dried over magnesium sulfate and filtered, and the filtrate was concentrated. 6.68 g (92% of theory) of the title compound was obtained.

LC-MS (Method 2): $R_t$=1.11 min; MS (ESIpos): m/z=230 [M+H]$^+$ $^1$H-NMR (400 MHz, DMSO-d6) δ [ppm]: 1.250 (6.35), 1.263 (6.11), 2.004 (0.46), 2.012 (0.52), 2.019 (0.53), 2.028 (1.10), 2.040 (1.69), 2.049 (1.65), 2.055 (1.81), 2.064 (2.32), 2.077 (2.04), 2.091 (1.81), 2.100 (1.10), 2.107 (1.03), 2.116 (1.01), 2.126 (0.50), 2.148 (2.83), 2.153 (2.86), 2.170 (5.19), 2.184 (4.15), 2.196 (5.12), 2.219 (4.96), 2.234 (2.71), 2.252 (1.26), 2.270 (0.65), 3.124 (0.50), 3.542 (2.11), 3.561 (2.39), 3.572 (4.20), 3.590 (4.45), 3.600 (3.17), 3.619 (2.88), 3.663 (1.51), 3.672 (1.51), 3.700 (3.01), 3.708 (4.91), 3.726 (2.09), 3.736 (4.54), 3.753 (4.84), 3.767 (7.80), 3.780 (3.21), 3.797 (8.57), 3.804 (8.14), 3.827 (6.72), 3.851 (4.81), 3.877 (6.98), 3.886 (3.98), 3.900 (2.61), 3.914 (4.49), 3.948 (1.60), 3.978 (10.49), 5.317 (4.25), 5.322 (4.22), 5.330 (4.07), 5.338 (2.03), 5.452 (4.33), 5.463 (3.82), 8.947 (12.80), 8.953 (12.24), 8.983 (15.72), 8.986 (16.00).

Intermediate 11

[(3S)-3-Fluoropyrrolidin-1-yl](6-hydrazinopyrazin-2-yl)methanone

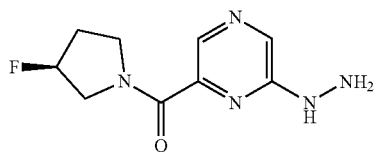 [SMILES: NNc1cncc(C(=O)N2CC[C@H](F)C2)n1]

A solution of (6-chloropyrazin-2-yl)[(3S)-3-fluoropyrrolidin-1-yl]methanone (1.00 g, 4.35 mmol) in THF (25 ml) was divided between 3 microwave vessels (30 ml) and hydrazine (11.7 ml, 1.0 M, 11.7 mmol) was added to each. The reaction mixtures were stirred under microwave irradiation at 100° C. for 4 hours. Solid sodium hydrogencarbonate and magnesium sulfate were added, and the mixture was stirred at room temperature for 5 minutes. The solids were filtered off and washed twice with ethyl acetate. The organic phase was concentrated. 934 mg (80% purity, 76% of theory) of the title compound was obtained.

$^1$H-NMR (400 MHz, DMSO-d6) δ [ppm]: −0.150 (0.46), −0.008 (3.67), 0.008 (3.57), 0.146 (0.49), 1.157 (4.10), 1.174 (8.20), 1.192 (4.19), 1.234 (0.41), 1.355 (8.09), 1.742 (0.51), 1.988 (16.00), 2.021 (1.24), 2.037 (0.90), 2.045 (1.26), 2.072 (0.67), 2.080 (0.83), 2.092 (0.98), 2.100 (0.74), 2.120 (2.18), 2.128 (2.38), 2.134 (2.10), 2.164 (2.87), 2.176 (2.97), 2.183 (3.61), 2.216 (1.02), 2.327 (0.51), 2.366 (0.44), 2.523 (1.60), 2.669 (0.54), 2.710 (0.48), 3.479 (1.09), 3.496 (1.23), 3.508 (2.12), 3.526 (2.19), 3.537 (1.49), 3.554 (1.35), 3.571 (0.47), 3.589 (0.52), 3.600 (1.19), 3.609 (0.88), 3.617 (0.46), 3.637 (1.53), 3.645 (1.62), 3.707 (2.75), 3.733 (3.25), 3.742 (3.02), 3.754 (3.60), 3.761 (2.67), 3.770 (3.87), 3.781 (3.95), 3.798 (3.26), 3.809 (2.20), 3.826 (2.13), 3.853 (1.93), 3.859 (2.39), 3.880 (3.03), 3.895 (1.94), 3.903 (2.59), 3.958 (2.37), 3.976 (1.22), 3.993 (2.77), 4.002 (2.97), 4.020 (6.05), 4.038 (3.75), 4.056 (1.85), 4.298 (11.88), 4.534 (0.64), 4.545 (0.64), 5.272 (1.94), 5.284 (1.33), 5.295 (1.95), 5.303 (1.20), 5.329 (0.45), 5.405 (1.89), 5.428 (1.86), 6.870 (0.71), 8.008 (8.72), 8.032 (8.87), 8.085 (0.91), 8.146 (10.29), 8.151 (10.35), 8.215 (4.30), 8.946 (1.40), 8.952 (1.37), 8.981 (1.65), 8.985 (1.72).

Intermediate 12

5-{[(3S)-3-Fluoropyrrolidin-1-yl]carbonyl}[1,2,4]triazolo[4,3-a]pyrazin-3(2H)-one

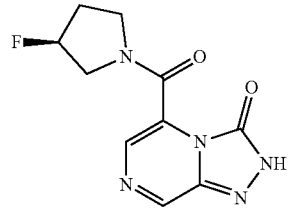 [SMILES: O=C(c1cncc2n[nH]c(=O)n12)N1CC[C@H](F)C1]

[(3S)-3-Fluoropyrrolidin-1-yl](6-hydrazinopyrazin-2-yl)methanone (930 mg, 80% purity, 3.30 mmol) was dissolved in THF (20 ml), and di-1H-imidazol-1-ylmethanone (562 mg, 3.47 mmol) was added. The reaction mixture was stirred at room temperature for 1 hour and at 50° C. for 15 minutes. The reaction mixture was concentrated and purified via column chromatography (silica gel, eluent: dichloromethane/methanol gradient). This gave 487 mg (56% of theory) of the title compound.

LC-MS (Method 1): $R_t$=0.25 min; MS (ESIpos): m/z=252 [M+H]$^+$ $^1$H-NMR (500 MHz, DMSO-d6) δ [ppm]: 1.168 (0.73), 2.037 (0.49), 2.058 (0.47), 2.093 (0.77), 2.105 (0.82), 2.132 (1.10), 2.142 (0.97), 2.175 (0.55), 2.191 (0.45), 2.216 (0.60), 2.227 (0.48), 3.385 (0.64), 3.400 (0.68), 3.483 (0.58), 3.504 (1.07), 3.519 (1.20), 3.541 (1.02), 3.640 (0.45), 3.647 (0.40), 3.669 (1.22), 3.676 (1.36), 3.684 (1.57), 3.733 (1.20), 3.743 (2.86), 3.752 (1.47), 3.773 (0.72), 5.260 (0.94), 5.365 (1.58), 5.469 (0.76), 5.752 (16.00), 7.480 (3.13), 7.505 (1.68), 8.893 (2.81), 8.900 (7.48), 13.038 (0.55).

Intermediate 13 tert-Butyl (5RS)-5-{[(3S)-3-fluoropyrrolidin-1-yl]carbonyl}-3-oxo-2,5,6,8-tetrahydro[1,2,4]triazolo[4,3-a]pyrazine-7(3H)-carboxylate (Diastereomer Mixture; 2 Isomers)

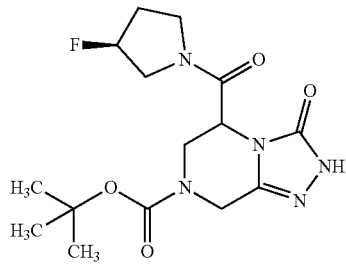 [SMILES: CC(C)(C)OC(=O)N1Cc2n[nH]c(=O)n2C(C(=O)N2CC[C@H](F)C2)C1]

To an initial charge of palladium on charcoal (357 mg, 10%) under argon was added 55-{[(3S)-3-fluoropyrrolidin-1-yl]carbonyl}[1,2,4]triazolo[4,3-a]pyrazin-3(2H)-one (480 mg, 1.91 mmol) in 1,4-dioxane (25 ml). After addition of di-tert-butyl dicarbonate (440 μl, 1.9 mmol), the reaction mixture was stirred in a hydrogen atmosphere (1 bar) at room temperature overnight. Palladium on charcoal (357 mg, 10%) was added, and the mixture was stirred again in a hydrogen atmosphere (1 bar) at room temperature for 20 hours. The suspension was diluted with ethyl acetate and filtered through kieselguhr and washed through with ethyl acetate. The reaction mixture was concentrated and purified via column chromatography (silica gel, eluent: dichloromethane/methanol gradient). This gave 486 mg (72% of theory) of the title compound.

LC-MS (Method 1): $R_f$=0.59 min; MS (ESIneg): m/z=354 [M–H]⁻

$^1$H-NMR (400 MHz, DMSO-d6) δ [ppm]: –0.008 (0.80), 0.008 (0.64), 1.343 (16.00), 2.120 (0.45), 2.150 (0.49), 2.229 (0.47), 2.245 (0.47), 2.278 (0.54), 2.523 (0.42), 3.455 (0.46), 3.499 (0.70), 3.529 (1.29), 3.563 (1.16), 3.627 (0.54), 3.661 (0.60), 3.787 (0.60), 3.797 (0.56), 3.867 (0.80), 3.995 (0.48), 4.048 (0.78), 4.069 (0.51), 4.090 (0.92), 4.258 (0.88), 4.294 (0.78), 4.306 (0.57), 4.323 (0.62), 4.342 (0.56), 4.359 (0.53), 4.640 (0.56), 4.723 (0.46), 4.784 (0.66), 4.828 (1.15), 4.851 (1.42), 4.858 (1.30), 5.396 (0.59), 5.529 (0.51), 5.753 (1.98), 11.574 (3.14). (mixture of diastereomers)

Intermediate 14

2-(4-Methylbenzyl)-5-(pyrrolidin-1-ylcarbonyl)[1,2,4]triazolo[4,3-a]pyrazin-3(2H)-one

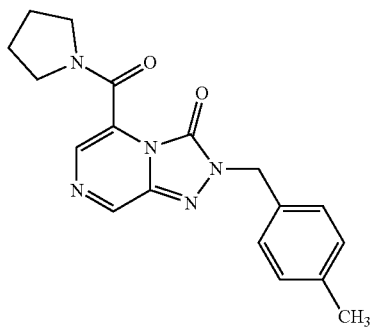 [SMILES: Cc1ccc(Cn2nc3cncc(C(=O)N4CCCC4)n3c2=O)cc1]

5-(Pyrrolidin-1-ylcarbonyl)[1,2,4]triazolo[4,3-a]pyrazin-3(2H)-one (50.0 mg, 214 μmol) was initially charged in acetonitrile (2.0 ml). Cesium carbonate (105 mg, 322 μmol) and 1-(bromomethyl)-4-methylbenzene (41.7 mg, 225 μmol) were subsequently added. After stirring overnight, the reaction mixture was admixed at room temperature with water and ethyl acetate. The organic phase was removed and the aqueous phase was extracted three times with ethyl acetate. The combined organic phases were washed with saturated aqueous sodium chloride solution, dried over magnesium sulfate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 36.6 mg (49% of theory) of the title compound were obtained.

LC-MS (Method 1): $R_f$=0.77 min; MS (ESIpos): m/z=338 [M+H]⁺

$^1$H-NMR (400 MHz, DMSO-d6) δ [ppm]: 1.806 (1.05), 1.821 (1.85), 1.837 (1.78), 1.851 (1.76), 1.866 (2.18), 1.882 (2.41), 1.900 (1.37), 2.276 (16.00), 2.326 (0.59), 3.269 (2.31), 3.285 (4.98), 3.302 (3.31), 3.311 (3.20), 3.452 (2.43), 3.469 (4.04), 3.486 (2.00), 5.081 (3.37), 7.149 (3.09), 7.169 (5.92), 7.209 (6.56), 7.229 (3.41), 7.524 (6.43), 8.890 (5.13).

Intermediate 15

5-{[(3S)-3-Fluoropyrrolidin-1-yl]carbonyl}-2-{[6-(trifluoromethyl)pyridin-3-yl]methyl}[1,2,4]triazolo[4,3-a]pyrazin-3(2H)-one

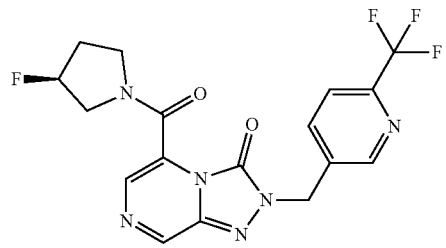 [SMILES: O=C(c1cncc2nn(Cc3ccc(C(F)(F)F)nc3)c(=O)n12)N1CC[C@H](F)C1]

5-{[(3S)-3-Fluoropyrrolidin-1-yl]carbonyl}[1,2,4]triazolo[4,3-a]pyrazin-3(2H)-one (90.0 mg, 358 μmol) was initially charged in acetonitrile (2.7 ml). Cesium carbonate (350 mg, 1.07 mmol) and 5-(chloromethyl)-2-(trifluoromethyl)pyridine hydrochloride (91.4 mg, 394 μmol) were subsequently added. After stirring overnight, the reaction mixture was concentrated under reduced pressure at room temperature. The residue was purified via preparative HPLC (Chromatorex C18, 10 μm, 125 mm×30 mm; eluent: acetonitrile/water gradient). The product-containing fractions were concentrated under reduced pressure, and 86.0 mg (59% of theory) of the title compound were obtained.

LC-MS (Method 2): $R_f$=1.25 min; MS (ESIpos): m/z=411 [M+H]⁺

$^1$H-NMR (400 MHz, DMSO-d6) δ [ppm]: –0.149 (0.83), –0.008 (6.09), 0.008 (5.53), 0.146 (0.74), 1.243 (0.83), 1.259 (0.83), 1.273 (0.51), 2.143 (0.78), 2.292 (0.74), 2.323 (1.52), 2.327 (2.07), 2.366 (1.80), 2.523 (5.07), 2.665 (1.48), 2.670 (2.03), 2.710 (1.57), 3.483 (16.00), 3.759 (2.21), 5.108 (0.55), 5.259 (0.78), 5.333 (5.35), 5.491 (0.41), 6.945 (6.27), 7.073 (6.69), 7.201 (6.27), 7.569 (1.98), 7.592 (0.92), 7.904 (2.58), 7.925 (3.37), 8.033 (1.57), 8.053 (1.06), 8.770 (1.98), 8.925 (1.52), 8.932 (2.90).

WORKING EXAMPLES

Example 1 tert-Butyl (5RS)-2-(4-methylbenzyl)-3-oxo-5-(pyrrolidin-1-ylcarbonyl)-2,5,6,8-tetrahydro[1,2,4]triazolo[4,3-a]pyrazine-7(3H)-carboxylate (Racemate)

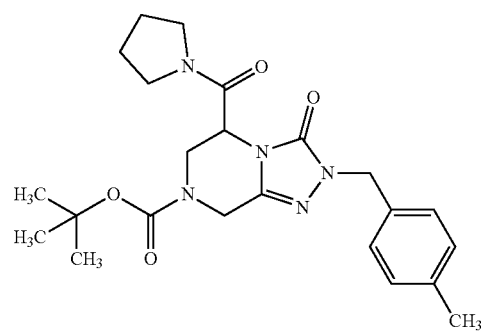 [SMILES: Cc1ccc(Cn2nc3n(c2=O)C(C(=O)N2CCCC2)CN(C(=O)OC(C)(C)C)C3)cc1]

To an initial charge of tert-butyl (5RS)-3-oxo-5-(pyrrolidin-1-ylcarbonyl)-2,5,6,8-tetrahydro[1,2,4]triazolo[4,3-a]pyrazine-7(3H)-carboxylate (racemate) (175 mg, 519 µmol) and cesium carbonate (254 mg, 778 µmol) in acetonitrile (5.0 ml) was subsequently added 1-(bromomethyl)-4-methylbenzene (101 mg, 545 µmol). After stirring at room temperature overnight, the reaction mixture was diluted with acetonitrile (5.0 ml) and stirred under reflux for 1 h. The reaction mixture was admixed with water and ethyl acetate. The organic phase was removed and the aqueous phase was extracted three times with ethyl acetate. The combined organic phases were washed with saturated aqueous sodium chloride solution, dried over magnesium sulfate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 122 mg (53% of theory) of the title compound were obtained.

LC-MS (Method 2): $R_t$=1.71 min; MS (ESIpos): m/z=442 [M+H]$^+$ $^1$H-NMR (400 MHz, DMSO-d6) δ [ppm]: −0.008 (0.42), 1.346 (11.49), 1.775 (0.44), 1.791 (0.58), 1.809 (0.48), 1.940 (0.93), 1.956 (0.98), 2.274 (11.81), 3.480 (0.55), 3.668 (0.48), 4.113 (0.41), 4.299 (0.56), 4.335 (0.53), 4.745 (0.41), 4.784 (3.68), 4.792 (3.75), 4.809 (1.22), 4.830 (0.64), 7.135 (16.00).

Example 2

(5RS)-2-(4-Methylbenzyl)-5-(pyrrolidin-1-ylcarbonyl)-5,6,7,8-tetrahydro[1,2,4]triazolo[4,3-a]pyrazin-3(2H)-one (Racemate)

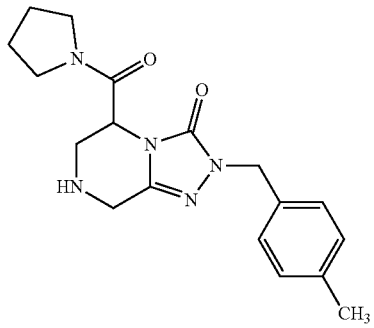 [SMILES: Cc1ccc(Cn2nc3n(c2=O)C(C(=O)N2CCCC2)CNC3)cc1]

To a solution of tert-butyl (5RS)-2-(4-methylbenzyl)-3-oxo-5-(pyrrolidin-1-ylcarbonyl)-2,5,6,8-tetrahydro[1,2,4]triazolo[4,3-a]pyrazine-7(3H)-carboxylate (racemate) (114 mg, 258 µmol) in dichloromethane (2.0 ml) at room temperature was added trifluoroacetic acid (1.0 ml). Once the reaction mixture had been stirred at room temperature for 30 min, dichloromethane was added and saturated aqueous sodium hydrogencarbonate solution was added. The phases were separated and the aqueous phase was extracted with dichloromethane. The combined organic phases were dried over magnesium sulfate and filtered, and the filtrate was concentrated. 86.0 mg (96% of theory) of the title compound were obtained.

LC-MS (Method 1): $R_t$=0.57 min; MS (ESIpos): m/z=342 [M+H]$^+$ $^1$H-NMR (400 MHz, DMSO-d6) δ [ppm]: −0.008 (0.41), 1.537 (0.43), 1.772 (1.31), 1.789 (2.29), 1.806 (1.76), 1.823 (0.52), 1.887 (0.53), 1.903 (1.57), 1.920 (1.96), 1.937 (1.18), 2.271 (10.88), 2.384 (0.60), 3.044 (0.65), 3.054 (0.66), 3.079 (0.94), 3.089 (0.93), 3.214 (0.86), 3.227 (0.95), 3.248 (0.73), 3.261 (1.15), 3.272 (0.76), 3.289 (1.31), 3.329 (0.73), 3.347 (1.23), 3.359 (0.45), 3.365 (0.65), 3.377 (0.66), 3.464 (0.78), 3.471 (0.58), 3.482 (0.48), 3.489 (0.97), 3.506 (0.43), 3.616 (0.48), 3.630 (1.22), 3.641 (0.53), 3.650 (0.58), 3.657 (0.82), 3.671 (2.59), 3.706 (2.47), 3.747 (0.82), 4.591 (0.88), 4.603 (1.51), 4.614 (0.85), 4.716 (0.45), 4.754 (3.17), 4.766 (3.13), 4.804 (0.45), 7.126 (16.00).

Example 3 tert-Butyl (5RS)-2-{[3-chloro-4-(trifluoromethyl)pyridin-2-yl]methyl}-5-{[(3S)-3-fluoropyrrolidin-1-yl]carbonyl}-3-oxo-2,5,6,8-tetrahydro[1,2,4]triazolo[4,3-a]pyrazine-7(3H)-carboxylate (Diastereomer Mixture; 2 Isomers)

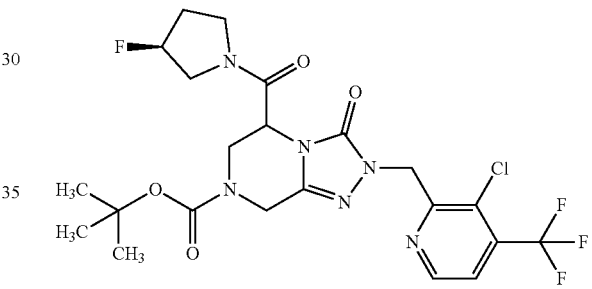

tert-Butyl (5RS)-5-{[(3S)-3-fluoropyrrolidin-1-yl]carbonyl}-3-oxo-2,5,6,8-tetrahydro[1,2,4]triazolo[4,3-a]pyrazine-7(3H)-carboxylate (diastereomer mixture; 2 isomers) (421 mg, 1.18 mmol) was initially charged in acetonitrile (10 ml). Cesium carbonate (965 mg, 2.96 mmol) and 3-chloro-2-(chloromethyl)-4-(trifluoromethyl)pyridine hydrochloride (434 mg, 80% purity, 1.30 mmol) were added. The reaction mixture was stirred at room temperature overnight. After 1 hour at 80° C., the residue was purified via preparative HPLC (Chromatorex C18, 10 µm, 125 mm×30 mm; eluent: acetonitrile/water gradient). The product-containing fractions were concentrated under reduced pressure, and 150 mg (92% purity, 21% of theory) of the title compound were obtained.

LC-MS (Method 3): $R_t$=1.20 min; MS (ESIpos): m/z=493 M−56$^+$ $^1$H-NMR (400 MHz, DMSO-d6) δ [ppm]: −0.008 (3.72), 0.008 (1.32), 1.344 (16.00), 1.399 (1.62), 1.477 (0.70), 2.155 (0.51), 2.249 (1.02), 2.284 (0.51), 2.327 (0.61), 2.366 (0.44), 2.519 (2.96), 2.524 (3.11), 3.073 (4.33), 3.530 (4.91), 3.585 (0.89), 3.624 (0.91), 3.803 (0.78), 3.879 (0.68), 4.088 (0.70), 4.129 (0.80), 4.271 (0.80), 4.308 (0.85), 4.355 (0.60), 4.763 (0.71), 4.828 (0.64), 4.852 (0.63), 4.977 (0.89), 4.985 (0.80), 5.146 (0.93), 5.152 (1.05), 5.187 (2.96), 5.192 (3.28), 5.214 (2.36), 5.218 (2.46), 5.226 (2.06), 5.259 (0.79), 5.267

(0.82), 5.404 (0.61), 5.477 (0.51), 5.534 (0.48), 7.854 (3.88), 7.867 (3.92), 7.883 (0.62), 8.740 (2.93), 8.752 (2.80), 8.771 (0.43). (mixture of diastereomers)

Example 4

(5RS)-2-{[3-Chloro-4-(trifluoromethyl)pyridin-2-yl]methyl}-5-{[(3S)-3-fluoropyrrolidin-1-yl]carbonyl}-5,6,7,8-tetrahydro[1,2,4]triazolo[4,3-a]pyrazin-3(2H)-one (Diastereomer Mixture; 2 Isomers)

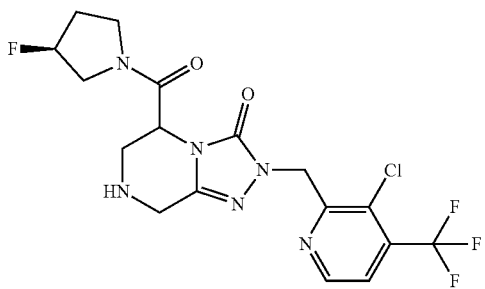 [SMILES: O=C(C1CNCc2nn(Cc3nccc(C(F)(F)F)c3Cl)c(=O)n21)N1CC[C@H](F)C1]

tert-Butyl (5RS)-2-{[3-chloro-4-(trifluoromethyl)pyridin-2-yl]methyl}-5-{[(3S)-3-fluoropyrrolidin-1-yl]carbonyl}-3-oxo-2,5,6,8-tetrahydro[1,2,4]triazolo[4,3-a]pyrazine-7(3H)-carboxylate (diastereomer mixture; 2 isomers) (143 mg, 92% purity, 240 µmol) was dissolved in dichloromethane (1.8 ml) and trifluoroacetic acid (900 µl), and stirred at room temperature for 30 minutes. The volatile constituents were removed under reduced pressure and the residue was purified via preparative HPLC (Chromatorex C18, 10 µm, 125 mm×30 mm; eluent: acetonitrile/water gradient). The product-containing fractions were concentrated under reduced pressure, and 99.6 mg (93% of theory) of the title compound were obtained.

LC-MS (Method 2): $R_t$=1.07 min; MS (ESIpos): m/z=449 [M+H]$^+$ $^1$H-NMR (400 MHz, DMSO-d6) δ [ppm]: −0.008 (3.04), 0.008 (2.76), 1.953 (0.79), 1.980 (0.88), 2.012 (0.44), 2.065 (0.84), 2.073 (1.06), 2.090 (2.39), 2.106 (2.04), 2.126 (1.84), 2.140 (2.29), 2.155 (1.71), 2.218 (2.00), 2.232 (1.82), 2.250 (2.15), 2.263 (2.20), 2.297 (0.69), 2.327 (0.89), 2.366 (0.95), 2.524 (2.07), 2.670 (0.69), 2.710 (0.63), 2.988 (1.09), 2.999 (1.12), 3.022 (1.35), 3.033 (1.37), 3.063 (1.47), 3.074 (2.44), 3.086 (2.48), 3.097 (2.60), 3.110 (3.12), 3.121 (3.40), 3.196 (1.76), 3.210 (1.94), 3.232 (1.52), 3.248 (2.72), 3.285 (6.60), 3.355 (3.62), 3.373 (2.95), 3.383 (2.15), 3.401 (1.31), 3.408 (1.36), 3.417 (1.24), 3.480 (1.14), 3.509 (2.07), 3.516 (2.14), 3.540 (1.96), 3.550 (1.67), 3.564 (1.39), 3.574 (3.17), 3.589 (1.95), 3.607 (4.76), 3.636 (2.65), 3.647 (4.32), 3.659 (2.95), 3.678 (8.56), 3.688 (11.87), 3.714 (11.37), 3.720 (10.26), 3.744 (2.34), 3.756 (2.95), 3.763 (4.15), 3.792 (1.11), 3.803 (1.15), 3.813 (1.86), 3.823 (1.87), 3.898 (2.84), 3.950 (1.22), 3.970 (2.61), 3.996 (1.85), 4.026 (1.14), 4.057 (0.85), 4.578 (1.39), 4.591 (2.66), 4.603 (1.36), 4.637 (1.85), 4.649 (3.21), 4.661 (1.84), 4.671 (1.75), 4.683 (2.72), 4.694 (1.66), 4.714 (1.76), 4.726 (3.15), 4.737 (1.69), 5.122 (3.17), 5.128 (2.79), 5.163 (12.90), 5.169 (14.29), 5.181 (12.67), 5.190 (12.97), 5.222 (2.29), 5.230 (3.41), 5.262 (2.27), 5.271 (2.17), 5.345 (1.45), 5.396 (2.22), 5.477 (1.35), 5.510 (1.02), 7.844 (15.37), 7.856 (16.00), 8.347 (0.56), 8.736 (11.56), 8.748 (11.27). (mixture of diastereomers)

Example 5 tert-Butyl (5RS)-5-{[(3S)-3-fluoropyrrolidin-1-yl]carbonyl}-2-[4-fluoro-3-(trifluoromethyl)benzyl]-3-oxo-2,5,6,8-tetrahydro[1,2,4]triazolo[4,3-a]pyrazine-7(3H)-carboxylate (Diastereomer Mixture; 2 Isomers)

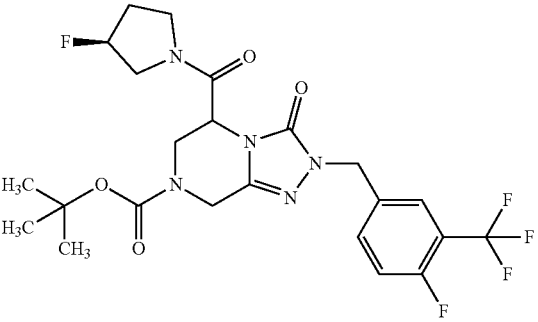 [SMILES: CC(C)(C)OC(=O)N1Cc2nn(Cc3ccc(F)c(C(F)(F)F)c3)c(=O)n2C(C(=O)N2CC[C@H](F)C2)C1]

To a suspension of tert-butyl (5RS)-5-{[(3S)-3-fluoropyrrolidin-1-yl]carbonyl}-3-oxo-2,5,6,8-tetrahydro[1,2,4]triazolo[4,3-a]pyrazine-7(3H)-carboxylate (diastereomer mixture; 2 isomers) (421 mg, 1.18 mmol) and cesium carbonate (965 mg, 2.96 mmol) in acetonitrile (10 ml) was added 4-(bromomethyl)-1-fluoro-2-(trifluoromethyl)benzene (335 mg, 1.30 mmol). The reaction mixture was stirred at room temperature overnight and then diluted with ethyl acetate. The organic phase was washed with water. The aqueous phase then was extracted with ethyl acetate. The combined organic phases were dried over magnesium sulfate and filtered, and the filtrate was concentrated. 608 mg (92% of theory) of the title compound were obtained.

LC-MS (Method 2): $R_t$=1.84 min; MS (ESIpos): m/z=476 [M+H]$^+$ $^1$H-NMR (400 MHz, DMSO-d6) δ [ppm]: 0.808 (0.43), 0.824 (0.42), 0.833 (0.58), 0.840 (0.97), 0.854 (0.59), 1.106 (4.99), 1.343 (16.00), 1.423 (1.13), 1.514 (3.80), 2.126 (0.41), 2.156 (0.43), 2.235 (0.42), 2.283 (0.48), 3.077 (1.57), 3.453 (0.42), 3.557 (0.85), 3.577 (0.82), 3.613 (0.79), 3.646 (0.57), 3.683 (0.56), 3.806 (0.80), 3.881 (0.48), 4.021 (0.41), 4.085 (0.62), 4.128 (0.76), 4.283 (0.68), 4.320 (0.63), 4.353 (0.49), 4.368 (0.52), 4.389 (0.40), 4.743 (0.48), 4.795 (0.85), 4.835 (0.78), 4.963 (6.80), 5.405 (0.55), 5.535 (0.43), 7.490 (1.02), 7.512 (1.86), 7.538 (1.65), 7.599 (1.19), 7.697 (1.49), 7.713 (1.49). (mixture of diastereomers)

Example 6

(5RS)-5-{[(3S)-3-Fluoropyrrolidin-1-yl]carbonyl}-2-[4-fluoro-3-(trifluoromethyl)benzyl]-5,6,7,8-tetrahydro[1,2,4]triazolo[4,3-a]pyrazin-3(2H)-one (Diastereomer Mixture; 2 Isomers)

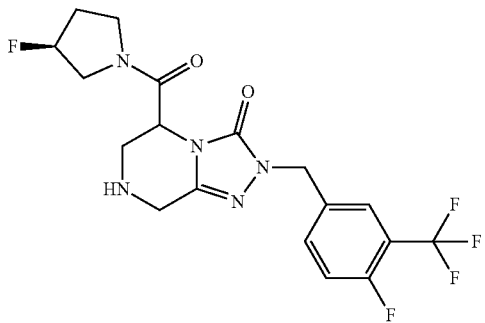 [SMILES: O=C(C1CNCc2nn(Cc3ccc(F)c(C(F)(F)F)c3)c(=O)n21)N1CC[C@H](F)C1]

To a solution of tert-butyl (5RS)-5-{[(3S)-3-fluoropyrrolidin-1-yl]carbonyl}-2-[4-fluoro-3-(trifluoromethyl)benzyl]-3-oxo-2,5,6,8-tetrahydro[1,2,4]triazolo[4,3-a]pyrazine-7(3H)-carboxylate (diastereomer mixture; 2 isomers) (600 mg, 95% purity, 1.07 mmol) in dichloromethane (8.0 ml) was added trifluoroacetic acid (4.0 ml). The reaction mixture was stirred at room temperature for 30 minutes. Subsequently, all volatile constituents were removed under reduced pressure and the residue was purified via preparative HPLC (Chromatorex C18, 10 μm, 125 mm×30 mm; eluent: acetonitrile/water gradient). The product-containing fractions were concentrated under reduced pressure, and 355 mg (77% of theory) of the title compound were obtained.

LC-MS (Method 2): $R_t$=1.23 min; MS (ESIpos): m/z=432 [M+H]$^+$ $^1$H-NMR (400 MHz, DMSO-d6) δ [ppm]: −0.008 (2.40), 0.008 (1.89), 1.958 (0.49), 1.984 (0.56), 2.064 (0.57), 2.073 (0.75), 2.093 (1.37), 2.115 (1.11), 2.129 (1.07), 2.142 (1.25), 2.155 (0.96), 2.198 (0.89), 2.218 (1.05), 2.234 (1.12), 2.248 (1.28), 2.263 (1.23), 2.328 (0.64), 2.366 (0.56), 2.523 (1.76), 2.670 (0.59), 2.710 (0.44), 2.997 (0.57), 3.008 (0.59), 3.033 (0.70), 3.043 (0.71), 3.084 (0.90), 3.095 (1.43), 3.107 (1.22), 3.119 (1.39), 3.130 (2.17), 3.142 (1.91), 3.187 (1.24), 3.199 (1.36), 3.221 (0.90), 3.238 (1.60), 3.252 (1.73), 3.266 (2.51), 3.279 (3.79), 3.351 (1.93), 3.362 (1.82), 3.379 (1.60), 3.391 (0.98), 3.409 (0.98), 3.466 (0.50), 3.475 (0.54), 3.502 (0.69), 3.514 (1.15), 3.523 (1.19), 3.534 (1.66), 3.552 (0.85), 3.568 (1.56), 3.604 (2.80), 3.625 (0.54), 3.643 (2.29), 3.651 (3.11), 3.684 (4.29), 3.695 (6.56), 3.726 (5.31), 3.733 (6.32), 3.760 (1.67), 3.768 (2.19), 3.774 (2.43), 3.792 (0.73), 3.802 (1.06), 3.811 (1.30), 3.884 (1.28), 3.937 (0.73), 3.959 (1.85), 3.985 (0.77), 4.019 (0.69), 4.051 (0.53), 4.570 (0.66), 4.582 (1.15), 4.594 (0.65), 4.630 (0.94), 4.642 (1.45), 4.653 (0.88), 4.680 (1.03), 4.692 (1.59), 4.702 (1.01), 4.719 (1.07), 4.731 (1.73), 4.742 (1.03), 4.930 (16.00), 5.264 (1.20), 5.272 (1.21), 5.345 (0.84), 5.403 (1.23), 5.476 (0.82), 5.511 (0.50), 7.481 (2.52), 7.504 (4.42), 7.530 (4.05), 7.579 (2.54), 7.585 (2.66), 7.592 (2.96), 7.606 (1.73), 7.612 (1.62), 7.683 (3.32), 7.699 (3.31), 8.217 (0.49). (mixture of diastereomers)

Example 7

(5RS)-5-{[(3S)-3-Fluoropyrrolidin-1-yl]carbonyl}-2-[4-fluoro-3-(trifluoromethyl)benzyl]-5,6,7,8-tetrahydro[1,2,4]triazolo[4,3-a]pyrazin-3(2H)-one (Isomer 1)

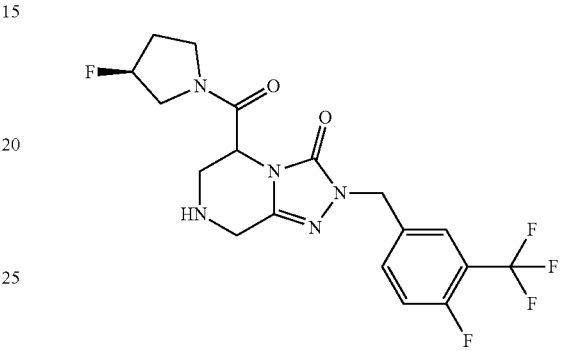

(5RS)-5-{[(3S)-3-Fluoropyrrolidin-1-yl]carbonyl}-2-[4-fluoro-3-(trifluoromethyl)benzyl]-5,6,7,8-tetrahydro[1,2,4]triazolo[4,3-a]pyrazin-3(2H)-one (diastereomer mixture; 2 isomers) was separated by chiral preparative liquid chromatography [sample preparation: 340 mg dissolved in 5 ml of ethanol; injection volume: 0.25 ml; column: Daicel Chirapak® IE 5 μm, 250×20 mm; eluent: n-heptane/ethanol: isocratic 40% ethanol, flow rate: 20.0 ml/min; temperature 40° C.; UV detection: 210 nm]. After the separation, 121 mg of isomer 1, which eluted first, and 165 mg of isomer 2, which eluted later, were isolated.

Isomer 1:

Analytical chiral HPLC: $R_t$=2.24 min, d.e.=100% [column: Daicel Chiralpak® IF-3 3 μm 50×4.6 mm; eluent: n-heptane/ethanol 1:1; flow rate: 1 ml/min; UV detection: 220 nm]

LC-MS (Method 2): $R_t$=1.24 min; MS (ESIpos): m/z=432 [M+H]$^+$ $^1$H-NMR (400 MHz, DMSO-d6) δ [ppm]: −0.008 (1.93), 0.008 (1.10), 1.038 (0.72), 1.046 (0.44), 1.056 (1.35), 1.064 (0.80), 1.073 (0.72), 1.082 (0.42), 1.959 (0.42), 1.983 (0.47), 2.063 (0.47), 2.073 (0.55), 2.091 (1.08), 2.107 (1.12), 2.139 (1.23), 2.157 (0.87), 2.213 (1.02), 2.234 (1.16), 2.263 (1.40), 2.328 (1.33), 2.366 (1.10), 2.519 (2.24), 2.524 (2.10), 2.670 (0.47), 2.710 (0.44), 3.003 (0.78), 3.038 (0.95), 3.100 (1.02), 3.136 (1.40), 3.280 (3.75), 3.354 (0.99), 3.368 (0.89), 3.377 (0.95), 3.404 (1.02), 3.412 (0.99), 3.426 (0.44), 3.438 (0.53), 3.456 (0.47), 3.466 (0.78), 3.474 (0.80), 3.501 (1.08), 3.510 (0.95), 3.626 (0.99), 3.650 (4.00), 3.668 (2.58), 3.680 (4.63), 3.685 (4.51), 3.705 (4.19), 3.733 (4.11), 3.759 (2.69), 3.780 (1.54), 3.811 (2.48), 3.884 (2.58), 4.337 (0.40), 4.570 (1.46), 4.582 (2.33), 4.594 (1.35), 4.631 (1.97), 4.641 (2.88), 4.653

(1.76), 4.888 (0.57), 4.927 (16.00), 4.968 (0.57), 5.263 (1.46), 5.388 (1.48), 5.394 (1.52), 5.511 (0.99), 7.481 (2.48), 7.503 (4.19), 7.529 (3.77), 7.579 (2.46), 7.585 (2.60), 7.591 (2.77), 7.606 (1.65), 7.612 (1.48), 7.677 (3.56), 7.695 (3.47).

Example 8

(5RS)-5-{[(3S)-3-Fluoropyrrolidin-1-yl]carbonyl}-2-[4-fluoro-3-(trifluoromethyl)benzyl]-5,6,7,8-tetrahydro[1,2,4]triazolo[4,3-a]pyrazin-3(2H)-one (Isomer 2)

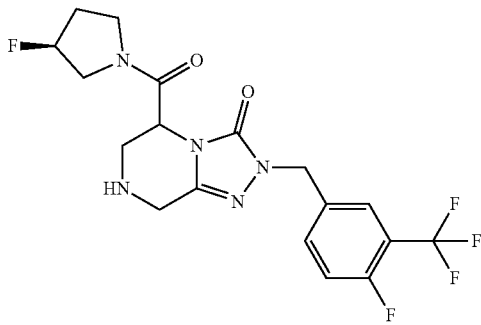 [SMILES: O=C(C1CNCc2nn(Cc3ccc(F)c(C(F)(F)F)c3)c(=O)n21)N1CC[C@H](F)C1]

(5RS)-5-{[(3S)-3-Fluoropyrrolidin-1-yl]carbonyl}-2-[4-fluoro-3-(trifluoromethyl)benzyl]-5,6,7,8-tetrahydro[1,2,4]triazolo[4,3-a]pyrazin-3(2H)-one (diastereomer mixture; 2 isomers) was separated by chiral preparative liquid chromatography [sample preparation: 340 mg dissolved in 5 ml of ethanol; injection volume: 0.25 ml; column: Daicel Chirapak® IE 5 µm, 250×20 mm; eluent: n-heptane/ethanol: isocratic 40% ethanol, flow rate: 20.0 ml/min; temperature 40° C.; UV detection: 210 nm]. After the separation, 121 mg of isomer 1, which eluted first, and 165 mg of isomer 2, which eluted later, were isolated.

Enantiomer 2:

Analytical chiral HPLC: $R_t$=4.20 min, d.e.=100% [column: Daicel Chiralpak® IF-3 3 µm 50×4.6 mm; eluent: n-heptane/ethanol 1:1; flow rate: 1 ml/min; UV detection: 220 nm]

LC-MS (Method 2): $R_t$=1.24 min; MS (ESIpos): m/z=432 [M+H]$^+$ $^1$H-NMR (400 MHz, DMSO-d6) δ [ppm]: −0.008 (0.87), 0.008 (0.68), 1.113 (0.70), 1.958 (0.40), 1.984 (0.46), 2.065 (0.51), 2.093 (1.29), 2.116 (1.04), 2.126 (0.93), 2.144 (1.01), 2.198 (1.01), 2.219 (0.87), 2.234 (0.80), 2.248 (1.18), 2.328 (0.68), 2.333 (0.66), 2.366 (0.70), 2.432 (0.76), 2.519 (1.10), 2.524 (0.87), 3.100 (0.97), 3.135 (1.75), 3.193 (1.02), 3.232 (0.99), 3.244 (1.18), 3.260 (0.84), 3.281 (0.87), 3.352 (1.01), 3.363 (1.56), 3.380 (1.50), 3.391 (0.99), 3.409 (0.78), 3.515 (1.40), 3.523 (1.63), 3.534 (2.35), 3.552 (1.14), 3.563 (2.14), 3.568 (2.22), 3.574 (1.88), 3.588 (1.18), 3.605 (3.95), 3.647 (0.93), 3.663 (1.06), 3.693 (2.68), 3.703 (2.24), 3.732 (3.19), 3.770 (1.50), 3.792 (0.87), 3.800 (0.78), 3.937 (1.02), 3.959 (2.68), 3.986 (1.12), 4.018 (0.97), 4.050 (0.78), 4.680 (1.46), 4.692 (2.26), 4.702 (1.44), 4.720 (1.56), 4.731 (2.47), 4.742 (1.48), 4.932 (16.00), 4.970 (0.53), 5.273 (1.25), 5.344 (1.20), 5.403 (1.21), 5.476 (1.18), 7.482 (2.01), 7.504 (3.59), 7.530 (3.23), 7.579 (2.13), 7.585 (2.26), 7.592 (2.51), 7.606 (1.46), 7.613 (1.37), 7.684 (3.09), 7.701 (3.15).

Example 9 tert-Butyl (5RS)-5-{[(3S)-3-fluoropyrrolidin-1-yl]carbonyl}-2-(4-methylbenzyl)-3-oxo-2,5,6,8-tetrahydro[1,2,4]triazolo[4,3-a]pyrazine-7(3H)-carboxylate (Diastereomer Mixture; 2 Isomers)

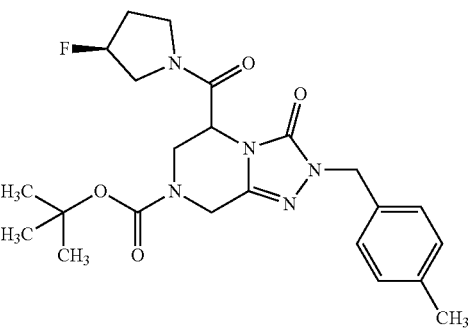 [SMILES: Cc1ccc(Cn2nc3n(c2=O)C(C(=O)N2CC[C@H](F)C2)CN(C(=O)OC(C)(C)C)C3)cc1]

To a suspension of tert-butyl (5RS)-5-{[(3S)-3-fluoropyrrolidin-1-yl]carbonyl}-3-oxo-2,5,6,8-tetrahydro[1,2,4]triazolo[4,3-a]pyrazine-7(3H)-carboxylate (diastereomer mixture; 2 isomers) (200 mg, 563 µmol) and cesium carbonate (275 mg, 844 µmol) in acetonitrile (5.0 ml) was added 1-(bromomethyl)-4-methylbenzene (109 mg, 591 µmol). The reaction mixture was stirred at room temperature for 4.5 hours, and then diluted with ethyl acetate. The organic phase was washed with water. The aqueous phase then was extracted with ethyl acetate. The combined organic phases were dried over magnesium sulfate and filtered, and the filtrate was concentrated. 246 mg (91% of theory) of the title compound were obtained.

LC-MS (Method 1): $R_t$=0.91 min; MS (ESIpos): m/z=460 [M+H]$^+$ $^1$H-NMR (500 MHz, DMSO-d6) δ [ppm]: 1.160 (0.62), 1.174 (1.24), 1.188 (0.64), 1.340 (11.14), 1.987 (2.36), 2.244 (0.48), 2.274 (16.00), 2.294 (1.51), 2.299 (1.12), 3.498 (0.41), 3.523 (0.46), 3.565 (0.70), 3.599 (0.61), 3.808 (0.60), 3.868 (0.42), 4.022 (0.73), 4.036 (0.70), 4.071 (0.54), 4.105 (0.64), 4.272 (0.62), 4.301 (0.51), 4.320 (0.41), 4.349 (0.46), 4.673 (0.79), 4.751 (0.47), 4.762 (0.43), 4.783 (2.41), 4.793 (4.44), 4.797 (4.00), 4.823 (0.70), 4.829 (0.70), 4.923 (0.48), 4.929 (0.54), 4.940 (0.82), 4.946 (0.75), 5.414 (0.55), 7.135 (12.68), 7.139 (9.65). (mixture of diastereomers)

Example 10

(5RS)-5-{[(3S)-3-Fluoropyrrolidin-1-yl]carbonyl}-2-(4-methylbenzyl)-5,6,7,8-tetrahydro[1,2,4]triazolo[4,3-a]pyrazin-3(2H)-one (Diastereomer Mixture; 2 Isomers)

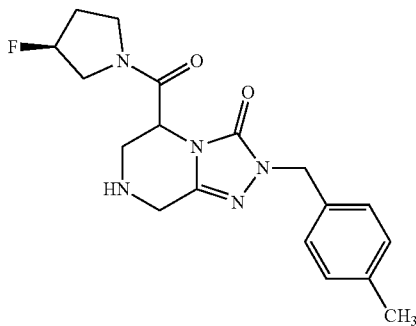 [SMILES: Cc1ccc(Cn2nc3n(c2=O)C(C(=O)N2CC[C@H](F)C2)CNC3)cc1]

tert-Butyl (5RS)-5-{[(3S)-3-fluoropyrrolidin-1-yl]carbonyl}-2-(4-methylbenzyl)-3-oxo-2,5,6,8-tetrahydro[1,2,4]triazolo[4,3-a]pyrazine-7(3H)-carboxylate (diastereomer mixture; 2 isomers) (240 mg, 522 µmol) was dissolved in dichloromethane (4.0 ml) and trifluoroacetic acid (2.0 ml). The reaction mixture was stirred at room temperature for 20 minutes and then diluted with dichloromethane. The organic phase was washed with saturated aqueous sodium hydrogencarbonate solution. The aqueous phase was extracted with dichloromethane. The combined organic phases were dried over magnesium sulfate and filtered, and the filtrate was concentrated. 170 mg (90% purity, 82% of theory) of the title compound were obtained.

LC-MS (Method 2): $R_t$=1.00 min; MS (ESIpos): m/z=360 [M+H]$^+$ $^1$H-NMR (400 MHz, DMSO-d6) δ [ppm]: −0.008 (0.58), 0.008 (0.52), 2.094 (0.45), 2.113 (0.46), 2.251 (0.80), 2.272 (14.07), 3.120 (0.50), 3.155 (0.82), 3.229 (0.42), 3.271 (0.56), 3.284 (0.77), 3.316 (3.54), 3.362 (0.66), 3.379 (0.72), 3.390 (0.41), 3.407 (0.44), 3.539 (0.46), 3.547 (0.50), 3.574 (0.68), 3.609 (0.85), 3.662 (0.42), 3.674 (0.62), 3.687 (0.97), 3.715 (1.30), 3.729 (1.43), 3.761 (2.57), 3.802 (0.96), 3.831 (0.40), 3.905 (0.43), 3.977 (0.42), 4.651 (0.47), 4.689 (0.52), 4.722 (0.56), 4.735 (0.67), 4.747 (0.42), 4.760 (1.75), 4.772 (3.47), 4.816 (0.40), 5.385 (0.43), 7.109 (0.77), 7.131 (16.00). (mixture of diastereomers)

Example 11

(5RS)-5-{[(3S)-3-Fluoropyrrolidin-1-yl]carbonyl}-7-methyl-2-(4-methylbenzyl)-5,6,7,8-tetrahydro[1,2,4]triazolo[4,3-a]pyrazin-3(2H)-one (Diastereomer Mixture; 2 Isomers)

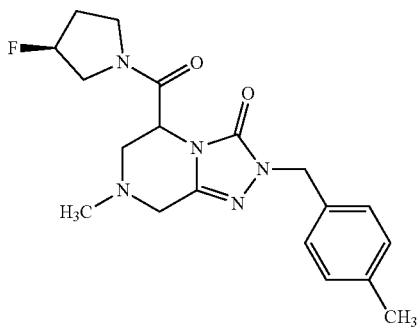 [SMILES: Cc1ccc(Cn2nc3n(c2=O)C(C(=O)N2CC[C@H](F)C2)CN(C)C3)cc1]

To an initial charge of (5RS)-5-{[(3S)-3-fluoropyrrolidin-1-yl]carbonyl}-2-(4-methylbenzyl)-5,6,7,8-tetrahydro[1,2,4]triazolo[4,3-a]pyrazin-3(2H)-one (diastereomer mixture; 2 isomers) (80.0 mg, 90% purity, 200 µmol) in THF (2.0 ml) was added N,N-diisopropylethylamine (70 µl, 400 µmol). After addition of iodomethane (19 µl, 300 µmol), the mixture was stirred at room temperature overnight. After addition of iodomethane (8.5 µl, 150 µmol) and N,N-diisopropylethylamine (35 µl, 200 µmol), the mixture was stirred at room temperature for 3 h. The solvent was removed under reduced pressure, and the residue was purified via preparative HPLC (Chromatorex C18, 10 µm, 125 mm×30 mm; eluent: acetonitrile/water gradient). The product-containing fractions were concentrated under reduced pressure, and 42.7 mg (57% of theory) of the title compound were obtained.

LC-MS (Method 1): $R_t$=0.66 min; MS (ESIpos): m/z=374 [M+H]$^+$ $^1$H-NMR (500 MHz, DMSO-d6) δ [ppm]: −0.007 (0.50), 2.144 (0.45), 2.233 (0.44), 2.274 (16.00), 2.296 (5.31), 2.307 (12.12), 2.855 (0.45), 2.868 (0.70), 2.876 (1.59), 2.886 (1.52), 2.947 (0.44), 2.958 (0.47), 3.216 (0.84), 3.246 (1.05), 3.257 (0.82), 3.271 (0.76), 3.288 (1.35), 3.303 (1.90), 3.314 (2.42), 3.352 (0.71), 3.381 (0.44), 3.396 (0.55), 3.404 (0.42), 3.448 (0.71), 3.483 (0.94), 3.496 (0.98), 3.514 (1.85), 3.526 (1.47), 3.545 (1.21), 3.571 (0.49), 3.600 (0.41), 3.669 (0.60), 3.751 (0.67), 3.817 (0.43), 3.875 (0.47), 3.961 (0.49), 4.688 (0.55), 4.738 (0.83), 4.749 (0.46), 4.766 (3.61), 4.771 (4.75), 4.813 (0.42), 4.823 (0.88), 4.833 (0.43), 4.841 (0.45), 4.851 (0.92), 4.861 (0.41), 5.383 (0.44), 5.390 (0.51), 7.110 (0.96), 7.114 (0.86), 7.130 (11.55), 7.146 (0.98). (mixture of diastereomers)

Example 12

(5RS)-5-{[(3S)-3-Fluoropyrrolidin-1-yl]carbonyl}-7-methyl-2-(4-methylbenzyl)-5,6,7,8-tetrahydro[1,2,4]triazolo[4,3-a]pyrazin-3(2H)-one (Isomer 1)

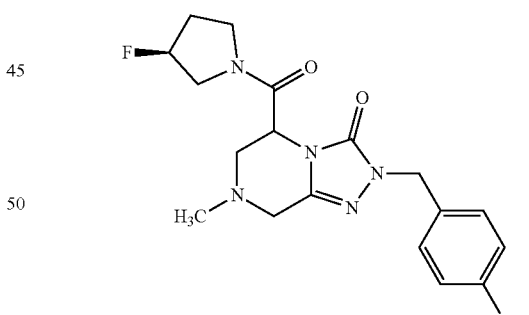

(5RS)-5-{[(3S)-3-Fluoropyrrolidin-1-yl]carbonyl}-7-methyl-2-(4-methylbenzyl)-5,6,7,8-tetrahydro[1,2,4]triazolo[4,3-a]pyrazin-3(2H)-one (diastereomer mixture; 2 isomers) was separated by chiral preparative liquid chromatography [sample preparation: 185.5 mg dissolved in 8 ml of ethanol; injection volume: 0.5 ml; column: Daicel Chiralpak® IC 5 µm, 250×20 mm; eluent: n-heptane/ethanol: isocratic 70% ethanol, flow rate: 15.0 ml/min; temperature 25° C.; UV detection: 210 nm]. After the separation, 86.2 mg of isomer 1, which eluted first, and 54.2 mg of isomer 2, which eluted later, were isolated.

Isomer 1:

Analytical chiral HPLC: $R_t$=3.23 min, d.e.=100% [column: Daicel Chiralpak® IC-3 3 µm 50×4.6 mm; eluent: n-heptane/ethanol 1:1; flow rate: 1 ml/min; UV detection: 220 nm]

LC-MS (Method 2): $R_t$=1.20 min; MS (ESIpos): m/z=374 [M+H]$^+$ $^1$H-NMR (400 MHz, DMSO-d6) δ [ppm]: 0.008 (0.72), 2.095 (0.48), 2.113 (0.58), 2.141 (0.45), 2.188 (0.47), 2.238 (0.58), 2.274 (16.00), 2.296 (7.60), 2.308 (8.02), 2.852 (0.47), 2.875 (2.24), 2.887 (2.54), 2.944 (0.72), 2.957 (0.78), 2.975 (0.41), 3.212 (1.16), 3.250 (2.02), 3.291 (1.54), 3.379 (0.58), 3.397 (0.57), 3.493 (1.61), 3.512 (2.95), 3.531 (1.71), 3.550 (1.59), 3.565 (0.63), 3.582 (1.17), 3.600 (0.62), 3.608 (0.77), 3.938 (0.42), 3.963 (0.79), 3.984 (0.69), 4.772 (7.89), 4.812 (0.66), 4.824 (1.35), 4.837 (1.02), 4.851 (1.40), 4.864 (0.62), 5.269 (0.53), 5.341 (0.53), 5.405 (0.54), 5.474 (0.51), 7.109 (0.63), 7.131 (14.87), 7.150 (0.72).

Example 13

(5RS)-5-{[(3S)-3-Fluoropyrrolidin-1-yl]carbonyl}-7-methyl-2-(4-methylbenzyl)-5,6,7,8-tetrahydro[1,2,4]triazolo[4,3-a]pyrazin-3(2H)-one (Isomer 2)

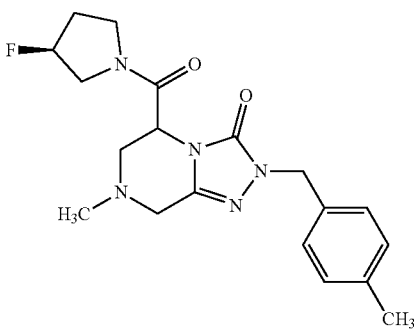 [SMILES: Cc1ccc(Cn2nc3n(c2=O)C(C(=O)N2CC[C@H](F)C2)CN(C)C3)cc1]

(5RS)-5-{[(3S)-3-Fluoropyrrolidin-1-yl]carbonyl}-7-methyl-2-(4-methylbenzyl)-5,6,7,8-tetrahydro[1,2,4]triazolo[4,3-a]pyrazin-3(2H)-one (diastereomer mixture; 2 isomers) was separated by chiral preparative liquid chromatography [sample preparation: 185.5 mg dissolved in 8 ml of warm ethanol; injection volume: 0.5 ml; column: Daicel Chirapak® IC 5 µm, 250×20 mm; eluent: n-heptane/ethanol: isocratic 70% ethanol, flow rate: 15.0 ml/min; temperature 25° C.; UV detection: 210 nm]. After the separation, 86.2 mg of isomer 1, which eluted first, and 54.2 mg of isomer 2, which eluted later, were isolated.

Isomer 2:

Analytical chiral HPLC: $R_t$=2.08 min, d.e.=100% [column: Daicel Chiralpak® IC-3 3 µm 50×4.6 mm; eluent: n-heptane/ethanol 1:1; flow rate: 1 ml/min; UV detection: 220 nm]

LC-MS (Method 1): $R_t$=0.72 min; MS (ESIpos): m/z=374 [M+H]$^+$ $^1$H-NMR (400 MHz, DMSO-d6) δ [ppm]: −0.008 (0.54), 0.008 (0.52), 2.096 (0.44), 2.114 (0.42), 2.131 (0.53), 2.233 (0.45), 2.274 (15.49), 2.307 (16.00), 2.722 (0.42), 2.737 (0.43), 2.754 (0.50), 2.768 (0.50), 2.839 (0.49), 2.852 (0.52), 2.870 (0.72), 2.884 (0.72), 2.988 (0.68), 3.002 (0.75), 3.020 (0.58), 3.031 (0.69), 3.040 (0.58), 3.059 (0.42), 3.267 (1.18), 3.289 (0.58), 3.355 (1.41), 3.445 (1.39), 3.481 (2.05), 3.494 (0.47), 3.518 (1.15), 3.645 (0.61), 3.662 (1.32), 3.688 (0.96), 3.695 (0.73), 3.728 (0.96), 3.752 (0.86), 3.810 (0.97), 3.883 (1.03), 4.674 (0.52), 4.688 (1.10), 4.702 (0.54), 4.725 (0.83), 4.738 (1.60), 4.752 (0.96), 4.765 (7.33), 5.256 (0.56), 5.381 (0.68), 5.388 (0.70), 7.106 (0.84), 7.128 (11.71), 7.150 (0.96).

Example 14

(5RS)-7-(Cyclopropylcarbonyl)-2-(4-methylbenzyl)-5-(pyrrolidin-1-ylcarbonyl)-5,6,7,8-tetrahydro[1,2,4]triazolo[4,3-a]pyrazin-3(2H)-one (Racemate)

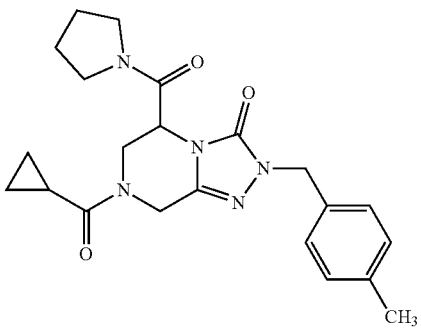 [SMILES: Cc1ccc(Cn2nc3n(c2=O)C(C(=O)N2CCCC2)CN(C(=O)C2CC2)C3)cc1]

To a solution of (5RS)-2-(4-methylbenzyl)-5-(pyrrolidin-1-ylcarbonyl)-5,6,7,8-tetrahydro[1,2,4]triazolo[4,3-a]pyrazin-3(2H)-one (racemate) (50.0 mg, 85% purity, 124 µmol) in dichloromethane (1.0 ml) and N,N-diisopropylethylamine (43 µl, 250 µmol) was added cyclopropanecarbonyl chloride (12 µl, 140 µmol). The reaction mixture was stirred at room temperature for 1 hour. Subsequently, all volatile constituents were removed under reduced pressure and the residue was taken up in acetonitrile/water and purified via preparative HPLC (Chromatorex C18, 10 µm, 125 mm×30 mm; eluent: acetonitrile/water gradient). The product-containing fractions were concentrated under reduced pressure, and 43.5 mg (85% of theory) of the title compound were obtained.

LC-MS (Method 2): $R_t$=1.33 min; MS (ESIpos): m/z=410 [M+H]$^+$ $^1$H-NMR (400 MHz, DMSO-d6) δ [ppm]: −0.008 (0.76), 0.008 (0.57), 0.605 (0.69), 0.690 (1.35), 0.743 (0.83), 1.768 (1.02), 1.785 (1.09), 1.801 (0.90), 1.923 (1.86), 1.938 (1.94), 1.954 (1.21), 2.274 (16.00), 3.261 (0.69), 3.640 (1.20), 3.655 (1.80), 3.926 (0.41), 3.960 (0.44), 4.045 (0.57), 4.087 (0.62), 4.617 (0.93), 4.654 (0.87), 4.795 (4.48), 4.834 (0.57), 4.913 (0.88), 5.063 (0.66), 5.106 (0.81), 7.135 (11.00).

Example 15

(5RS)-7-(Cyclopropylcarbonyl)-2-(4-methylbenzyl)-5-(pyrrolidin-1-ylcarbonyl)-5,6,7,8-tetrahydro[1,2,4]triazolo[4,3-a]pyrazin-3(2H)-one (Enantiomer 1)

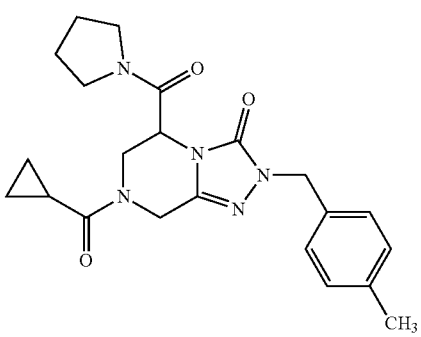 [SMILES: Cc1ccc(Cn2nc3n(c2=O)C(C(=O)N2CCCC2)CN(C(=O)C2CC2)C3)cc1]

(5RS)-7-(Cyclopropylcarbonyl)-2-(4-methylbenzyl)-(pyrrolidin-1-ylcarbonyl)-5,6,7,8-tetrahydro[1,2,4]triazolo[4,3-a]pyrazin-3(2H)-one (racemate) was separated by chiral preparative liquid chromatography [sample preparation: 117.3 mg dissolved in 4 ml of ethanol; injection volume: 1.0 ml; column: Daicel Chirapak® IA 5 µm, 250×20 mm; eluent: ethanol: isocratic 100% ethanol, flow rate: 15.0 ml/min; temperature 55° C.; UV detection: 210 nm]. After the separation, 45.1 mg of enantiomer 1, which eluted first, and 46.0 mg of enantiomer 2, which eluted later, were isolated.

Enantiomer 1:
Analytical chiral HPLC: $R_t$=6.46 min, e.e.=100% [column: Daicel Chiralpak® IF 3 µm 250×4.6 mm; eluent: ethanol; flow rate: 1 ml/min; UV detection: 220 nm]

LC-MS (Method 2): $R_t$=1.34 min; MS (ESIpos): m/z=410 [M+H]$^+$ $^1$H-NMR (400 MHz, DMSO-d6) δ [ppm]: 0.606 (0.70), 0.691 (1.39), 0.745 (0.87), 1.769 (1.04), 1.786 (1.12), 1.802 (0.93), 1.924 (1.90), 1.939 (1.99), 2.274 (16.00), 2.523 (0.43), 3.261 (0.68), 3.641 (1.23), 3.656 (1.85), 3.928 (0.43), 3.958 (0.46), 4.045 (0.59), 4.087 (0.64), 4.617 (0.95), 4.655 (0.89), 4.796 (4.60), 4.834 (0.60), 4.914 (0.91), 5.064 (0.68), 5.106 (0.84), 7.135 (11.22).

Example 16

(5RS)-7-(Cyclopropylcarbonyl)-2-(4-methylbenzyl)-5-(pyrrolidin-1-ylcarbonyl)-5,6,7,8-tetrahydro[1,2,4]triazolo[4,3-a]pyrazin-3(2H)-one (Enantiomer 2)

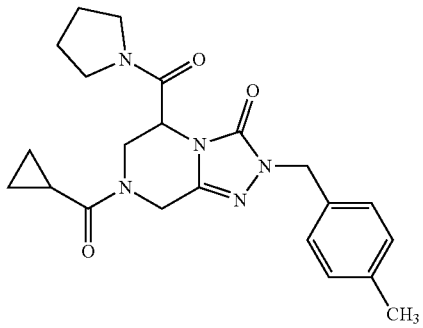 [SMILES: Cc1ccc(Cn2nc3n(c2=O)C(C(=O)N2CCCC2)CN(C(=O)C2CC2)C3)cc1]

(5RS)-7-(Cyclopropylcarbonyl)-2-(4-methylbenzyl)-(pyrrolidin-1-ylcarbonyl)-5,6,7,8-tetrahydro[1,2,4]triazolo[4,3-a]pyrazin-3(2H)-one (racemate) was separated by chiral preparative liquid chromatography [sample preparation: 117.3 mg dissolved in 4 ml of ethanol; injection volume: 1.0 ml; column: Daicel Chirapak® IA 5 µm, 250×20 mm; eluent: ethanol: isocratic 100% ethanol, flow rate: 15.0 ml/min; temperature 55° C.; UV detection: 210 nm]. After the separation, 45.1 mg of enantiomer 1, which eluted first, and 46.0 mg of enantiomer 2, which eluted later, were isolated.

Enantiomer 2:
Analytical chiral HPLC: $R_t$=28.6 min, e.e.=99% [column: Daicel Chiralpak® IF 3 µm 250×4.6 mm; eluent: ethanol; flow rate: 1 ml/min; UV detection: 220 nm]

LC-MS (Method 2): $R_t$=1.34 min; MS (ESIpos): m/z=410 [M+H]$^+$ $^1$H-NMR (400 MHz, DMSO-d6) δ [ppm]: 0.606 (0.70), 0.691 (1.36), 0.745 (0.84), 1.768 (1.03), 1.786 (1.10), 1.801 (0.91), 1.923 (1.86), 1.938 (1.95), 1.953 (1.23), 2.274 (16.00), 3.260 (0.70), 3.640 (1.21), 3.655 (1.81), 3.927 (0.41), 3.959 (0.44), 4.044 (0.57), 4.086 (0.62), 4.617 (0.93), 4.655 (0.86), 4.795 (4.51), 4.834 (0.57), 4.913 (0.88), 5.064 (0.67), 5.106 (0.82), 7.135 (11.10).

Example 17

(5RS)-2-(4-Methylbenzyl)-3-oxo-5-(pyrrolidin-1-ylcarbonyl)-N-(2,2,2-trifluoroethyl)-2,5,6,8-tetrahydro[1,2,4]triazolo[4,3-a]pyrazine-7(3H)-carboxamide (Racemate)

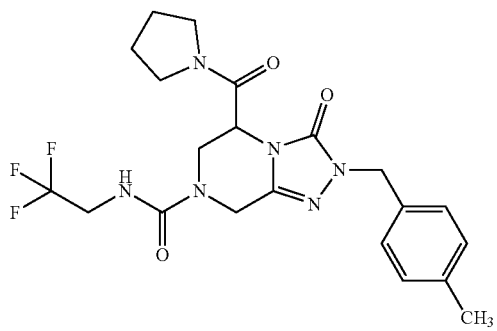 [SMILES: Cc1ccc(Cn2nc3n(c2=O)C(C(=O)N2CCCC2)CN(C(=O)NCC(F)(F)F)C3)cc1]

(5RS)-2-(4-Methylbenzyl)-5-(pyrrolidin-1-ylcarbonyl)-5,6,7,8-tetrahydro[1,2,4]triazolo[4,3-a]pyrazin-3(2H)-one (racemate) (25.0 mg, 85% purity, 62.2 µmol) was dissolved in dichloromethane (500 µl) and then 1,1,1-trifluoro-2-isocyanatoethane (9.34 mg, 74.7 µmol) was added. After stirring at room temperature for two hours, the reaction mixture was concentrated. The residue was taken up in acetonitrile/water and purified via preparative HPLC (Chromatorex C18, 10 µm, 125 mm×30 mm; eluent: acetonitrile/water gradient). The product-containing fractions were concentrated under reduced pressure, and 21.2 mg (73% of theory) of the title compound were obtained.

LC-MS (Method 2): $R_t$=1.40 min; MS (ESIpos): m/z=467 [M+H]$^+$ $^1$H-NMR (400 MHz, DMSO-d6) δ [ppm]: −0.008 (0.44), 0.008 (0.43), 1.750 (0.63), 1.757 (0.43), 1.769 (1.07), 1.788 (1.24), 1.807 (0.90), 1.823 (0.43), 1.918 (0.83), 1.935 (1.17), 1.945 (1.06), 1.952 (0.87), 1.960 (0.74), 2.274 (11.22), 3.174 (0.44), 3.186 (0.66), 3.200 (0.73), 3.219 (0.48), 3.271 (0.55), 3.289 (1.23), 3.335 (0.60), 3.541 (0.65), 3.547 (0.58), 3.565 (0.98), 3.582 (0.44), 3.614 (0.58), 3.621 (0.86), 3.631 (1.46), 3.646 (0.72), 3.657 (1.18), 3.669 (1.07), 3.686 (0.44), 3.711 (0.64), 3.725 (0.43), 3.734 (0.45), 3.866 (0.46), 3.875 (0.40), 3.890 (0.57), 4.243 (1.68), 4.285 (2.32), 4.326 (0.67), 4.333 (0.67), 4.764 (1.65), 4.790 (7.26), 4.806 (1.60), 7.133 (16.00), 7.384 (0.65), 7.399 (1.33), 7.414 (0.65).

Example 18

(5RS)-7-Methyl-2-(4-methylbenzyl)-5-(pyrrolidin-1-ylcarbonyl)-5,6,7,8-tetrahydro[1,2,4]triazolo[4,3-a]pyrazin-3(2H)-one (Racemate)

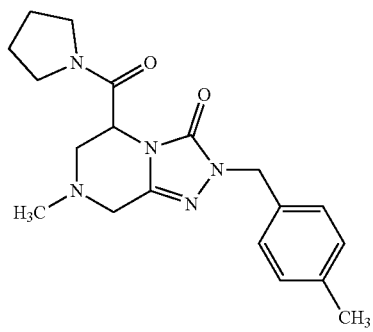 [SMILES: Cc1ccc(Cn2nc3n(c2=O)C(C(=O)N2CCCC2)CN(C)C3)cc1]

To an initial charge of (5RS)-2-(4-methylbenzyl)-5-(pyrrolidin-1-ylcarbonyl)-5,6,7,8-tetrahydro[1,2,4]triazolo[4,3-a]pyrazin-3(2H)-one (racemate) (40.0 mg, 117 μmol) in THF (1.0 ml) was added N,N-diisopropylethylamine (41 μl, 230 μmol). After addition of iodomethane (11 μl, 180 μmol), the mixture was stirred at room temperature overnight. After addition of iodomethane (5.5 μl, 90 μmol) and N,N-diisopropylethylamine (21 μl, 115 μmol), the mixture was stirred at room temperature for 6 h. The solvent was removed under reduced pressure, and the residue was purified via preparative HPLC (Chromatorex C18, 10 μm, 125 mm×30 mm; eluent: acetonitrile/water gradient). The product-containing fractions were concentrated under reduced pressure, and 26.2 mg (63% of theory) of the title compound were obtained.

LC-MS (Method 2): $R_t$=1.17 min; MS (ESIpos): m/z=356 [M+H]$^+$ $^1$H-NMR (400 MHz, DMSO-d6) δ [ppm]: 1.766 (1.05), 1.777 (1.06), 1.785 (1.87), 1.792 (1.51), 1.803 (1.62), 1.823 (0.73), 1.877 (0.46), 1.893 (1.21), 1.909 (1.61), 1.918 (1.50), 1.927 (1.17), 1.934 (1.03), 2.273 (16.00), 2.301 (14.63), 2.816 (0.82), 2.829 (0.85), 2.848 (1.32), 2.861 (1.32), 2.934 (1.25), 2.947 (1.39), 2.965 (0.85), 2.978 (0.79), 3.228 (0.47), 3.253 (2.35), 3.273 (1.38), 3.290 (3.69), 3.312 (2.35), 3.328 (1.25), 3.347 (1.70), 3.358 (0.69), 3.365 (0.90), 3.376 (0.97), 3.394 (0.46), 3.430 (0.51), 3.447 (1.11), 3.454 (0.87), 3.470 (3.86), 3.489 (0.64), 3.508 (2.04), 3.619 (0.60), 3.636 (1.07), 3.644 (0.74), 3.652 (0.77), 3.659 (0.89), 3.676 (0.45), 4.717 (1.23), 4.730 (2.71), 4.743 (1.29), 4.764 (8.79), 7.104 (0.89), 7.126 (14.85), 7.149 (0.89).

Example 19

(5RS)-7-Methyl-2-(4-methylbenzyl)-5-(pyrrolidin-1-ylcarbonyl)-5,6,7,8-tetrahydro[1,2,4]triazolo[4,3-a]pyrazin-3(2H)-one (Enantiomer 1)

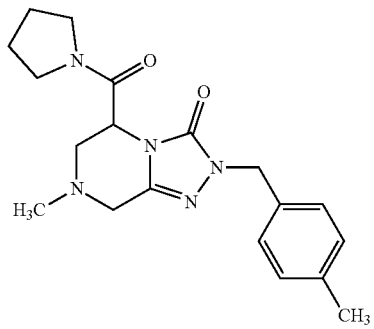

(5RS)-7-Methyl-2-(4-methylbenzyl)-5-(pyrrolidin-1-ylcarbonyl)-5,6,7,8-tetrahydro[1,2,4]triazolo[4,3-a]pyrazin-3(2H)-one (racemate) was separated by chiral preparative liquid chromatography [sample preparation: 84 mg dissolved in 4 ml of warm ethanol; injection volume: 0.25 ml; column: Daicel Chirapak® IB 5 μm, 250×20 mm; eluent: n-heptane/ethanol: isocratic 50% ethanol, flow rate: 15.0 ml/min; temperature 25° C.; UV detection: 210 nm]. After the separation, 30.3 mg of enantiomer 1, which eluted first, and 29.8 mg of enantiomer 2, which eluted later, were isolated.

Enantiomer 1:

Analytical chiral HPLC: $R_t$=3.15 min, e.e.=100% [column: Daicel Chiralpak® IB-3 3 μm 250×4.6 mm; eluent: n-heptane/ethanol 1:1; flow rate: 1 ml/min; UV detection: 220 nm]

LC-MS (Method 2): $R_t$=1.19 min; MS (ESIpos): m/z=356 [M+H]$^+$ $^1$H-NMR (500 MHz, DMSO-d6) δ [ppm]: 1.236 (0.67), 1.324 (0.62), 1.770 (1.48), 1.784 (2.55), 1.796 (2.36), 1.806 (1.77), 1.895 (1.70), 1.908 (2.54), 1.920 (2.28), 1.931 (1.47), 2.273 (16.00), 2.301 (14.24), 2.821 (1.06), 2.831 (1.13), 2.846 (1.55), 2.856 (1.47), 2.938 (1.52), 2.948 (1.58), 2.963 (1.09), 2.973 (1.00), 3.235 (0.75), 3.258 (3.39), 3.271 (1.83), 3.287 (3.63), 3.334 (1.53), 3.349 (2.02), 3.365 (3.12), 3.387 (0.66), 3.436 (0.68), 3.450 (1.48), 3.472 (3.80), 3.503 (2.20), 3.625 (0.79), 3.638 (1.40), 3.656 (1.19), 3.669 (0.58), 4.720 (1.56), 4.730 (2.92), 4.740 (1.65), 4.764 (9.06), 7.109 (1.81), 7.127 (13.42), 7.145 (1.65).

Example 20

(5RS)-7-Methyl-2-(4-methylbenzyl)-5-(pyrrolidin-1-ylcarbonyl)-5,6,7,8-tetrahydro[1,2,4]triazolo[4,3-a]pyrazin-3(2H)-one (Enantiomer 2)

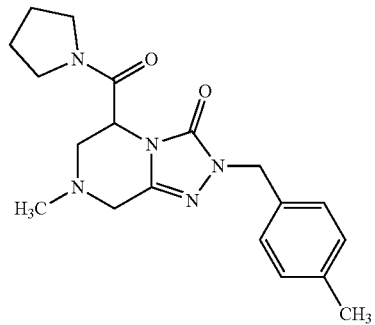

(5RS)-7-Methyl-2-(4-methylbenzyl)-5-(pyrrolidin-1-ylcarbonyl)-5,6,7,8-tetrahydro[1,2,4]triazolo[4,3-a]pyrazin-3(2H)-one (racemate) was separated by chiral preparative liquid chromatography [sample preparation: 84 mg dissolved in 4 ml of warm ethanol; injection volume: 0.25 ml; column: Daicel Chirapak® IB 5 μm, 250×20 mm; eluent: n-heptane/ethanol: isocratic 50% ethanol, flow rate: 15.0 ml/min; temperature 25° C.; UV detection: 210 nm]. After the separation, 30.3 mg of enantiomer 1, which eluted first, and 29.8 mg of enantiomer 2, which eluted later, were isolated.

Enantiomer 2:

Analytical chiral HPLC: $R_t$=4.94 min, e.e.=100% [column: Daicel Chiralpak® IB-3 3 μm 250×4.6 mm; eluent: n-heptane/ethanol 1:1; flow rate: 1 ml/min; UV detection: 220 nm]

LC-MS (Method 2): $R_t$=1.20 min; MS (ESIpos): m/z=356 [M+H]$^+$ $^1$H-NMR (400 MHz, DMSO-d6) δ [ppm]: −0.008 (1.38), 0.008 (1.39), 1.139 (1.67), 1.157 (3.43), 1.175 (1.76), 1.767 (1.05), 1.786 (1.86), 1.793 (1.51), 1.804 (1.65), 1.824 (0.77), 1.894 (1.16), 1.910 (1.53), 1.919 (1.45), 1.927 (1.16), 1.935 (1.05), 2.273 (16.00), 2.302 (14.41), 2.328 (0.52), 2.523

(1.38), 2.670 (0.43), 2.817 (0.81), 2.830 (0.83), 2.848 (1.26), 2.861 (1.28), 2.897 (0.48), 2.915 (1.92), 2.934 (2.38), 2.948 (1.51), 2.966 (0.85), 2.980 (0.83), 3.228 (0.41), 3.253 (2.23), 3.273 (1.32), 3.291 (3.68), 3.347 (1.96), 3.359 (0.85), 3.365 (1.05), 3.376 (1.07), 3.395 (0.54), 3.430 (0.54), 3.448 (1.14), 3.454 (0.91), 3.471 (3.74), 3.490 (0.68), 3.508 (2.05), 3.620 (0.62), 3.636 (1.07), 3.652 (0.77), 3.659 (0.87), 3.677 (0.46), 4.718 (1.20), 4.731 (2.63), 4.744 (1.26), 4.764 (8.52), 5.753 (0.50), 7.104 (0.85), 7.126 (13.02), 7.150 (1.30), 7.154 (1.38).

Example 21

(5RS)—N-Cyclopropyl-2-(4-methylbenzyl)-3-oxo-5-(pyrrolidin-1-ylcarbonyl)-2,5,6,8-tetrahydro[1,2,4]triazolo[4,3-a]pyrazine-7(3H)-carboxamide (Racemate)

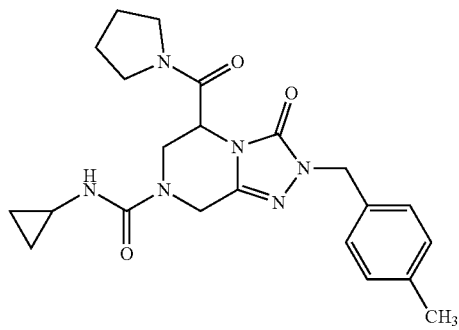 [SMILES: Cc1ccc(Cn2nc3n(c2=O)C(C(=O)N2CCCC2)CN(C(=O)NC2CC2)C3)cc1]

(5RS)-2-(4-Methylbenzyl)-5-(pyrrolidin-1-ylcarbonyl)-5,6,7,8-tetrahydro[1,2,4]triazolo[4,3-a]pyrazin-3(2H)-one (racemate) (50.0 mg, 85% purity, 124 µmol) was dissolved in dichloromethane (1.0 ml) and then isocyanatocyclopropane (10 µl, 150 µmol) was added. After stirring at room temperature for two hours, the reaction mixture was concentrated. The residue was taken up in acetonitrile/water and purified via preparative HPLC (Chromatorex C18, 10 µm, 125 mm×30 mm; eluent: acetonitrile/water gradient). The product-containing fractions were concentrated under reduced pressure, and 37.2 mg (70% of theory) of the title compound were obtained.

LC-MS (Method 2): $R_t$=1.24 min; MS (ESIpos): m/z=425 [M+H]$^+$ $^1$H-NMR (400 MHz, DMSO-d6) δ [ppm]: −0.008 (0.62), 0.008 (0.52), 0.313 (2.64), 0.321 (2.49), 0.339 (0.48), 0.499 (0.60), 0.512 (1.45), 0.518 (1.75), 0.529 (1.62), 0.535 (1.54), 0.551 (0.45), 1.761 (0.75), 1.766 (0.56), 1.779 (1.34), 1.798 (1.59), 1.816 (1.08), 1.832 (0.48), 1.919 (1.02), 1.927 (1.00), 1.935 (1.36), 1.942 (1.29), 1.952 (0.97), 1.958 (0.90), 2.272 (12.76), 2.418 (0.42), 2.425 (0.70), 2.434 (0.90), 2.442 (0.88), 2.451 (0.66), 2.458 (0.41), 3.160 (0.55), 3.175 (0.75), 3.189 (0.84), 3.208 (0.53), 3.284 (0.65), 3.331 (0.99), 3.349 (0.43), 3.520 (0.78), 3.526 (0.69), 3.545 (1.20), 3.556 (1.06), 3.567 (1.13), 3.593 (1.47), 3.604 (1.20), 3.610 (1.15), 3.627 (0.66), 3.635 (0.65), 4.124 (2.07), 4.166 (2.35), 4.209 (0.88), 4.215 (0.91), 4.245 (0.80), 4.252 (0.80), 4.705 (2.04), 4.720 (1.83), 4.729 (1.08), 4.747 (1.66), 4.776 (6.62), 6.830 (1.87), 6.836 (1.86), 7.107 (0.52), 7.129 (16.00), 7.152 (0.52)

Example 22

(5RS)—N-Cyclopropyl-2-(4-methylbenzyl)-3-oxo-5-(pyrrolidin-1-ylcarbonyl)-2,5,6,8-tetrahydro[1,2,4]triazolo[4,3-a]pyrazine-7(3H)-carboxamide (Enantiomer 1)

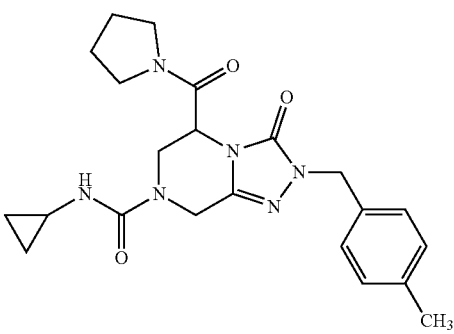 [SMILES: Cc1ccc(Cn2nc3n(c2=O)C(C(=O)N2CCCC2)CN(C(=O)NC2CC2)C3)cc1]

(5RS)—N-Cyclopropyl-2-(4-methylbenzyl)-3-oxo-5-(pyrrolidin-1-ylcarbonyl)-2,5,6,8-tetrahydro[1,2,4]triazolo[4,3-a]pyrazine-7(3H)-carboxamide (racemate) was separated by chiral preparative liquid chromatography [sample preparation: 113.4 mg dissolved in 8 ml of warm ethanol; injection volume: 0.5 ml; column: Daicel Chirapak® AD-H 5 µm, 250×20 mm; eluent: n-heptane/ethanol: isocratic 50% ethanol, flow rate: 15.0 ml/min; temperature 25° C.; UV detection: 210 nm]. After the separation, 15.3 mg of enantiomer 1, which eluted first, and 45.2 mg of enantiomer 2, which eluted later, were isolated.

Enantiomer 1:

Analytical chiral HPLC: $R_t$=1.91 min, e.e.=100% [column: Daicel Chiralpak® AD-3 3 µm 50×4.6 mm; eluent: n-heptane/ethanol 1:1; flow rate: 1 ml/min; UV detection: 220 nm]

LC-MS (Method 2): $R_t$=1.24 min; MS (ESIpos): m/z=425 [M+H]$^+$ $^1$H-NMR (400 MHz, DMSO-d6) δ [ppm]: −0.008 (0.78), 0.007 (0.76), 0.313 (2.71), 0.321 (2.58), 0.339 (0.51), 0.499 (0.60), 0.512 (1.48), 0.518 (1.81), 0.530 (1.69), 0.536 (1.62), 0.552 (0.49), 1.761 (0.76), 1.766 (0.58), 1.780 (1.36), 1.798 (1.62), 1.816 (1.11), 1.832 (0.51), 1.919 (1.05), 1.927 (1.06), 1.935 (1.42), 1.943 (1.36), 1.953 (1.04), 1.959 (0.96), 2.272 (12.80), 2.425 (0.70), 2.434 (0.90), 2.442 (0.89), 2.451 (0.67), 2.458 (0.41), 3.160 (0.55), 3.175 (0.76), 3.189 (0.83), 3.208 (0.53), 3.284 (0.62), 3.331 (1.16), 3.349 (0.49), 3.520 (0.80), 3.526 (0.72), 3.544 (1.24), 3.556 (1.11), 3.567 (1.17), 3.593 (1.48), 3.604 (1.24), 3.610 (1.19), 3.627 (0.71), 3.635 (0.71), 4.124 (2.04), 4.166 (2.33), 4.209 (0.91), 4.215 (0.94), 4.245 (0.83), 4.252 (0.83), 4.706 (2.07), 4.720 (1.88), 4.729

(1.13), 4.747 (1.70), 4.776 (6.69), 6.829 (1.89), 6.834 (1.90), 7.107 (0.51), 7.129 (16.00), 7.152 (0.61).

Example 23

(5RS)—N-Cyclopropyl-2-(4-methylbenzyl)-3-oxo-5-(pyrrolidin-1-ylcarbonyl)-2,5,6,8-tetrahydro[1,2,4]triazolo[4,3-a]pyrazine-7(3H)-carboxamide (Enantiomer 2)

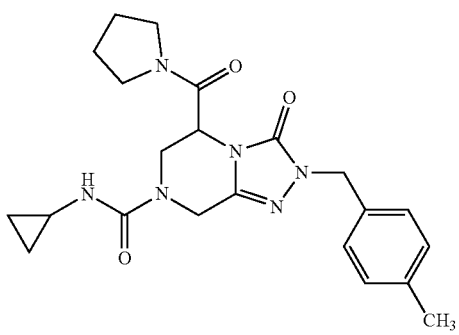 [SMILES: Cc1ccc(Cn2nc3n(c2=O)C(C(=O)N2CCCC2)CN(C(=O)NC2CC2)C3)cc1]

(5RS)—N-Cyclopropyl-2-(4-methylbenzyl)-3-oxo-5-(pyrrolidin-1-ylcarbonyl)-2,5,6,8-tetrahydro[1,2,4]triazolo[4,3-a]pyrazine-7(3H)-carboxamide (racemate) was separated by chiral preparative liquid chromatography [sample preparation: 113.4 mg dissolved in 8 ml of warm ethanol; injection volume: 0.5 ml; column: Daicel Chirapak® AD-H 5 μm, 250×20 mm; eluent: n-heptane/ethanol: isocratic 50% ethanol, flow rate: 15.0 ml/min; temperature 25° C.; UV detection: 210 nm]. After the separation, 15.3 mg of enantiomer 1, which eluted first, and 45.2 mg of enantiomer 2, which eluted later, were isolated.

Enantiomer 2:

Analytical chiral HPLC: $R_t$=2.93 min, e.e.=100% [column: Daicel Chiralpak® AD-3 3 μm 50×4.6 mm; eluent: n-heptane/ethanol 1:1; flow rate: 1 ml/min; UV detection: 220 nm]

LC-MS (Method 2): $R_t$=1.24 min; MS (ESIpos): m/z=425 [M+H]$^+$ $^1$H-NMR (400 MHz, DMSO-d6) δ [ppm]: 0.313 (2.59), 0.321 (2.45), 0.339 (0.45), 0.499 (0.56), 0.518 (1.69), 0.529 (1.57), 0.535 (1.52), 0.551 (0.46), 1.761 (0.69), 1.779 (1.28), 1.798 (1.52), 1.816 (1.05), 1.832 (0.46), 1.919 (0.99), 1.936 (1.35), 1.953 (0.97), 2.272 (12.59), 2.425 (0.71), 2.434 (0.91), 2.441 (0.89), 2.450 (0.68), 2.458 (0.43), 3.161 (0.52), 3.174 (0.73), 3.189 (0.82), 3.207 (0.50), 3.284 (0.59), 3.331 (1.02), 3.349 (0.43), 3.520 (0.76), 3.526 (0.69), 3.544 (1.18), 3.556 (1.02), 3.567 (1.07), 3.593 (1.40), 3.604 (1.17), 3.610 (1.11), 3.627 (0.66), 3.635 (0.65), 4.124 (1.90), 4.166 (2.17), 4.216 (0.88), 4.245 (0.78), 4.705 (1.97), 4.720 (1.81), 4.729 (1.05), 4.747 (1.59), 4.776 (6.34), 6.828 (1.82), 6.833 (1.80), 7.107 (0.53), 7.129 (16.00), 7.151 (0.57).

Example 24

(5RS)-2-(4-Methylbenzyl)-3-oxo-5-(pyrrolidin-1-ylcarbonyl)-N-[4-(trifluoromethyl)phenyl]-2,5,6,8-tetrahydro[1,2,4]triazolo[4,3-a]pyrazine-7(3H)-carboxamide (Racemate)

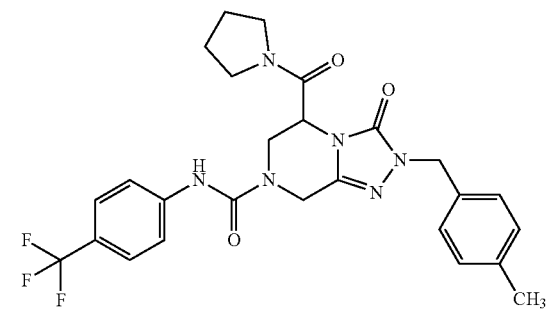 [SMILES: Cc1ccc(Cn2nc3n(c2=O)C(C(=O)N2CCCC2)CN(C(=O)Nc2ccc(C(F)(F)F)cc2)C3)cc1]

To a solution of (5RS)-2-(4-methylbenzyl)-5-(pyrrolidin-1-ylcarbonyl)-5,6,7,8-tetrahydro[1,2,4]triazolo[4,3-a]pyrazin-3(2H)-one (racemate) (50.0 mg, 85% purity, 124 μmol) in dichloromethane (1.0 ml) was added 1-isocyanato-4-(trifluoromethyl)benzene (21 μl, 150 μmol). The reaction mixture was stirred at room temperature for one hour. The resultant precipitate was filtered off and washed with petroleum ether and dried under reduced pressure. 46.3 mg (70% of theory) of the title compound were obtained.

LC-MS (Method 2): $R_t$=1.81 min; MS (ESIpos): m/z=529 [M+H]$^+$ $^1$H-NMR (400 MHz, DMSO-d6) δ [ppm]: 0.839 (0.51), 0.855 (0.58), 1.236 (0.57), 1.614 (0.43), 1.632 (0.55), 1.727 (0.52), 1.743 (0.56), 1.758 (0.44), 1.902 (0.70), 1.919 (1.13), 1.935 (0.99), 1.949 (0.63), 2.276 (9.71), 2.957 (0.51), 2.970 (0.45), 3.203 (0.71), 3.214 (0.41), 3.221 (0.44), 3.232 (0.61), 3.559 (0.56), 3.583 (0.81), 3.645 (0.66), 3.662 (0.48), 3.701 (0.57), 3.711 (0.64), 3.738 (0.68), 3.748 (0.59), 4.311 (1.25), 4.354 (1.41), 4.545 (0.71), 4.581 (0.66), 4.804 (4.73), 4.857 (1.18), 5.003 (1.19), 5.045 (1.07), 7.144 (16.00), 7.595 (13.12), 9.111 (2.21).

Example 25

(5RS)-2-{[3-Chloro-4-(trifluoromethyl)pyridin-2-yl]methyl}-5-{[(3S)-3-fluoropyrrolidin-1-yl]carbonyl}-7-(2,2,2-trifluoroethyl)-5,6,7,8-tetrahydro[1,2,4]triazolo[4,3-a]pyrazin-3(2H)-one (Diastereomer Mixture; 2 Isomers)

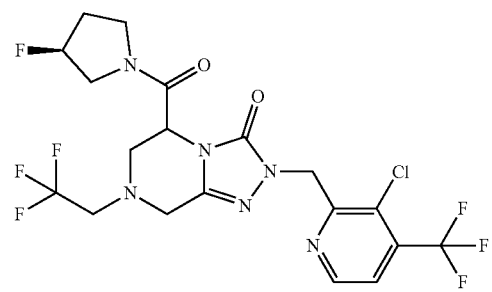 [SMILES: O=C(C1CN(CC(F)(F)F)Cc2nn(Cc3nccc(C(F)(F)F)c3Cl)c(=O)n21)N1CC[C@H](F)C1]

To a solution of (5RS)-2-{[3-chloro-4-(trifluoromethyl)pyridin-2-yl]methyl}-5-{[(3S)-3-fluoropyrrolidin-1-yl]carbonyl}-5,6,7,8-tetrahydro[1,2,4]triazolo[4,3-a]pyrazin-3(2H)-one (diastereomer mixture; 2 isomers) (20.0 mg, 44.6 µmol) in DMF (1.0 ml) and N,N-diisopropylethylamine (23 µl, 130 µmol) was added 2,2,2-trifluoroethyl trifluoromethanesulfonate (12.4 mg, 53.5 µmol). The reaction mixture was stirred at room temperature for 6 hours. Again, 2,2,2-trifluoroethyl trifluoromethanesulfonate (12.4 mg, 53.5 µmol) was added and the mixture stirred overnight. 2,2,2-Trifluoroethyl trifluoromethanesulfonate (24.8 mg, 107.0 µmol) was added and the mixture was stirred for a further 24 hours. Subsequently, all volatile constituents were removed under reduced pressure and the residue was purified via preparative HPLC (Chromatorex C18, 10 µm, 125 mm×30 mm; eluent: acetonitrile/water gradient). The product-containing fractions were concentrated under reduced pressure, and 10.5 mg (44% of theory) of the title compound were obtained.

LC-MS (Method 2): $R_t$=1.60 min; MS (ESIpos): m/z=531 [M+H]$^+$ $^1$H-NMR (400 MHz, DMSO-d6) δ [ppm]: 1.236 (1.26), 2.102 (1.14), 2.235 (0.98), 3.087 (0.46), 3.121 (0.58), 3.145 (0.81), 3.158 (0.97), 3.194 (1.47), 3.232 (0.99), 3.244 (0.98), 3.345 (2.85), 3.370 (2.02), 3.383 (3.78), 3.408 (3.47), 3.444 (1.53), 3.490 (3.16), 3.514 (3.43), 3.540 (2.16), 3.555 (2.21), 3.663 (1.68), 3.687 (1.94), 3.704 (2.38), 3.726 (4.16), 3.751 (2.90), 3.761 (3.26), 3.823 (6.62), 3.862 (2.86), 3.895 (1.41), 3.951 (0.68), 3.974 (1.16), 3.999 (1.08), 4.032 (0.48), 4.057 (0.50), 4.091 (0.46), 4.738 (0.62), 4.752 (1.18), 4.767 (0.67), 4.796 (0.81), 4.809 (1.53), 4.823 (0.76), 4.879 (1.49), 4.893 (1.41), 4.906 (1.75), 5.190 (16.00), 5.265 (1.53), 5.396 (1.61), 5.493 (0.73), 5.753 (1.54), 7.851 (7.25), 7.863 (7.53), 8.737 (6.28), 8.749 (6.10). (mixture of diastereomers)

Example 26

(5RS)—N-(3,4-Dichlorophenyl)-2-(4-methylbenzyl)-3-oxo-5-(pyrrolidin-1-ylcarbonyl)-2,5,6,8-tetrahydro[1,2,4]triazolo[4,3-a]pyrazine-7(3H)-carboxamide (Racemate)

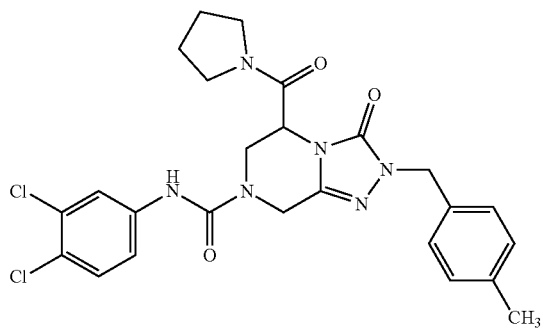 [SMILES: Cc1ccc(Cn2nc3n(c2=O)C(C(=O)N2CCCC2)CN(C(=O)Nc2ccc(Cl)c(Cl)c2)C3)cc1]

To a solution of (5RS)-2-(4-methylbenzyl)-5-(pyrrolidin-1-ylcarbonyl)-5,6,7,8-tetrahydro[1,2,4]triazolo[4,3-a]pyrazin-3(2H)-one (racemate) (50.0 mg, 85% purity, 124 µmol) in dichloromethane (1.0 ml) was added 1,2-dichloro-4-isocyanatobenzene (28.1 mg, 149 µmol). The reaction mixture was stirred at room temperature for 1 hour. Subsequently, all volatile constituents were removed under reduced pressure and the residue was taken up in acetonitrile/water and purified via preparative HPLC (Chromatorex C18, 10 µm, 125 mm×30 mm; eluent: acetonitrile/water gradient). The product-containing fractions were concentrated under reduced pressure and purified via column chromatography (silica gel, eluent: dichloromethane/methanol gradient). This gave 42.0 mg (64% of theory) of the title compound.

LC-MS (Method 2): $R_t$=1.87 min; MS (ESIpos): m/z=529 [M+H]$^+$ $^1$H-NMR (400 MHz, DMSO-d6) δ [ppm]: 1.637 (0.41), 1.655 (0.55), 1.746 (0.49), 1.761 (0.54), 1.909 (0.69), 1.926 (1.11), 1.942 (0.99), 1.956 (0.61), 2.275 (9.25), 2.967 (0.48), 2.980 (0.43), 3.215 (0.70), 3.233 (0.41), 3.245 (0.59), 3.556 (0.53), 3.563 (0.47), 3.581 (0.79), 3.642 (0.63), 3.658 (0.47), 3.665 (0.42), 3.692 (0.56), 3.703 (0.62), 3.729 (0.64), 3.740 (0.58), 4.292 (1.25), 4.333 (1.39), 4.506 (0.70), 4.542 (0.63), 4.801 (4.59), 4.848 (1.13), 4.965 (1.15), 5.007 (1.03), 7.142 (16.00), 7.333 (1.00), 7.339 (1.01), 7.355 (1.27), 7.361 (1.34), 7.475 (2.43), 7.497 (1.78), 7.731 (2.15), 7.738 (2.10), 9.023 (1.85).

Example 27

(5RS)—N-(2,2-Difluoroethyl)-2-(4-methylbenzyl)-3-oxo-5-(pyrrolidin-1-ylcarbonyl)-2,5,6,8-tetrahydro[1,2,4]triazolo[4,3-a]pyrazine-7(3H)-carboxamide (Racemate)

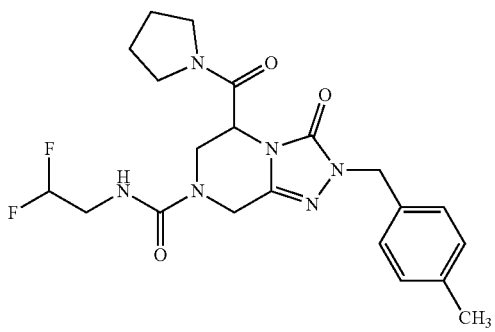 [SMILES: Cc1ccc(Cn2nc3n(c2=O)C(C(=O)N2CCCC2)CN(C(=O)NCC(F)F)C3)cc1]

To a solution of (5RS)-2-(4-methylbenzyl)-5-(pyrrolidin-1-ylcarbonyl)-5,6,7,8-tetrahydro[1,2,4]triazolo[4,3-a]pyrazin-3(2H)-one (racemate) (25.0 mg, 85% purity, 62.2 µmol) in dichloromethane (500 µl) was added 1,1-difluoro-2-isocyanatoethane (11.4 mg, 70% purity, 74.7 µmol). The reaction mixture was stirred at room temperature for 2 hours. Subsequently, all volatile constituents were removed under reduced pressure and the residue was taken up in acetonitrile/water and purified via preparative HPLC (Chromatorex C18, 10 μm, 125 mm×30 mm; eluent: acetonitrile/water gradient). The product-containing fractions were concentrated under reduced pressure, and 21.0 mg (75% of theory) of the title compound was obtained.

LC-MS (Method 2): $R_t$=1.30 min; MS (ESIpos): m/z=449 [M+H]$^+$ $^1$H-NMR (400 MHz, DMSO-d6) δ [ppm]: −0.008 (0.69), 0.008 (0.60), 1.762 (0.70), 1.780 (1.21), 1.791 (0.99), 1.798 (0.96), 1.807 (0.80), 1.919 (0.78), 1.936 (1.07), 1.946 (0.98), 1.953 (0.78), 1.961 (0.68), 2.273 (10.94), 3.179 (0.47), 3.193 (0.60), 3.208 (0.75), 3.226 (0.46), 3.280 (0.66), 3.298 (1.95), 3.313 (14.34), 3.345 (0.80), 3.383 (0.42), 3.394 (0.50), 3.538 (0.61), 3.545 (0.54), 3.563 (0.91), 3.580 (0.41), 3.608 (0.51), 3.627 (1.24), 3.640 (0.60), 3.653 (0.99), 3.664 (0.92), 4.230 (1.62), 4.247 (0.69), 4.254 (0.72), 4.272 (1.93), 4.283 (0.66), 4.290 (0.62), 4.725 (1.46), 4.768 (2.74), 4.785 (5.27), 5.750 (0.48), 5.881 (0.45), 5.891 (0.95), 5.901 (0.46), 6.032 (0.45), 7.132 (16.00), 7.188 (0.60), 7.202 (1.19), 7.216 (0.58).

Example 28

(5RS)—N-tert-Butyl-2-(4-methylbenzyl)-3-oxo-5-(pyrrolidin-1-ylcarbonyl)-2,5,6,8-tetrahydro[1,2,4]triazolo[4,3-a]pyrazine-7(3H)-carboxamide (Racemate)

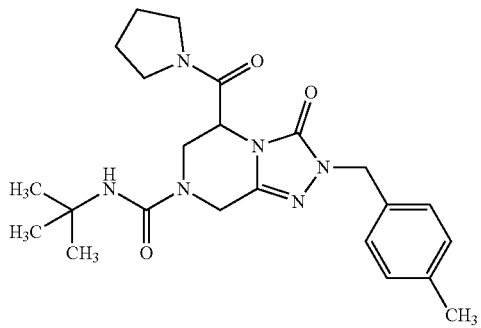 [SMILES: Cc1ccc(Cn2nc3n(c2=O)C(C(=O)N2CCCC2)CN(C(=O)NC(C)(C)C)C3)cc1]

To a solution of (5RS)-2-(4-methylbenzyl)-5-(pyrrolidin-1-ylcarbonyl)-5,6,7,8-tetrahydro[1,2,4]triazolo[4,3-a]pyrazin-3(2H)-one (racemate) (25.0 mg, 85% purity, 62.2 μmol) in dichloromethane (500 μl) was added 2-isocyanato-2-methylpropane (7.40 mg, 74.7 μmol). The reaction mixture was stirred at room temperature for 2 hours. Again, 2-isocyanato-2-methylpropane (7.40 mg, 74.7 μmol) was added and the mixture stirred at room temperature overnight. Subsequently, all volatile constituents were removed under reduced pressure and the residue was taken up in acetonitrile/water and purified via preparative HPLC (Chromatorex C18, 10 μm, 125 mm×30 mm; eluent: acetonitrile/water gradient). The product-containing fractions were concentrated under reduced pressure, and 18.5 mg (67% of theory) of the title compound were obtained.

LC-MS (Method 2): $R_t$=1.53 min; MS (ESIpos): m/z=441 [M+H]$^+$ $^1$H-NMR (400 MHz, DMSO-d6) δ [ppm]: 1.202 (16.00), 1.775 (0.41), 1.793 (0.47), 1.939 (0.51), 1.949 (0.46), 2.274 (5.17), 3.345 (0.56), 3.549 (0.53), 3.558 (0.66), 3.585 (0.41), 4.111 (0.78), 4.153 (0.87), 4.711 (0.40), 4.720 (0.70), 4.780 (2.69), 4.813 (0.63), 6.035 (1.16), 7.135 (8.57).

Example 29

(5RS)-2-{[3-Chloro-4-(trifluoromethyl)pyridin-2-yl]methyl}-5-{[(3S)-3-fluoropyrrolidin-1-yl]carbonyl}-7-isobutyl-5,6,7,8-tetrahydro[1,2,4]triazolo[4,3-a]pyrazin-3(2H)-one (Diastereomer Mixture; 2 Isomers)

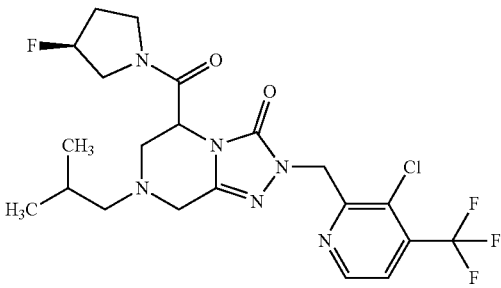 [SMILES: CC(C)CN1Cc2nn(Cc3nccc(C(F)(F)F)c3Cl)c(=O)n2C(C(=O)N2CC[C@H](F)C2)C1]

To a solution of (5RS)-2-{[3-chloro-4-(trifluoromethyl)pyridin-2-yl]methyl}-5-{[(3S)-3-fluoropyrrolidin-1-yl]carbonyl}-5,6,7,8-tetrahydro[1,2,4]triazolo[4,3-a]pyrazin-3(2H)-one (diastereomer mixture; 2 isomers) (70.0 mg, 156 μmol) and 2-methylpropanal (28 μl, 310 μmol) in THF (1.5 ml) was added sodium triacetoxyborohydride (132 mg, 624 μmol). Acetic acid (67 μl) was added and the mixture was stirred at room temperature for 1 hour. Again, 2-methylpropanal (28 μl, 310 μmol) was added and the mixture was stirred at room temperature for a further hour. The reaction mixture was purified via preparative HPLC (Chromatorex C18, 10 μm, 125 mm×30 mm; eluent: acetonitrile/water gradient). The product-containing fractions were concentrated under reduced pressure, and 64.0 mg (81% of theory) of the title compound were obtained.

LC-MS (Method 2): $R_t$=1.79 min; MS (ESIpos): m/z=505 [M+H]$^+$ $^1$H-NMR (400 MHz, DMSO-d6) δ [ppm]: 0.759 (7.26), 0.775 (16.00), 0.789 (12.19), 0.804 (7.51), 0.812 (9.17), 0.817 (8.97), 0.827 (15.02), 0.840 (10.10), 1.722 (0.65), 1.737 (1.47), 1.754 (2.20), 1.771 (2.35), 1.788 (1.84), 1.805 (1.09), 1.823 (0.44), 1.950 (0.50), 1.976 (0.44), 2.093 (1.23), 2.120 (1.19), 2.148 (1.71), 2.160 (2.14), 2.178 (3.41), 2.191 (4.10), 2.199 (3.16), 2.209 (3.98), 2.219 (4.66), 2.236 (4.90), 2.248 (3.38), 2.266 (2.19), 2.328 (0.44), 2.670 (0.45), 2.884 (1.65), 2.924 (3.94), 2.936 (2.79), 2.988 (0.90), 3.001 (0.98), 3.027 (1.37), 3.037 (1.35), 3.058 (1.53), 3.070 (1.72), 3.088 (0.76), 3.102 (0.66), 3.266 (0.77), 3.332 (2.08), 3.357 (3.13), 3.372 (3.12), 3.383 (1.74), 3.412 (2.83), 3.421 (2.92), 3.463 (1.62), 3.485 (1.21), 3.512 (3.87), 3.530 (2.00), 3.551 (3.90), 3.569 (2.96), 3.589 (1.76), 3.607 (2.45), 3.636 (1.02), 3.661 (1.26), 3.679 (2.60), 3.709 (1.22), 3.742 (1.75), 3.765 (1.72), 3.787 (1.13), 3.821 (0.84), 3.883 (1.72), 3.946 (0.80), 3.969 (1.45), 3.992 (0.81), 4.034 (0.48), 4.062 (0.58), 4.092 (0.44), 4.688 (0.81), 4.700 (1.75), 4.713 (0.84), 4.738 (0.93), 4.752 (1.90), 4.765 (0.86), 4.821 (0.81), 4.833 (1.79), 4.849 (1.35), 4.861 (2.33), 4.872 (1.09), 5.136 (1.02), 5.184 (13.68), 5.226 (1.09), 5.258 (1.71), 5.338 (0.77), 5.391 (1.71), 5.470 (0.74), 5.502 (0.70), 7.848 (9.33), 7.861 (9.62), 8.737 (7.79), 8.750 (7.58). (mixture of diastereomers)

Example 30

(5RS)-7-Isobutyl-2-(4-methylbenzyl)-5-(pyrrolidin-1-ylcarbonyl)-5,6,7,8-tetrahydro[1,2,4]triazolo[4,3-a]pyrazin-3(2H)-one (Racemate)

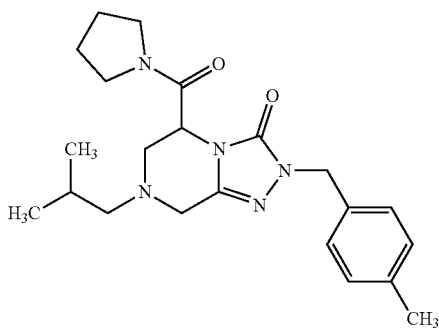 [SMILES: Cc1ccc(Cn2nc3n(c2=O)C(C(=O)N2CCCC2)CN(CC(C)C)C3)cc1]

To an initial charge of (5RS)-2-(4-methylbenzyl)-5-(pyrrolidin-1-ylcarbonyl)-5,6,7,8-tetrahydro[1,2,4]triazolo[4,3-a]pyrazin-3(2H)-one (racemate) (40.0 mg, 117 μmol) and 2-methylpropanal (21 μl, 230 μmol) in THF (1.0 ml) were added sodium triacetoxyborohydride (99.3 mg, 469 μmol) and acetic acid (50 μl). After 1 h at room temperature, water and ethyl acetate were added and the mixture was stirred at room temperature overnight. The organic phase was removed and the aqueous phase was extracted three times with ethyl acetate. The combined organic phases were washed with saturated aqueous sodium chloride solution, dried over magnesium sulfate and filtered, and the filtrate was concentrated. The residue was purified via preparative HPLC (Chromatorex C18, 10 μm, 125 mm×30 mm; eluent: acetonitrile/water gradient). The product-containing fractions were concentrated under reduced pressure, and 38.2 mg (82% of theory) of the title compound were obtained.

LC-MS (Method 2): $R_t$=1.76 min; MS (ESIpos): m/z=398 [M+H]$^+$ $^1$H-NMR (400 MHz, DMSO-d6) δ [ppm]: 0.770 (4.70), 0.787 (4.84), 0.815 (4.66), 0.831 (4.76), 1.732 (0.66), 1.739 (0.42), 1.751 (1.06), 1.769 (0.96), 1.786 (0.79), 1.802 (0.69), 1.818 (0.58), 1.882 (0.67), 1.897 (0.97), 1.911 (0.79), 1.926 (0.52), 2.137 (0.45), 2.157 (0.44), 2.167 (0.97), 2.188 (0.92), 2.206 (0.98), 2.223 (0.94), 2.236 (0.47), 2.253 (0.46), 2.274 (9.70), 2.919 (1.13), 2.930 (1.69), 2.941 (1.08), 3.220 (0.56), 3.232 (0.54), 3.239 (0.47), 3.252 (0.40), 3.311 (1.19), 3.324 (1.67), 3.347 (0.91), 3.362 (1.93), 3.376 (0.64), 3.408 (0.64), 3.414 (0.45), 3.426 (0.40), 3.433 (0.67), 3.523 (1.63), 3.561 (1.15), 3.653 (0.52), 3.662 (0.41), 3.669 (0.40), 3.676 (0.41), 4.714 (0.68), 4.726 (1.60), 4.738 (0.69), 4.765 (4.67), 7.134 (16.00).

Example 31

(5RS)-7-Cyclobutyl-2-(4-methylbenzyl)-5-(pyrrolidin-1-ylcarbonyl)-5,6,7,8-tetrahydro[1,2,4]triazolo[4,3-a]pyrazin-3(2H)-one (Racemate)

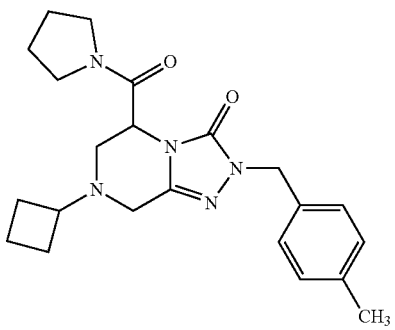 [SMILES: Cc1ccc(Cn2nc3n(c2=O)C(C(=O)N2CCCC2)CN(C2CCC2)C3)cc1]

To an initial charge of (5RS)-2-(4-methylbenzyl)-5-(pyrrolidin-1-ylcarbonyl)-5,6,7,8-tetrahydro[1,2,4]triazolo[4,3-a]pyrazin-3(2H)-one (racemate) (50.0 mg, 146 μmol) and cyclobutanone (22 μl, 290 μmol) in THF (1.0 ml) were added sodium triacetoxyborohydride (124 mg, 586 μmol) and acetic acid (63 μl, 1.1 mmol). The reaction mixture was stirred at room temperature for 1 hour and then diluted with water. The reaction mixture was purified via preparative HPLC (Chromatorex C18, 10 μm, 125 mm×30 mm; eluent: acetonitrile/water gradient). The product-containing fractions were concentrated under reduced pressure, and 37.8 mg (65% of theory) of the title compound were obtained.

LC-MS (Method 2): $R_t$=1.61 min; MS (ESIpos): m/z=396 [M+H]$^+$ $^1$H-NMR (400 MHz, DMSO-d6) δ [ppm]: 1.576 (0.54), 1.582 (0.61), 1.602 (1.20), 1.618 (1.39), 1.626 (1.19), 1.644 (0.95), 1.673 (0.47), 1.696 (0.80), 1.720 (1.05), 1.742 (1.09), 1.761 (1.60), 1.780 (2.15), 1.797 (2.21), 1.813 (1.76), 1.829 (0.67), 1.870 (0.45), 1.887 (1.15), 1.903 (1.65), 1.916 (1.49), 1.930 (1.27), 1.946 (1.04), 1.962 (0.80), 1.972 (0.79), 1.998 (0.82), 2.009 (0.70), 2.017 (0.72), 2.274 (15.01), 2.697 (0.88), 2.712 (0.95), 2.729 (1.13), 2.743 (1.12), 2.913 (1.09), 2.926 (1.25), 2.945 (1.19), 2.970 (1.29), 2.989 (0.85), 3.233 (0.50), 3.250 (0.73), 3.263 (1.20), 3.283 (2.39), 3.296 (1.64), 3.322 (4.29), 3.336 (1.43), 3.355 (1.72), 3.374 (1.17), 3.383 (4.02), 3.405 (1.44), 3.421 (2.04), 3.430 (1.31), 3.447 (0.56), 3.648 (0.56), 3.664 (0.96), 3.673 (0.71), 3.680 (0.73), 3.688 (0.83), 3.705 (0.42), 4.695 (1.12), 4.708 (2.32), 4.722 (1.11), 4.763 (8.25), 7.106 (0.82), 7.128 (16.00), 7.151 (0.76).

Example 32

(5RS)-2-(4-Methylbenzyl)-5-(pyrrolidin-1-ylcarbonyl)-7-[4-(trifluoromethyl)benzoyl]-5,6,7,8-tetrahydro[1,2,4]triazolo[4,3-a]pyrazin-3(2H)-one (Racemate)

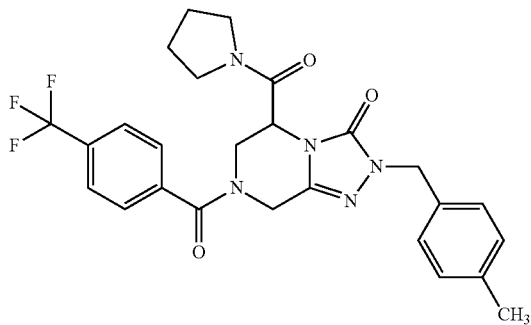 [SMILES: Cc1ccc(Cn2nc3n(c2=O)C(C(=O)N2CCCC2)CN(C(=O)c2ccc(C(F)(F)F)cc2)C3)cc1]

To a solution of (5RS)-2-(4-methylbenzyl)-5-(pyrrolidin-1-ylcarbonyl)-5,6,7,8-tetrahydro[1,2,4]triazolo[4,3-a]pyrazin-3(2H)-one (racemate) (50.0 mg, 85% purity, 124 µmol) in dichloromethane (1.0 ml) and N,N-diisopropylethylamine (43 µl, 250 µmol) was added 4-(trifluoromethyl)benzoyl chloride (20 µl, 140 µmol). The reaction mixture was stirred at room temperature for 1 hour. Subsequently, all volatile constituents were removed under reduced pressure and the residue was taken up in acetonitrile/water and purified via preparative HPLC (Chromatorex C18, 10 µm, 125 mm×30 mm; eluent: acetonitrile/water gradient). The product-containing fractions were concentrated under reduced pressure, and 51.2 mg (80% of theory) of the title compound were obtained.

LC-MS (Method 2): $R_t$=1.75 min; MS (ESIpos): m/z=514 [M+H]$^+$ $^1$H-NMR (400 MHz, DMSO-d6) δ [ppm]: −0.008 (1.84), 0.008 (1.61), 1.405 (1.53), 1.731 (1.57), 1.969 (0.42), 2.279 (16.00), 2.523 (0.98), 2.664 (0.87), 2.669 (0.85), 3.180 (1.36), 3.397 (0.94), 3.673 (0.49), 3.906 (2.29), 4.235 (0.87), 4.278 (1.07), 4.769 (2.18), 4.814 (4.18), 4.854 (0.75), 5.246 (0.90), 5.288 (0.84), 7.146 (13.34), 7.522 (2.71), 7.539 (3.38), 7.851 (5.25), 7.871 (4.59).

Example 33

(5RS)-5-{[(3S)-3-Fluoropyrrolidin-1-yl]carbonyl}-2-[4-fluoro-3-(trifluoromethyl)benzyl]-7-(4,4,4-trifluorobutanoyl)-5,6,7,8-tetrahydro[1,2,4]triazolo[4,3-a]pyrazin-3(2H)-one (Isomer 1)

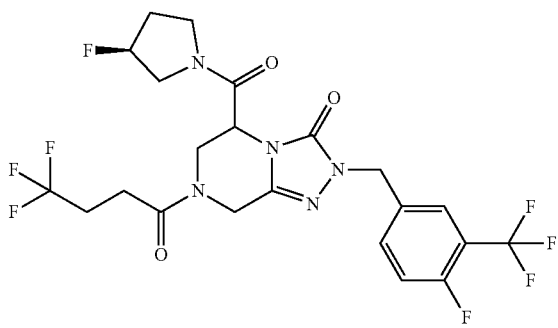 [SMILES: O=C(CCC(F)(F)F)N1Cc2nn(Cc3ccc(F)c(C(F)(F)F)c3)c(=O)n2C(C(=O)N2CC[C@H](F)C2)C1]

To a solution of (5RS)-5-{[(3S)-3-fluoropyrrolidin-1-yl]carbonyl}-2-[4-fluoro-3-(trifluoromethyl)benzyl]-5,6,7,8-tetrahydro[1,2,4]triazolo[4,3-a]pyrazin-3(2H)-one (isomer 2) (80.0 mg, 185 µmol) in dichloromethane (2.0 ml) and N,N-diisopropylethylamine (65 µl, 370 µmol) was added 4,4,4-trifluorobutanoyl chloride (32.7 mg, 204 µmol). The reaction mixture was stirred at room temperature overnight. 4,4,4-Trifluorobutanoyl chloride (32.7 mg, 204 µmol) was added and the mixture was stirred at room temperature for a further 24 hours. The reaction mixture was purified via preparative HPLC (Chromatorex C18, 10 µm, 125 mm×30 mm; eluent: acetonitrile/water gradient). The product-containing fractions were concentrated under reduced pressure, and 35.4 mg (34% of theory) of the title compound were obtained.

LC-MS (Method 2): $R_t$=1.71 min; MS (ESIpos): m/z=556 [M+H]$^+$ $^1$H-NMR (400 MHz, DMSO-d6) δ [ppm]: −0.149 (0.46), 0.146 (0.51), 1.235 (1.46), 1.982 (0.60), 2.161 (2.87), 2.179 (2.71), 2.203 (2.76), 2.218 (2.58), 2.242 (1.84), 2.326 (1.01), 2.366 (0.70), 2.447 (4.19), 2.459 (4.30), 2.613 (2.39), 2.632 (2.90), 2.709 (0.62), 2.739 (0.76), 2.778 (1.87), 2.795 (1.63), 2.819 (1.76), 2.836 (1.01), 2.859 (0.63), 3.368 (2.63), 3.385 (2.46), 3.457 (2.44), 3.488 (4.11), 3.538 (1.90), 3.584 (2.19), 3.745 (1.54), 3.762 (1.70), 3.788 (0.94), 3.900 (2.74), 3.912 (2.00), 3.925 (2.25), 3.939 (3.30), 3.951 (1.95), 3.972 (1.68), 3.997 (3.25), 4.021 (2.28), 4.072 (1.62), 4.102 (0.92), 4.135 (3.60), 4.146 (2.57), 4.177 (3.77), 4.188 (2.85), 4.290 (1.59), 4.323 (2.70), 4.358 (1.79), 4.472 (2.06), 4.515 (2.47), 4.632 (0.82), 4.680 (0.89), 4.716 (0.82), 4.890 (2.11), 4.932 (2.06), 4.962 (16.00), 5.012 (2.70), 5.034 (5.09), 5.045 (5.93), 5.075 (2.43), 5.088 (3.19), 5.268 (1.73), 5.400 (2.00), 5.519 (0.71), 5.551 (1.14), 5.753 (2.12), 7.491 (3.31), 7.513 (6.61), 7.539 (5.42), 7.599 (3.81), 7.696 (4.76), 7.711 (5.58).

Example 34

(5RS)-7-(Cyclopropylcarbonyl)-5-{[(3S)-3-fluoropyrrolidin-1-yl]carbonyl}-2-[4-fluoro-3-(trifluoromethyl)benzyl]-5,6,7,8-tetrahydro[1,2,4]triazolo[4,3-a]pyrazin-3(2H)-one (Isomer 1)

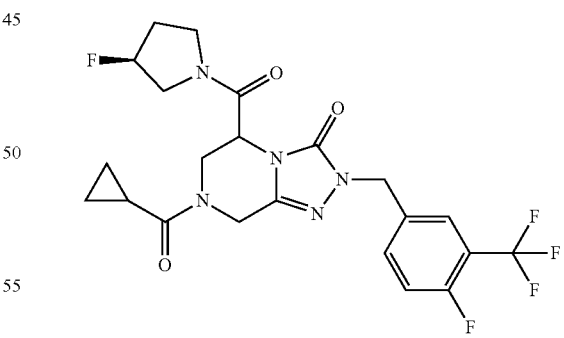

To a solution of (5RS)-5-{[(3S)-3-fluoropyrrolidin-1-yl]carbonyl}-2-[4-fluoro-3-(trifluoromethyl)benzyl]-5,6,7,8-tetrahydro[1,2,4]triazolo[4,3-a]pyrazin-3(2H)-one (isomer 2) (70.0 mg, 162 µmol) in dichloromethane (1.5 ml) and N,N-diisopropylethylamine (57 µl, 320 µmol) was added cyclopropanecarbonyl chloride (16 µl, 180 µmol). The reaction mixture was stirred at room temperature for 2 hours. The reaction mixture was purified via preparative HPLC (Chromatorex C18, 10 µm, 125 mm×30 mm; eluent:

acetonitrile/water gradient). The product-containing fractions were concentrated under reduced pressure, and 69.5 mg (86% of theory) of the title compound were obtained.

LC-MS (Method 2): $R_t$=1.51 min; MS (ESIpos): m/z=500 [M+H]$^+$ $^1$H-NMR (400 MHz, DMSO-d6) δ [ppm]: 0.590 (1.68), 0.681 (4.21), 0.765 (2.35), 1.902 (1.43), 2.020 (0.73), 2.073 (0.73), 2.165 (1.05), 2.220 (0.99), 2.273 (1.53), 2.327 (0.44), 2.670 (0.41), 3.377 (1.06), 3.394 (1.05), 3.479 (1.11), 3.512 (2.57), 3.593 (2.56), 3.775 (0.90), 3.794 (0.85), 3.936 (1.41), 3.966 (2.61), 3.987 (2.65), 4.010 (1.36), 4.027 (1.34), 4.051 (2.05), 4.087 (2.45), 4.115 (0.99), 4.592 (0.97), 4.628 (1.08), 4.706 (1.77), 4.743 (1.45), 4.967 (16.00), 5.055 (2.26), 5.118 (1.87), 5.159 (1.94), 5.273 (1.00), 5.374 (1.74), 5.405 (1.05), 5.506 (1.48), 7.492 (1.88), 7.515 (3.89), 7.540 (3.12), 7.597 (2.69), 7.702 (3.48), 7.719 (3.64).

Example 35

(5RS)-5-{[(3S)-3-Fluoropyrrolidin-1-yl]carbonyl}-7-methyl-2-{[6-(trifluoromethyl)pyridin-3-yl]methyl}-5,6,7,8-tetrahydro[1,2,4]triazolo[4,3-a]pyrazin-3(2H)-one (Diastereomer Mixture; 2 Isomers)

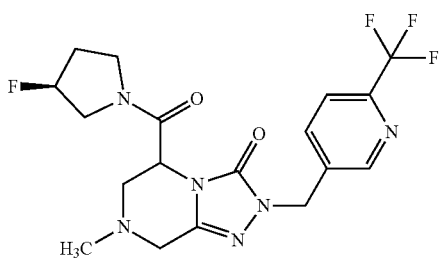 [SMILES: CN1Cc2nn(Cc3ccc(C(F)(F)F)nc3)c(=O)n2C(C(=O)N2CC[C@H](F)C2)C1]

(5RS)-5-{[(3S)-3-Fluoropyrrolidin-1-yl]carbonyl}-2-{[6-(trifluoromethyl)pyridin-3-yl]methyl}-5,6,7,8-tetrahydro[1,2,4]triazolo[4,3-a]pyrazin-3(2H)-one (diastereomer mixture; 2 isomers) (29.0 mg, 70.0 µmol) was initially charged in THF (5.0 ml). Formaldehyde (16 µl, 37% in water, 210 µmol) and sodium triacetoxyborohydride (59.3 mg, 280 µmol) were then added. After stirring overnight, water and acetic acid were added to the reaction mixture at room temperature. The mixture was purified via preparative HPLC (Chromatorex C18, 10 µm, 125 mm×30 mm; eluent: acetonitrile/water gradient). The product-containing fractions were concentrated under reduced pressure, and 5.10 mg (17% of theory) of the title compound were obtained.

LC-MS (Method 1): $R_t$=0.62 min; MS (ESIpos): m/z=429 [M+H]$^+$ $^1$H-NMR (500 MHz, METHANOL-d4) δ [ppm]: 1.991 (0.44), 2.156 (0.43), 2.185 (0.50), 2.193 (0.51), 2.214 (0.67), 2.225 (0.57), 2.233 (0.60), 2.240 (0.52), 2.248 (0.56), 2.258 (0.63), 2.268 (0.69), 2.281 (0.46), 2.294 (0.59), 2.316 (0.50), 2.332 (0.42), 2.350 (0.51), 2.365 (0.57), 2.381 (0.43), 2.426 (6.34), 2.435 (8.30), 2.439 (16.00), 2.452 (0.99), 2.861 (0.94), 2.899 (0.78), 2.924 (0.45), 2.935 (0.44), 2.977 (0.84), 2.988 (0.92), 2.995 (1.48), 3.003 (1.38), 3.013 (1.29), 3.018 (0.80), 3.029 (0.82), 3.032 (0.82), 3.043 (0.68), 3.084 (0.76), 3.094 (0.81), 3.110 (0.99), 3.120 (1.01), 3.132 (0.63), 3.143 (0.63), 3.157 (0.42), 3.168 (0.41), 3.359 (0.73), 3.369 (1.05), 3.390 (1.09), 3.396 (1.62), 3.426 (2.17), 3.461 (1.18), 3.474 (0.46), 3.578 (1.28), 3.583 (0.82), 3.598 (1.54), 3.606 (2.25), 3.621 (1.42), 3.629 (1.08), 3.636 (1.32), 3.652 (1.12), 3.661 (0.85), 3.672 (1.11), 3.685 (0.94), 3.692 (0.83), 3.705 (1.29), 3.715 (0.83), 3.728 (2.06), 3.761 (0.42), 3.768 (0.45), 3.785 (0.54), 3.792 (0.44), 3.817 (0.76), 3.828 (0.67), 3.840 (1.46), 3.848 (1.02), 3.862 (0.99), 3.866 (0.92), 3.882 (0.94), 3.901 (0.80), 3.927 (0.70), 4.014 (0.56), 4.033 (0.96), 4.052 (0.47), 4.715 (0.67), 4.782 (1.00), 4.793 (1.85), 4.805 (2.17), 4.872 (1.87), 4.882 (1.35), 4.925 (0.83), 4.935 (1.56), 4.945 (0.75), 5.039 (1.07), 5.071 (3.48), 5.094 (2.81), 5.101 (3.10), 5.126 (0.92), 5.133 (1.29), 5.246 (0.47), 5.255 (0.54), 5.262 (0.63), 5.294 (1.32), 5.318 (0.52), 5.352 (0.78), 5.361 (0.69), 6.807 (0.69), 6.828 (0.76), 7.788 (3.64), 7.805 (4.87), 7.822 (0.76), 7.963 (2.13), 7.979 (1.90), 8.693 (3.44), 8.766 (0.59). (mixture of diastereomers)

Example 36

[(5-Chloropyridin-3-yl)methyl]-7-{[(1RS)-2,2-difluorocyclopropyl]methyl}-5-{[(3S)-3-fluoropyrrolidin-1-yl]carbonyl}-5,6,7,8-tetrahydro[1,2,4]triazolo[4,3-a]pyrazin-3(2H)-one (Diastereomer Mixture; 4 Isomers)

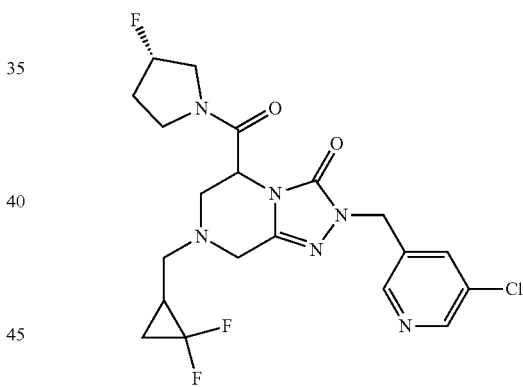

To an initial charge of (5RS)-2-[(5-chloropyridin-3-yl)methyl]-5-{[(3S)-3-fluoropyrrolidin-1-yl]carbonyl}-5,6,7,8-tetrahydro[1,2,4]triazolo[4,3-a]pyrazin-3(2H)-one (diastereomer mixture; 2 isomers) (100 mg, 263 µmol) in THF (5.0 ml) were added N,N-diisopropylethylamine (180 µl, 1.1 mmol) and (2R)-2-(bromomethyl)-1,1-difluorocyclopropane (67.4 mg, 394 µmol). The reaction mixture was stirred at room temperature overnight. Again, N,N-diisopropylethylamine (180 µl, 1.1 mmol) and (2R)-2-(bromomethyl)-1,1-difluorocyclopropane (67.4 mg, 394 µmol) were added and the reaction mixture was stirred at 60° C. for 24 hours and at 70° C. for 24 hours. Subsequently, the reaction mixture was concentrated under reduced pressure and the residue was purified via preparative HPLC (Chromatorex C18, 10 µm, 125 mm×30 mm; eluent: acetonitrile/water gradient). The product-containing fractions were concentrated under

Example 37

[(5-Chloropyridin-3-yl)methyl]-7-{[(1 RS)-2,2-difluorocyclopropyl]methyl}-5-{[(3S)-3-fluoropyrrolidin-1-yl]carbonyl}-5,6,7,8-tetrahydro[1,2,4]triazolo[4,3-a]pyrazin-3(2H)-one (Isomer 1)

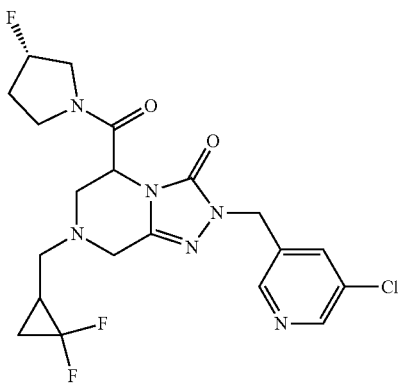 [SMILES: O=C(C1CN(CC2CC2(F)F)Cc2nn(Cc3cncc(Cl)c3)c(=O)n21)N1CC[C@H](F)C1]

(5RS)-2-[(5-Chloropyridin-3-yl)methyl]-7-{[(1 RS)-2,2-difluorocyclopropyl]methyl}-5-{[(3S)-3-fluoropyrrolidin-1-yl]carbonyl}-5,6,7,8-tetrahydro[1,2,4]triazolo[4,3-a]pyrazin-3(2H)-one (diastereomer mixture, 4 isomers) was separated by chiral HPLC [sample preparation: 16 mg dissolved in 3 ml (acetonitrile/ethanol, 1:1); injection volume: 0.5 ml; column: Daicel Chiralpak® AZ-H, 250×30 mm; eluent: n-heptane/ethanol 1:1+0.2% diethylamine; flow rate: 40 ml/min; temperature 40° C.; UV detection: 220 nm]. After the separation, 1.0 mg of isomer 1 was isolated.

Isomer 1:

Analytical chiral HPLC: $R_t$=3.1 min, d.e.=94% [column: Daicel Chiralpak® AZ-3 50×4.6 mm; eluent: n-heptane/ethanol 1:1+0.2% diethylamine; flow rate: 1 ml/min; UV detection: 220 nm].

LC-MS (Method 2): $R_t$=1.33 min; MS (ESIpos): m/z=471 [M+H]$^+$ $^1$H-NMR (500 MHz, DMSO-d6) δ [ppm]: −0.064 (2.42), −0.007 (9.86), 0.007 (7.44), 0.067 (4.28), 0.844 (2.05), 0.859 (2.23), 0.998 (1.12), 1.056 (2.23), 1.121 (6.33), 1.135 (12.84), 1.150 (6.14), 1.160 (5.40), 1.175 (9.30), 1.189 (5.02), 1.236 (5.58), 1.601 (1.67), 1.889 (1.30), 1.988 (16.00), 2.237 (0.93), 2.361 (2.98), 2.582 (2.42), 2.596 (2.42), 2.635 (3.91), 2.723 (1.86), 2.867 (2.79), 3.025 (1.86), 3.056 (2.05), 3.137 (1.30), 3.452 (2.98), 3.481 (3.35), 3.492 (3.16), 3.521 (4.28), 3.537 (2.98), 3.568 (2.23), 3.648 (3.91), 3.658 (3.16), 3.678 (3.16), 3.988 (1.86), 4.008 (2.05), 4.022 (3.91), 4.037 (3.72), 4.051 (1.86), 4.074 (1.12), 4.893 (2.60), 4.902 (2.98), 4.912 (3.72), 4.944 (7.26), 5.283 (1.12), 5.390 (1.30), 5.471 (1.12), 7.777 (5.40), 7.782 (5.21), 8.442 (6.33), 8.571 (5.58).

Example 38

(5RS)-2-[(5-Chloropyridin-3-yl)methyl]-5-{[(3S)-3-fluoropyrrolidin-1-yl]carbonyl}-7-methyl-5,6,7,8-tetrahydro[1,2,4]triazolo[4,3-a]pyrazin-3(2H)-one (Diastereomer Mixture; 2 Isomers)

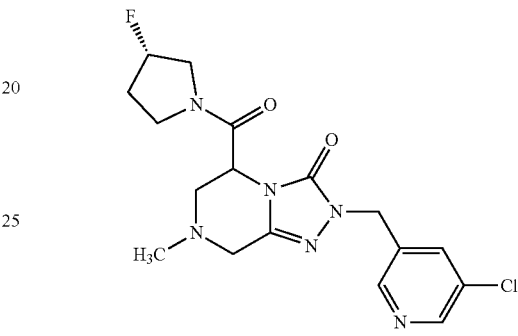

To an initial charge of (5S)-2-[(5-chloropyridin-3-yl)methyl]-5-{[(3S)-3-fluoropyrrolidin-1-yl]carbonyl}-5,6,7,8-tetrahydro[1,2,4]triazolo[4,3-a]pyrazin-3(2H)-one (diastereomer mixture; 2 isomers) (100 mg, 97% purity, 255 μmol) in N,N-diisopropylethylamine (180 μl, 1.0 mmol) was added methyl iodide (24 μl, 380 μmol). The reaction mixture was stirred at room temperature overnight. Subsequently, the reaction mixture was concentrated under reduced pressure and the residue was purified via preparative HPLC (Chromatorex C18, 10 μm, 125 mm×30 mm; eluent: acetonitrile/water gradient). The product-containing fractions were concentrated under reduced pressure, and 15.0 mg (97% purity, 14% of theory) of the title compound were obtained.

LC-MS (Method 1): $R_t$=0.53 min; MS (ESIpos): m/z=395 [M+H]$^+$ $^1$H-NMR (400 MHz, DMSO-d6) δ [ppm]: 0.938 (0.72), 0.954 (0.68), 2.099 (0.76), 2.113 (0.76), 2.144 (0.78), 2.241 (0.74), 2.302 (6.87), 2.313 (16.00), 2.365 (0.43), 2.669 (0.70), 2.688 (0.47), 2.709 (0.43), 2.880 (1.23), 2.891 (0.98), 2.925 (1.40), 2.937 (1.97), 2.981 (0.64), 2.993 (0.62), 3.029 (0.51), 3.217 (0.96), 3.254 (1.97), 3.270 (0.94), 3.291 (2.22), 3.354 (1.37), 3.388 (0.90), 3.405 (0.74), 3.434 (0.41), 3.500 (1.54), 3.531 (1.66), 3.546 (2.03), 3.561 (1.80), 3.571 (1.62), 3.585 (1.60), 3.599 (1.46), 3.668 (1.17), 3.691 (1.03), 3.731 (0.88), 3.755 (0.84), 3.809 (0.86), 3.881 (0.70), 3.940 (0.47), 3.963 (0.82), 3.988 (0.76), 4.046 (0.45), 4.722 (0.70), 4.734 (0.41), 4.761 (0.47), 4.774 (1.00), 4.856 (0.53), 4.866 (1.11), 4.879 (1.07), 4.892 (1.33), 4.939 (7.84), 4.994 (0.49), 5.270 (0.72), 5.347 (0.53), 5.393 (0.70), 5.479 (0.55), 7.767 (3.28), 8.433 (4.27), 8.571 (3.14). (mixture of diastereomers)

Example 39

(5RS)-2-[(5-Chloropyridin-3-yl)methyl]-5-{[(3S)-3-fluoropyrrolidin-1-yl]carbonyl}-7-methyl-5,6,7,8-tetrahydro[1,2,4]triazolo[4,3-a]pyrazin-3(2H)-one (Isomer 1)

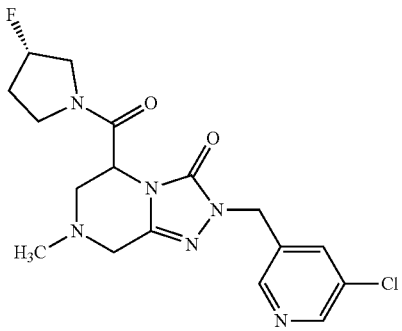 [SMILES: CN1Cc2nn(Cc3cncc(Cl)c3)c(=O)n2C(C(=O)N2CC[C@H](F)C2)C1]

(5RS)-2-[(5-Chloropyridin-3-yl)methyl]-5-{[(3S)-3-fluoropyrrolidin-1-yl]carbonyl}-7-methyl-5,6,7,8-tetrahydro[1,2,4]triazolo[4,3-a]pyrazin-3(2H)-one (diastereomer mixture, 2 isomers) was separated by chiral HPLC [sample preparation: 15 mg dissolved in 2 ml (acetonitrile/ethanol, 1:1); injection volume: 0.2 ml; column: Daicel Chiralpak® AS-H, 250×20 mm; eluent: n-heptane/ethanol 70:30+0.2% diethylamine; flow rate: 20 ml/min; temperature 28° C.; UV detection: 220 nm]. After the separation, 1.9 mg of isomer 1, which eluted first, and 2.2 mg of isomer 2, which eluted later, were isolated.

Isomer 1:

Analytical chiral HPLC: $R_t$=1.2 min, d.e.=100% [column: Daicel Chiralpak® AS-3 50×4.6 mm; eluent: n-heptane/ethanol 1:1+0.2% diethylamine; flow rate: 1 ml/min; UV detection: 220 nm].

$^1$H-NMR (500 MHz, METHANOL-d4) δ [ppm]: 1.284 (2.69), 1.291 (1.03), 1.298 (5.12), 1.313 (2.66), 2.203 (0.41), 2.213 (0.49), 2.226 (0.41), 2.230 (0.44), 2.245 (0.44), 2.266 (0.60), 2.278 (0.43), 2.285 (0.49), 2.290 (0.61), 2.313 (0.60), 2.323 (0.48), 2.347 (0.66), 2.358 (0.62), 2.415 (9.84), 2.427 (16.00), 2.938 (0.97), 2.949 (1.02), 2.964 (1.50), 2.974 (1.44), 2.983 (1.01), 2.993 (0.95), 3.019 (0.81), 3.025 (1.10), 3.033 (2.48), 3.048 (2.01), 3.061 (0.95), 3.077 (1.25), 3.088 (1.26), 3.103 (0.90), 3.113 (0.86), 3.359 (1.15), 3.390 (1.67), 3.396 (1.92), 3.427 (2.43), 3.570 (0.44), 3.584 (2.86), 3.593 (0.93), 3.602 (2.09), 3.615 (2.33), 3.623 (0.42), 3.633 (1.38), 3.652 (1.09), 3.659 (1.25), 3.669 (1.44), 3.677 (1.39), 3.684 (1.16), 3.698 (2.02), 3.723 (3.08), 3.775 (0.40), 3.848 (0.42), 4.009 (0.92), 4.028 (1.71), 4.046 (0.85), 4.060 (0.44), 4.081 (0.51), 4.106 (0.41), 4.845 (1.79), 4.866 (0.96), 4.909 (1.36), 4.920 (2.67), 4.930 (1.29), 4.955 (1.12), 4.987 (5.96), 5.000 (5.48), 5.032 (1.03), 5.256 (1.03), 5.312 (0.62), 5.360 (0.91), 5.363 (0.91), 5.417 (0.62), 7.845 (3.45), 7.850 (2.92), 8.472 (3.49), 8.490 (3.40), 8.493 (3.28).

Example 40

(5RS)-2-[(5-Chloropyridin-3-yl)methyl]-5-{[(3S)-3-fluoropyrrolidin-1-yl]carbonyl}-7-methyl-5,6,7,8-tetrahydro[1,2,4]triazolo[4,3-a]pyrazin-3(2H)-one (Isomer 2)

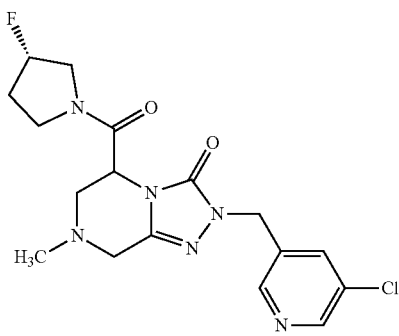 [SMILES: CN1Cc2nn(Cc3cncc(Cl)c3)c(=O)n2C(C(=O)N2CC[C@H](F)C2)C1]

(5RS)-2-[(5-Chloropyridin-3-yl)methyl]-5-{[(3S)-3-fluoropyrrolidin-1-yl]carbonyl}-7-methyl-5,6,7,8-tetrahydro[1,2,4]triazolo[4,3-a]pyrazin-3(2H)-one (diastereomer mixture, 2 isomers) was separated by chiral HPLC [sample preparation: 15 mg dissolved in 2 ml (acetonitrile/ethanol, 1:1); injection volume: 0.2 ml; column: Daicel Chiralpak® AS-H, 250×20 mm; eluent: n-heptane/ethanol 70:30+0.2% diethylamine; flow rate: 20 ml/min; temperature 28° C.; UV detection: 220 nm]. After the separation, 1.9 mg of isomer 1, which eluted first, and 2.2 mg of isomer 2, which eluted later, were isolated.

Isomer 2:

Analytical chiral HPLC: $R_t$=1.43 min, d.e.=100% [column: Daicel Chiralpak® AS-3 50×4.6 mm; eluent: n-heptane/ethanol 1:1+0.2% diethylamine; flow rate: 1 ml/min; UV detection: 220 nm].

$^1$H-NMR (500 MHz, METHANOL-d4) δ [ppm]: 0.903 (0.44), 0.912 (0.46), 0.915 (0.44), 0.926 (0.60), 0.940 (0.52), 1.279 (1.12), 1.284 (4.20), 1.291 (1.57), 1.298 (8.14), 1.313 (4.19), 1.323 (0.56), 2.154 (0.42), 2.183 (0.42), 2.206 (0.66), 2.221 (0.44), 2.224 (0.46), 2.235 (0.48), 2.239 (0.52), 2.243 (0.55), 2.246 (0.62), 2.257 (0.60), 2.260 (0.56), 2.268 (0.47), 2.274 (0.44), 2.286 (0.63), 2.367 (0.55), 2.373 (0.52), 2.377 (0.52), 2.424 (15.48), 2.427 (16.00), 2.862 (0.90), 2.873 (0.93), 2.887 (1.09), 2.899 (1.07), 2.942 (0.83), 2.953 (0.86), 2.967 (1.12), 2.978 (1.09), 3.018 (0.93), 3.033 (2.59), 3.048 (2.53), 3.062 (0.85), 3.102 (0.90), 3.113 (0.98), 3.125 (1.26), 3.136 (1.29), 3.149 (0.79), 3.160 (0.77), 3.393 (1.32), 3.424 (2.00), 3.429 (1.93), 3.443 (0.70), 3.452 (1.09), 3.461 (2.20), 3.474 (0.63), 3.489 (0.62), 3.493 (0.52), 3.501 (0.48), 3.523 (0.54), 3.530 (0.55), 3.556 (2.51), 3.568 (0.59), 3.581 (2.43), 3.587 (1.79), 3.597 (0.67), 3.604 (0.73), 3.611 (1.65), 3.808 (1.32), 3.811 (1.29), 3.823 (1.09), 3.826 (1.21), 3.835 (1.01), 3.846 (2.14), 3.857 (1.07), 3.873 (2.03), 3.891 (1.77), 3.896 (1.85), 3.921 (1.12), 3.962 (0.67), 3.969 (0.67), 4.768 (1.26), 4.779 (2.38), 4.790 (1.44), 4.848 (3.77), 4.951 (1.17), 4.983 (6.48), 4.996 (7.08), 5.027 (1.30), 5.233 (0.50), 5.239 (0.83), 5.246 (0.47), 5.346 (1.42), 5.454 (0.83), 7.843 (3.21), 7.848 (3.22), 8.471 (2.89), 8.493 (2.94).

Example 41

(5RS)-5-{[(3S)-3-Fluoropyrrolidin-1-yl]carbonyl}-2-{[3-fluoro-2-(trifluoromethyl)pyridin-4-yl]methyl}-5,6,7,8-tetrahydro[1,2,4]triazolo[4,3-a]pyrazin-3(2H)-one (Diastereomer Mixture; 2 Isomers)

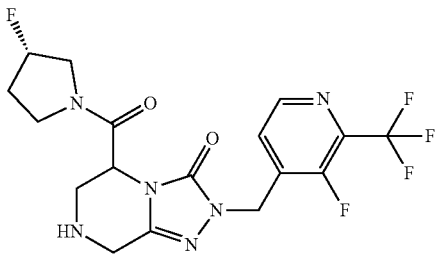 [SMILES: O=C(C1CNCc2nn(Cc3ccnc(C(F)(F)F)c3F)c(=O)n21)N1CC[C@H](F)C1]

To a solution of tert-butyl (5RS)-5-{[(3S)-3-fluoropyrrolidin-1-yl]carbonyl}-2-{[3-fluoro-2-(trifluoromethyl)pyridin-4-yl]methyl}-3-oxo-2,5,6,8-tetrahydro[1,2,4]triazolo[4,3-a]pyrazin-7(3H)-carboxylate (diastereomer mixture; 2 isomers) (36.0 mg, 67.6 µmol) in dichloromethane (2.0 ml) at room temperature was added trifluoroacetic acid (400 µl, 5.2 mmol). After the reaction mixture had been stirred at room temperature overnight, the solvent was removed under reduced pressure. The residue was dissolved in ethyl acetate and water was added. The organic phase was removed and the aqueous phase was extracted three times with ethyl acetate. The combined organic phases were dried over sodium sulfate and filtered, and the filtrate was concentrated. 29.0 mg (99% of theory) of the title compound were obtained.

LC-MS (Method 2): $R_t$=1.03 min; MS (ESIpos): m/z=433 [M+H]$^+$ $^1$H-NMR (500 MHz, DMSO-d6) δ [ppm]: −0.120 (1.29), −0.007 (16.00), 0.006 (8.84), 0.117 (1.15), 1.160 (1.85), 1.175 (3.77), 1.189 (1.96), 1.227 (2.45), 1.236 (2.34), 1.258 (0.84), 1.736 (0.70), 1.988 (6.39), 2.361 (1.71), 2.518 (3.91), 2.522 (2.86), 2.635 (1.89), 3.604 (8.98), 4.008 (0.84), 4.022 (1.54), 4.037 (1.71), 4.051 (0.70), 4.073 (0.63), 4.247 (0.63), 5.139 (1.05), 5.152 (1.36), 5.160 (1.22), 5.315 (0.42), 5.418 (0.45), 7.639 (1.19), 8.588 (1.92), 8.598 (1.85). (mixture of diastereomers)

Example 42

(5RS)-5-{[(3S)-3-Fluoropyrrolidin-1-yl]carbonyl}-2-{[6-(trifluoromethyl)pyridin-3-yl]methyl}-5,6,7,8-tetrahydro[1,2,4]triazolo[4,3-a]pyrazin-3(2H)-one (Diastereomer Mixture; 2 Isomers)

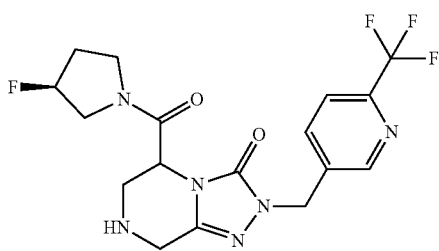 [SMILES: O=C(C1CNCc2nn(Cc3ccc(C(F)(F)F)nc3)c(=O)n21)N1CC[C@H](F)C1]

5-{[(3S)-3-Fluoropyrrolidin-1-yl]carbonyl}-2-{[6-(trifluoromethyl)pyridin-3-yl]methyl}[1,2,4]triazolo [4,3-a]pyrazin-3(2H)-one (86.0 mg, 210 µmol) was dissolved in ethanol (5 ml) and methanol (1 ml) and converted using a hydrogenation apparatus (H-Cube®, Pd/C 10% palladium, 1 bar, 95° C., flow rate: 1 ml/min). 58 mg (67% of theory) of the title compound were obtained.

LC-MS (Method 2): $R_t$=0.94 min; MS (ESIpos): m/z=415 [M+H]$^+$ $^1$H-NMR (500 MHz, DMSO-d6) δ [ppm]: 1.813 (1.19), 3.283 (0.46), 3.311 (1.04), 3.401 (2.43), 3.406 (1.50), 3.412 (3.22), 3.420 (5.01), 3.430 (5.50), 3.447 (5.07), 3.462 (6.71), 3.465 (2.94), 3.480 (4.70), 3.485 (2.04), 3.491 (1.30), 3.496 (1.84), 3.504 (1.75), 3.510 (1.83), 3.518 (1.89), 3.526 (1.32), 3.533 (0.84), 3.542 (0.45), 3.686 (1.67), 3.694 (1.47), 3.709 (3.60), 3.718 (3.20), 3.744 (3.82), 3.751 (3.63), 3.767 (1.83), 3.775 (1.55), 3.804 (1.31), 3.815 (1.42), 3.860 (0.41), 3.911 (0.64), 3.943 (14.14), 3.945 (13.65), 3.958 (0.58), 3.966 (0.59), 3.979 (1.56), 3.986 (0.43), 4.051 (0.46), 4.054 (0.44), 4.080 (0.47), 4.083 (0.45), 4.414 (0.47), 4.422 (1.05), 4.429 (0.63), 4.437 (1.97), 4.456 (3.43), 4.460 (1.97), 4.463 (1.97), 4.469 (2.08), 4.474 (1.74), 4.485 (2.52), 4.500 (15.08), 4.525 (0.43), 4.694 (0.47), 4.725 (0.51), 4.798 (0.45), 4.809 (0.69), 5.551 (0.84), 5.751 (6.23), 7.252 (0.77), 7.260 (1.11), 7.263 (1.24), 7.273 (2.04), 7.278 (2.66), 7.283 (2.57), 7.284 (2.74), 7.290 (4.96), 7.294 (3.81), 7.298 (3.76), 7.304 (5.95), 7.308 (5.23), 7.312 (3.53), 7.316 (4.24), 7.328 (5.60), 7.334 (3.69), 7.336 (3.61), 7.341 (14.08), 7.344 (16.00), 7.349 (2.55), 7.356 (5.58), 7.357 (6.30), 7.361 (2.79), 7.369 (1.04), 7.372 (1.70), 7.374 (1.14), 8.065 (2.18).

Example 43 tert-Butyl (5RS)-2-[(5-chloropyridin-3-yl)methyl]-5-{[(3S)-3-fluoropyrrolidin-1-yl]carbonyl}-3-oxo-2,5,6,8-tetrahydro[1,2,4]triazolo[4,3-a]pyrazine-7(3H)-carboxylate (Diastereomer Mixture; 2 Isomers)

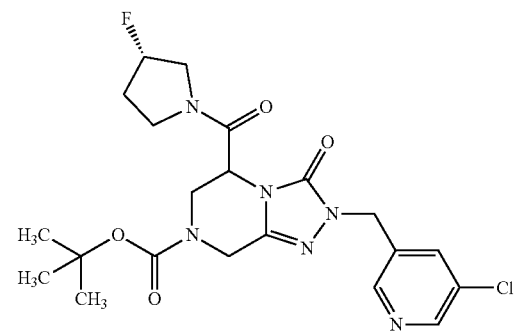 [SMILES: CC(C)(C)OC(=O)N1Cc2nn(Cc3cncc(Cl)c3)c(=O)n2C(C(=O)N2CC[C@H](F)C2)C1]

tert-Butyl (5S)-5-{[(3S)-3-fluoropyrrolidin-1-yl]carbonyl}-3-oxo-2,5,6,8-tetrahydro[1,2,4]triazolo[4,3-a]pyrazine-7(3H)-carboxylate (diastereomer mixture; 2 isomers) (589 mg, 1.66 mmol) was initially charged in acetonitrile (15 ml). Cesium carbonate (1.35 g, 4.14 mmol) and 3-chloro-5-(chloromethyl)pyridine (282 mg, 1.74 mmol) were subsequently added. After stirring for 72 hours, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulfate and filtered, and the filtrate was concentrated. 782 mg (94% purity, 92% of theory) of the title compound were obtained.

LC-MS (Method 2): R$_t$=1.42 min; MS (ESIpos): m/z=481 [M+H]$^+$

Example 44

(5RS)-2-[(5-Chloropyridin-3-yl)methyl]-5-{[(3S)-3-fluoropyrrolidin-1-yl]carbonyl}-5,6,7,8-tetrahydro[1,2,4]triazolo[4,3-a]pyrazin-3(2H)-one (Diastereomer Mixture; 2 Isomers)

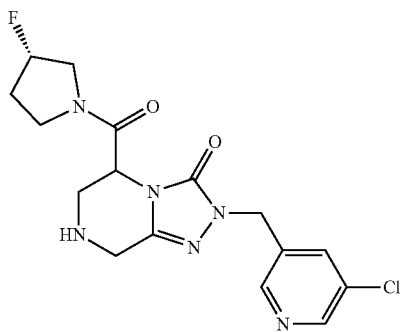 [SMILES: O=C(C1CNCc2nn(Cc3cncc(Cl)c3)c(=O)n21)N1CC[C@H](F)C1]

To a solution of tert-butyl (5RS)-2-[(5-chloropyridin-3-yl)methyl]-5-{[(3S)-3-fluoropyrrolidin-1-yl]carbonyl}-3-oxo-2,5,6,8-tetrahydro[1,2,4]triazolo[4,3-a]pyrazine-7(3H)-carboxylate (diastereomer mixture; 2 isomers) (782 mg, 94% purity, 1.53 mmol) in dichloromethane (15 ml) at room temperature was added trifluoroacetic acid (2.4 ml, 31 mmol). After the reaction mixture had been stirred at room temperature overnight, the solvent was removed under reduced pressure. 582 mg (97% of theory) of the title compound were obtained.

LC-MS (Method 2): R$_t$=0.73 min; MS (ESIpos): m/z=381 [M+H]$^+$

Example 45 tert-Butyl (5RS)-5-{[(3S)-3-fluoropyrrolidin-1-yl]carbonyl}-2-{[3-fluoro-2-(trifluoromethyl)pyridin-4-yl]methyl}-3-oxo-2,5,6,8-tetrahydro[1,2,4]triazolo[4,3-a]pyrazine-7(3H)-carboxylate (Diastereomer Mixture; 2 Isomers)

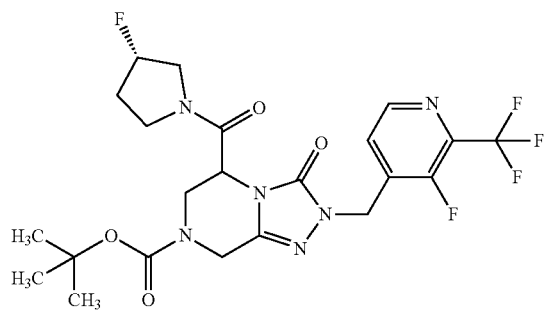 [SMILES: CC(C)(C)OC(=O)N1Cc2nn(Cc3ccnc(C(F)(F)F)c3F)c(=O)n2C(C(=O)N2CC[C@H](F)C2)C1]

tert-Butyl (5RS)-5-{[(3S)-3-fluoropyrrolidin-1-yl]carbonyl}-3-oxo-2,5,6,8-tetrahydro[1,2,4]triazolo[4,3-a]pyrazine-7(3H)-carboxylate (diastereomer mixture; 2 isomers) (212 mg, 40% purity, 239 µmol) was initially charged in acetonitrile (2.0 ml). Cesium carbonate (156 mg, 477 µmol) and 4-(chloromethyl)-3-fluoro-2-(trifluoromethyl)pyridine (56.1 mg, 262 µmol) were subsequently added. After stirring for 72 hours, the reaction mixture was admixed at room temperature with water and ethyl acetate. The organic phase was removed and the aqueous phase was extracted three times with ethyl acetate. The combined organic phases were washed with saturated aqueous sodium chloride solution, dried over sodium sulfate and filtered, and the filtrate was concentrated. The residue was purified via preparative HPLC (Chromatorex C18, 10 µm, 125 mm×30 mm; eluent: acetonitrile/water gradient). The product-containing fractions were concentrated under reduced pressure, and 36.0 mg (28% of theory) of the title compound were obtained.

LC-MS (Method 2): R$_t$=1.69 min; MS (ESIpos): m/z=477 [M-tBuCO$_2$]+

B. ASSESSMENT OF PHARMACOLOGICAL EFFICACY

The pharmacological activity of the compounds of the invention can be demonstrated by in vitro and in vivo studies as known to the person skilled in the art. The application examples which follow describe the biological action of the compounds of the invention, without restricting the invention to these examples.

Abbreviations and Acronyms

ATP adenosine triphosphate
COPD chronic obstructive pulmonary disease
LPS lipopolysaccharide
PGP proline-glycine-proline
Poly(I:C) polyinosinic-polycytidylic acid
B-1 Biochemical Human Prolyl Endopeptidase (PREP) Assay for Identification of Inhibitors of PREP Activity Using a Fluorescently Labeled Substrate
Principle of the Assay:

The enzymatic conversion of the fluorescent peptide substrate was observed on the basis of the measurement of the fluorescence intensity. The enzyme activity was determined by the ascertaining of the initial slope in the increase in fluorescence. Compounds that inhibit PREP were identified on the basis of the decrease in the initial slope compared to a reaction mixture without test compound.

Determination of Activity:

IC$_{50}$ values were determined by the plotting of the percentage PREP activity against the concentration of the test substance by interpolation.

Assay Description:

To recombinant full-length human prolyl endopeptidase (PREP, R&D-Systems, 4308-SE; final concentration, for example, 0.4 nM, volume: 25 al) in reaction buffer (50 mM Tris-HI, pH 7.5; 150 mM NaCl; 0.13% BSA, 5 mM EDTA, 3 mM GSH, 0.005% Brij-35) was added a test compound (in DMSO, in an appropriate final concentration range from 1 nM to 30 µM, volume: 1 µl) in a well of a 384-well microtiter plate. The reaction was started by adding the substrate Z-GlyPro-AMC (final concentration 50 µl; Z=carboxybenzyl; AMC=7-amino-4-methylcoumarin, volume: 25 µl). The progress of the PREP reaction was observed by measuring the fluorescence intensity in a Tecan SAFIRE II plate spectrophotometer at 3200 over a period of 60 min (excitation wavelength: 360 nm, emission wavelength: 465 nm).

Table B-1 below collates the $C_{50}$ values thus obtained from the human prolyl endopeptidase assay for individual working examples of the invention (some as mean values from multiple independent individual determinations).

TABLE B-1

| Example No. | Prolyl endopeptidase (human) $IC_{50}$ [mol/l] |
|---|---|
| 1 | 9.7E−10 |
| 2 | 3.05E−09 |
| 3 | 5.45E−09 |
| 4 | 5.15E−09 |
| 5 | 5.10E−10 |
| 6 | 6.70E−10 |
| 7 | 3.50E−09 |
| 8 | 4.55E−07 |
| 9 | 1.27E−09 |
| 10 | 3.00E−09 |
| 11 | 1.40E−09 |
| 12 | 7.60E−07 |
| 13 | 9.35E−10 |
| 14 | 8.70E−10 |
| 15 | 7.25E−08 |
| 16 | 1.70E−10 |
| 17 | 1.60E−10 |
| 18 | 3.70E−10 |
| 19 | 1.46E−07 |
| 20 | 2.20E−10 |
| 21 | 3.25E−10 |
| 22 | 1.20E−07 |
| 23 | 3.50E−10 |
| 24 | 6.60E−10 |
| 25 | 7.30E−10 |
| 26 | 8.70E−10 |
| 27 | 1.70E−09 |
| 28 | 2.20E−09 |
| 29 | 2.40E−09 |
| 30 | 2.80E−09 |
| 31 | 4.00E−09 |
| 32 | 5.10E−09 |
| 33 | 2.80E−07 |
| 34 | 4.15E−07 |
| 35 | 4.20E−09 |
| 37 | 4.70E−08 |
| 38 | 1.20E−09 |
| 39 | 8.85E−08 |
| 40 | 2.00E−10 |
| 41 | 8.75E−07 |

B-2 Biochemical Murine Prolyl Endopeptidase (PREP) Assay

Determination of Activity:

$IC_{50}$ values were determined by the plotting of the percentage PREP activity against the concentration of the test substance by interpolation.

Mouse Brain Homogenate Preparation:

Mouse brain from BalbC mice in 0.8 ml of a mixture of 100 mM sodium phosphate (pH 7.0) and 3 mM dithiothreitol was homogenized 4×25 sec in an OmniBead Ruptor. The resultant homogenate was centrifuged at 13 000 rpm and 400 for 20 min. The aliquoted supernatant was frozen at −80° C.

Assay Description:

Mouse brain homogenate was diluted 1:100 in a reaction buffer (50 mM Tris-HCl, pH 7.5; 150 mM NaCl; 0.13% BSA, 5 mM EDTA, 3 mM GSH, 0.005% Brij-35) and 25 µl of the solution were introduced into a well of a 384-well microtiter plate. A test compound (in DMSO, in an appropriate final concentration range of, for example, 1 nM to 30 µM, volume: 1 µl) was added. The reaction is started by adding the substrate Z-Gly-Pro-AMC (final concentration 50 µM; Z=carboxybenzyl; AMC=7-amino-4-methylcoumarin, volume: 25 µl). The progress of the PREP reaction was observed by measuring the fluorescence intensity in a suitable plate spectrometer at 32° C. over a period of, for example, 60 min (excitation wavelength: 360 nm, emission wavelength: 465 nm).

Table 1 below collates the $IC_{50}$ values thus obtained from the KDR and PDGFRβ kinase assays for individual working examples of the invention (some as mean values from multiple independent individual determinations).

B-3 Efficacy of PREP Inhibitors in Mice Exposed to Cigarette Smoke

The suitability of the substances of the invention for treatment/prophylaxis of the disorders mentioned can be shown in the animal model which follows.

Material and Methods:

Mice: Strain: BALB/C, origin: Charles River Netherlands, sex: male, age: 8 to 10 weeks, weight: 25 g, n=21.

Vehicle: Solutol, EtOH, water (S: 40%, EtOH 10%, water 50% (v/v))

For the administration of PREP inhibitors by gavage, they were dissolved in the above-described vehicle (c=3750 µg/ml).

The mice were divided into three groups of seven animals each and treated as follows:

Group 1: no smoke exposure (ambient air), two daily doses of 200 µl of vehicle without active ingredient Group 2: smoke exposure, two daily doses of 200 µl of vehicle without active ingredient Group 3: smoke exposure, two daily doses of 200 µl of vehicle with active ingredient (30 mg/kg in each case)

Smoke Exposure:

For exposure to cigarette smoke, the animals of groups 2 and 3 (the animals of group 1 did not experience any smoke exposure and remained in the holding cages) were introduced twice daily into an exposure chamber having a total volume of 52 liters that was divided into 16 individual cages by dividing grids. For exposure to smoke, the animals, which were kept in groups (7 animals per cage), were each introduced into a single cage of the exposure chamber (7 animals per cage). Between the two daily exposures, there was a smoke-free period of 5 hours. In total, the animals were exposed to smoke on five successive days. Cigarettes were each burnt in pairs. The mainstream smoke from the cigarettes was introduced into the exposure chamber.

The smoke exposure was conducted according to the following scheme:

Day 1: 1st smoking period: 2×2 cigarettes, 2nd smoking period: 3×2 cigarettes

Day 2: 1st smoking period: 4×2 cigarettes, 2nd smoking period: 5×2 cigarettes

Day 3: 1st smoking period: 6×2 cigarettes, 2nd smoking period: 7×2 cigarettes

Days 4 and 5: 1st and 2nd smoking period: each 7×2 cigarettes

The treatment of the animals with PREP inhibitors or vehicle was commenced 15 minutes before the first smoking period on day 1. Subsequently, the animals received two daily doses at an interval of 8 hours of PREP inhibitors or vehicle in the above-described dosage.

On day 6, the animals were sacrificed by the intraperitoneal administration of 150 mg/kg pentobarbital (Euthesate®). The tracheas were exposed and incised for insertion of cannulas. These cannulas were used to purge the lungs four times with physiological saline at 37° C. The cells from these four fractions in each case of the bronchoalveolar lavage fluid (BALF) were centrifuged at 4° C. at 400×g/5 minutes. Subsequently, the cell pellets were combined and resuspended in 150 µl of physiological saline (4° C.) in each case. Following staining with Türk's solution, the total number of cells was counted by light microscopy. For quantification of the neutrophil granulocytes (neutrophils for short), the cells were transferred to microscope slides (Cytospin) and stained with DiffQuick (Dade A. G., Dudingen, Switzerland). Finally, neutrophils, macrophages and lymphocytes were counted and the relative proportions of the total number previously determined was calculated. To determine the PGP concentration in the BALF, 200 µl in each case from the supernatant from the first BALF fraction were admixed with bestatin (final concentration: 1 mM) and stored at −20° C. until analysis.

Quantification of PGP in the Bronchoalveolar Lavage Fluid (BALF)

PGP was determined by the method of Hardison et al. [Hardison et al., *J. Immunol.* 2009, 182:4423-4431] using the following equipment: ESI-LC-MS/MS (Shimadzu HPLC, Columbia, Mass., USA) with a Finnigan TSQ quantum discovery Max quadrupole mass spectrometer in conjunction with electrospray thermal ionization (Thermo Fisher Scientific, San Jose, Calif., USA) and an Atlantis dC18 column (100 mm×2.1 mm, dp=3 µm, Waters Chromatography, Milford, Mass., USA) or an Atlantis pre-column (10 mm×2.1 mm, dp=3 µm, Waters).

C. WORKING EXAMPLES FOR PHARMACEUTICAL COMPOSITIONS

The compounds of the invention can be converted to pharmaceutical preparations as follows:

Tablet:
Composition:
100 mg of the compound of the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.

Production:
The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.

Suspension for Oral Administration:
Composition:
1000 mg of the compound of the invention, 1000 mg of ethanol (96%), 400 mg of Rhodigel® (xanthan gum from FMC, Pennsylvania, USA) and 99 g of water.

10 ml of oral suspension corresponds to a single dose of 100 mg of the compound of the invention.

Production:
The Rhodigel is suspended in ethanol; the compound of the invention is added to the suspension. The water is added while stirring. The mixture is stirred for about 6 h until the swelling of the Rhodigel is complete.

Solution for Oral Administration:
Composition:
500 mg of the compound of the invention, 2.5 g of polysorbate and 97 g of polyethylene glycol 400. 20 g of oral solution correspond to a single dose of 100 mg of the compound of the invention.

Production:
The compound of the invention is suspended in the mixture of polyethylene glycol and polysorbate with stirring. The stirring process is continued until the compound according to the invention has completely dissolved.

I.V. Solution:
The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of formula (I):

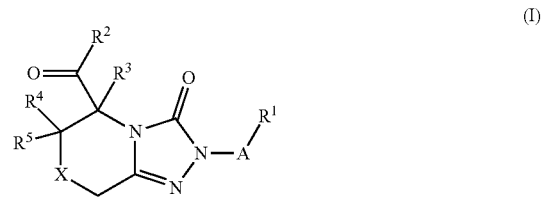

(I)

or a pharmaceutically acceptable salt thereof,
wherein:
(i) A is —CD$_2$- or —(C$_1$-C$_4$) alkylene-, wherein the (C$_1$-C$_4$) alkylene is optionally substituted by 1 or more substituents independently selected from the group consisting of F, OH, and O(C$_1$-C$_4$) alkyl; or
(ii) A is:

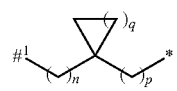

wherein:
n is 0 or 1;
p is 0 or 1;
q is 1 or 2;
$^1$ is the point of attachment to the nitrogen atom of the 5-oxo-4,5-dihydro-1H-1,2,4-triazol-1-yl ring; and
* is the point of attachment to R$^1$;
X is —N(R$^{10}$)—, —N[C(O)R$^8$]—, —N[C(O)NR$^6$R$^7$]—, or —N[C(O)OR$^9$]—;
R$^1$ is (C$_3$-C$_7$) cycloalkyl, phenyl, or 5- to 10-membered heteroaryl;
wherein the (C$_3$-C$_7$) cycloalkyl is optionally substituted by 1, 2, or 3 substituents independently selected from the group consisting of halogen, CN, (C$_1$-C$_4$) alkyl, CF$_3$, and O(C$_1$-C$_4$) alkyl;
wherein the phenyl is substituted by 1, 2, 3, or 4 substituents independently selected from the group consisting of halogen, CN, (C$_1$-C$_4$) alkyl, CF$_3$, C(O)NH$_2$, C(O)NH(C$_1$-C$_4$) alkyl, C(O)N[(C$_1$-C$_4$) alkyl]$_2$, C(O)NH(C$_3$-C$_5$) cycloalkyl, C(O)OH, C(O)O(C$_1$-C$_4$) alkyl, NH$_2$, NH(C$_1$-C$_4$) alkyl, N[(C$_1$-C$_4$) alkyl]$_2$, O(C$_1$-C$_4$) alkyl, OCH$_2$F, OCHF$_2$, OCF$_3$, S(C$_1$-C$_4$) alkyl, S(O)(C$_1$-C$_4$) alkyl, S(O)$_2$(C$_1$-C$_4$) alkyl, S(O)$_2$NH$_2$, S(O)$_2$NH(C$_1$-C$_4$) alkyl, S(O)$_2$N[(C$_1$-C$_4$) alkyl]$_2$, S(O)$_2$(C$_3$-C$_4$) cycloalkyl, (C$_3$-C$_6$) cycloalkyl, and (C$_3$-C$_5$) cycloalkoxy;
wherein the 5- to 10-membered heteroaryl is substituted by 1, 2, 3, or 4 substituents independently selected from the group consisting of halogen, CN, (C$_1$-C$_4$) alkyl, CF$_3$, C(O)NH$_2$, C(O)NH(C$_1$-C$_4$)

alkyl, C(O)N[(C$_1$-C$_4$) alkyl]$_2$, C(O)NH(C$_3$-C$_5$) cycloalkyl, C(O)OH, C(O)O(C$_1$-C$_4$) alkyl, NH$_2$, NH(C$_1$-C$_4$) alkyl, N[(C$_1$-C$_4$) alkyl]$_2$, O(C$_1$-C$_4$) alkyl, OCHF$_2$, OCF$_3$, OCH$_2$CF$_3$, S(C$_1$-C$_4$) alkyl, S(O)(C$_1$-C$_4$) alkyl, S(O)$_2$(C$_1$-C$_4$) alkyl, S(O)$_2$NH$_2$, S(O)$_2$NH(C$_1$-C$_4$) alkyl, S(O)$_2$N[(C$_1$-C$_4$) alkyl]$_2$, S(O)$_2$(C$_3$-C$_4$) cycloalkyl, (C$_3$-C$_6$) cycloalkyl, (C$_3$-C$_5$) cycloalkoxy, and phenyl; and wherein each phenyl substituent of the 5- to 10-membered heteroaryl is optionally and independently substituted by 1, 2, 3, 4, or 5 substituents independently selected from the group consisting of F, Cl, CH$_3$, CH$_2$CH$_3$, and OCH$_3$;

(iii) R$^2$ is:

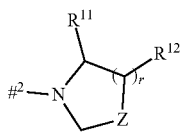

wherein:

r is 0 or 1;

Z is —CR$^{13A}$R$^{13B}$—, —NR$^{14}$—, —O—, —S—, —S(O)—, or —S(O)$_2$—;

R$^{11}$ is H, CN, (C$_1$-C$_4$) alkyl, C(O)H, or C(O)CH$_3$;
wherein the (C$_1$-C$_4$) alkyl is optionally substituted by 1, 2, 3, 4, or 5 substituents independently selected from the group consisting of F and OH; and
wherein the C(O)CH$_3$ is optionally substituted by 1, 2, or 3 substituents independently selected from the group consisting of F and OH;

R$^{12}$ is H, F, or (C$_1$-C$_4$) alkyl;

R$^{13A}$ is H, halogen, CN, (C$_1$-C$_4$) alkyl, CH$_2$F, CHF$_2$, CF$_3$, OH, O(C$_1$-C$_4$) alkyl, OCHF$_2$, OCF$_3$, OCH$_2$CF$_3$, (C$_3$-C$_6$) cycloalkyl, or (C$_3$-C$_5$) cycloalkoxy:
wherein the (C$_1$-C$_4$) alkyl is optionally substituted by 1, 2, 3, 4, or 5 substituents independently selected from the group consisting of NH$_2$, NH(C$_1$-C$_4$) alkyl, N[(C$_1$-C$_4$) alkyl]$_2$, and OH;

R$^{13B}$ is H, F, or (C$_1$-C$_4$) alkyl,
wherein the (C$_1$-C$_4$) alkyl is optionally substituted by 1, 2, 3, 4, or 5 F substituents; or R$^{11}$ and R$^{12}$, together with the carbon atoms to which they are attached, form cyclopropyl or cyclobutyl;
wherein the cyclopropyl or cyclobutyl is optionally substituted by 1 or 2 F substituents; or R$^{12}$ and R$^{13A}$, together with the carbon atoms to which they are attached, form cyclopropyl or cyclobutyl;
wherein the cyclopropyl or cyclobutyl is optionally substituted by 1 or 2 F substituents; or R$^{13A}$ and R$^{13B}$, together with the carbon atoms to which they are attached, form cyclopropyl or cyclobutyl;
wherein the cyclopropyl or cyclobutyl is optionally substituted by 1 or 2 F substituents;

R$^{14}$ is H or CH$_3$; and

$^2$ is the point of attachment to —C(O)—; or (iv) R$^2$ is:

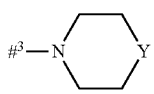

wherein:

Y is —CR$^{16A}$R$^{16B}$—, —NR$^{15}$—, —O—, or —S—;

R$^{15}$ is H or CH$_3$;

R$^{16A}$ is H or CH$_3$;

R$^{16B}$ is H or CH$_3$; and

$^3$ is the point of attachment to —C(O)—;

R$^3$ is H;

R$^4$ is H or (C$_1$-C$_4$) alkyl;
wherein the (C$_1$-C$_4$) alkyl is optionally substituted by 1, 2, 3, 4, or 5 substituents independently selected from the group consisting of F, NH(C$_1$-C$_4$) alkyl, N[(C$_1$-C$_4$) alkyl]$_2$, OH, and O(C$_1$-C$_4$) alkyl;

R$^5$ is H;

R$^6$ is (C$_1$-C$_6$) alkyl, (C$_3$-C$_6$) cycloalkyl, phenyl, or 5- or 6-membered heteroaryl;
wherein the (C$_1$-C$_6$) alkyl is optionally substituted by 1, 2, 3, 4, or 5 substituents independently selected from the group consisting of F, CN, OH, and O(C$_1$-C$_4$) alkyl; and
wherein the (C$_3$-C$_6$) cycloalkyl, phenyl, or 5- or 6-membered heteroaryl is optionally substituted by 1, 2, or 3 substituents independently selected from the group consisting of halogen, CN, CF$_3$, (C$_1$-C$_4$) alkyl, and O(C$_1$-C$_4$) alkyl;

R$^7$ is H or (C$_1$-C$_4$) alkyl;
wherein the (C$_1$-C$_4$) alkyl is optionally substituted by 1, 2, 3, 4, or 5 F substituents;

R$^8$ is (C$_1$-C$_4$) alkyl, (C$_3$-C$_6$) cycloalkyl, phenyl, or 5- or 6-membered heteroaryl;
wherein the (C$_1$-C$_4$) alkyl is optionally substituted by 1, 2, 3, 4, or 5 substituents independently selected from the group consisting of F, CN, OH, and O(C$_1$-C$_4$) alkyl; and
wherein the (C$_3$-C$_6$) cycloalkyl, phenyl, or 5- or 6-membered heteroaryl is optionally substituted by 1, 2, or 3 substituents independently selected from the group consisting of halogen, CN, CF$_3$, (C$_1$-C$_4$) alkyl, and O(C$_1$-C$_4$) alkyl;

R$^9$ is (C$_1$-C$_4$) alkyl, (C$_3$-C$_6$) cycloalkyl, or phenyl;
wherein the (C$_1$-C$_4$) alkyl is optionally substituted by 1, 2, 3, 4, or 5 F substituents; and
wherein the (C$_3$-C$_6$) cycloalkyl or phenyl is optionally substituted by 1, 2, or 3 substituents independently selected from the group consisting of halogen, CN, CF$_3$, (C$_1$-C$_4$) alkyl, and O(C$_1$-C$_4$) alkyl; and R$^{10}$ is H, (C$_1$-C$_4$) alkyl, (C$_3$-C$_6$) cycloalkyl, or phenyl;
wherein the (C$_1$-C$_4$) alkyl is optionally substituted by 1, 2, 3, 4, or 5 substituents independently selected from the group consisting of F, CN, OH, O(C$_1$-C$_4$) alkyl, and (C$_3$-C$_6$) cycloalkyl; and
wherein the (C$_3$-C$_6$) cycloalkyl or phenyl is optionally substituted by 1, 2, or 3 substituents independently selected from the group consisting of halogen, CN, CF$_3$, (C$_1$-C$_4$) alkyl, and O(C$_1$-C$_4$) alkyl;

with the provisos that:
(1) if R$^{11}$ is H, then at least one of R$^{12}$, R$^{13A}$, or R$^{13B}$ is not H; and
(2) if R$^{11}$ is CN, (C$_1$-C$_4$) alkyl, C(O)H, or C(O)CH$_3$, then R$^{12}$, R$^{13A}$, and R$^{13B}$ are H.

2. The compound according to claim 1, or a pharmaceutically acceptable salt thereof, wherein:

A is —(C$_1$-C$_4$) alkylene-;

X is —N(R$^{10}$)—, —N[C(O)R$^8$]—, —N[C(O)NR$^6$R$^7$]—, or —N[C(O)OR$^9$]—;

R$^1$ is phenyl or 6-membered heteroaryl;

wherein the phenyl or 6-membered heteroaryl is substituted by 1, 2, or 3 substituents independently selected from the group consisting of F, Cl, Br, CN, CH$_3$, CF$_3$, CH$_2$CH$_3$, C(O)NHCH$_3$, C(O)N(CH$_3$)$_2$, C(O)OH, C(O)OCH$_3$, C(O)OCH$_2$CH$_3$, C(O)OC(CH$_3$)$_3$, OCH$_3$, OCH$_2$F, OCHF$_2$, OCF$_3$, OCH$_2$CH$_3$, and cyclopropyl;

R$^2$ is:

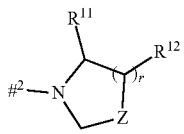

wherein:
r is 1;
Z is —CR$^{13A}$R$^{13B}$—;
R$^{11}$ is H;
R$^{12}$ is H or F;
R$^{13A}$ is H, F, CH$_3$, CH$_2$F, CHF$_2$, CF$_3$, OH, OCH$_3$, OCHF$_2$, or OCF$_3$;
R$^{13B}$ is H or F; and
$^2$ is the point of attachment to —C(O)—;
R$^3$ is H;
R$^4$ is H or CH$_3$;
  wherein the CH$_3$ is optionally substituted by 1, 2, or 3 F substituents;
R$^5$ is H;
R$^6$ is (C$_1$-C$_6$) alkyl, (C$_3$-C$_5$) cycloalkyl, phenyl, or 6-membered heteroaryl;
  wherein the (C$_1$-C$_6$) alkyl or (C$_3$-C$_5$) cycloalkyl is optionally substituted by 1, 2, or 3 F substituents;
  wherein the phenyl is optionally substituted by 1 or 2 substituents independently selected from the group consisting of F, Cl, Br, CN, CH$_3$, CF$_3$, CH$_2$CH$_3$, OCH$_3$, and OCH$_2$CH$_3$; and
  wherein the 6-membered heteroaryl is optionally substituted by 1 or 2 substituents independently selected from the group consisting of F, Cl, CN, CH$_3$, CF$_3$, CH$_2$CH$_3$, OCH$_3$, and OCH$_2$CH$_3$;
R$^7$ is H or CH$_3$;
  wherein the CH$_3$ is optionally substituted by 1, 2, or 3 F substituents;
R$^8$ is (C$_1$-C$_4$) alkyl, (C$_3$-C$_6$) cycloalkyl, phenyl, or 6-membered heteroaryl;
  wherein the (C$_1$-C$_4$) alkyl or (C$_3$-C$_6$) cycloalkyl is optionally substituted by 1, 2, or 3 F substituents;
R$^9$ is (C$_1$-C$_4$) alkyl or phenyl;
  wherein the (C$_1$-C$_4$) alkyl is optionally substituted by 1, 2, or 3 F substituents; and
R$^{10}$ is H, (C$_1$-C$_4$) alkyl, (C$_3$-C$_6$) cycloalkyl, or phenyl;
  wherein the (C$_1$-C$_4$) alkyl is optionally substituted by 1, 2, 3, 4, or 5 substituents independently selected from the group consisting of F, cyclopropyl, and cyclobutyl;
  wherein the (C$_3$-C$_6$) cycloalkyl is optionally substituted by 1, 2, or 3 F substituents; and
  wherein the phenyl is optionally substituted by 1, 2, or 3 substituents independently selected from the group consisting of F, Cl, Br, CN, CH$_3$, CF$_3$, CH$_2$CH$_3$, OCH$_3$, and OCH$_2$CH$_3$.

3. The compound according to claim 1, or a pharmaceutically acceptable salt thereof, wherein:
A is —CH$_2$—;
X is —N(R$^{10}$)—, —N[C(O)R$^8$]—, —N[C(O)NR$^6$R$^7$]—, or —N[C(O)OR$^9$]—;
R$^1$ is phenyl or pyridyl;

wherein the phenyl is substituted by 1 or 2 substituents independently selected from the group consisting of F, CH$_3$, and CF$_3$, and
wherein the pyridyl is substituted by 1 or 2 substituents independently selected from the group consisting of F, Cl, and CF$_3$;

R$^2$ is:

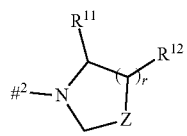

wherein:
r is 1;
Z is —CR$^{13A}$R$^{13B}$—;
R$^{11}$ is H;
R$^{12}$ is H or F;
R$^{13A}$ is H or F;
R$^{13B}$ is H; and
$^2$ is the point of attachment to —C(O)—;
R$^3$ is H;
R$^4$ is H or CH$_3$;
R$^5$ is H;
R$^6$ is (C$_1$-C$_4$) alkyl, cyclopropyl, or phenyl;
  wherein the (C$_1$-C$_6$) alkyl is optionally substituted by 1, 2, or 3 F substituents; and
  wherein the phenyl is substituted by 1 or 2 substituents independently selected from the group consisting of Cl and CF$_3$;
R$^7$ is H;
R$^8$ is CH$_3$, CH$_2$CH$_3$, CH$_2$CH$_2$CH$_3$, CH$_2$CH$_2$CF$_3$, or cyclopropyl;
R$^9$ is C(CH$_3$)$_3$; and
R$^{10}$ is H, CH$_3$, CH$_2$CH$_3$, CH$_2$CF$_3$, cyclopropyl, or cyclobutyl;
  wherein the CH$_3$ is optionally substituted by 1, 2, or 3 cyclopropyl substituents.

4. A pharmaceutical composition comprising one or more pharmaceutically acceptable excipients and a compound according to claim 1, or a pharmaceutically acceptable salt thereof.

5. The pharmaceutical composition according to claim 4, wherein the pharmaceutical composition further comprises at least one additional active ingredient selected from the group consisting of an endothelin antagonist, pirfenidone, a phosphodiesterase 5 inhibitor, a prostacyclin (IP) receptor agonist, a prostacyclin analog, a serine/threonine kinase inhibitor, a soluble guanylate cyclase activator, a soluble guanylate cyclase stimulator, and a tyrosine kinase inhibitor.

6. A method for inhibiting prolyl endopeptidase activity in an animal, wherein the method comprises administering to the animal in need thereof an effective amount of a compound according to claim 1, or a pharmaceutically acceptable salt thereof.

7. The method according to claim 6, wherein the animal has a disease or disorder selected from the group consisting of acute exacerbation in chronic obstructive pulmonary disease, arteriosclerosis, asthma, bronchiectasis, bronchiolitis obliterans syndrome, chronic bronchitis, cystic fibrosis, idiopathic pulmonary fibrosis, an inflammation disorder of the eye, an inflammation disorder of the internal organs, an inflammation disorder of the skin, myocarditis, pulmonary emphysema, pulmonary hypertension in chronic obstructive pulmonary disease, and a pulmonary inflammation disorder.

8. The method according to claim 7, wherein the cystic fibrosis is mucoviscidosis.

9. The method according to claim 7, wherein the pulmonary inflammation disorder is chronic obstructive lung disease.

10. The method according to claim 6, wherein the animal is a human.

11. The method according to claim 7, wherein the animal is a human.

12. A method for inhibiting prolyl endopeptidase activity in an animal, wherein the method comprises administering to the animal in need thereof an effective amount of the pharmaceutical composition according to claim 4.

13. The method according to claim 12, wherein the animal has a disease or disorder selected from the group consisting of acute exacerbation in chronic obstructive pulmonary disease, arteriosclerosis, asthma, bronchiectasis, bronchiolitis obliterans syndrome, chronic bronchitis, cystic fibrosis, idiopathic pulmonary fibrosis, an inflammation disorder of the eye, an inflammation disorder of the internal organs, an inflammation disorder of the skin, myocarditis, pulmonary emphysema, pulmonary hypertension in chronic obstructive pulmonary disease, and a pulmonary inflammation disorder.

14. The method according to claim 13, wherein the cystic fibrosis is mucoviscidosis.

15. The method according to claim 13, wherein the pulmonary inflammation disorder is chronic obstructive lung disease.

16. The method according to claim 12, wherein the animal is a human.

17. The method according to claim 13, wherein the animal is a human.

18. A method for inhibiting prolyl endopeptidase activity in an animal, wherein the method comprises administering to the animal in need thereof an effective amount of the pharmaceutical composition according to claim 5.

19. The method according to claim 18, wherein the animal has a disease or disorder selected from the group consisting of acute exacerbation in chronic obstructive pulmonary disease, arteriosclerosis, asthma, bronchiectasis, bronchiolitis obliterans syndrome, chronic bronchitis, cystic fibrosis, idiopathic pulmonary fibrosis, an inflammation disorder of the eye, an inflammation disorder of the internal organs, an inflammation disorder of the skin, myocarditis, pulmonary emphysema, pulmonary hypertension in chronic obstructive pulmonary disease, and a pulmonary inflammation disorder.

20. The method according to claim 17, wherein the cystic fibrosis is mucoviscidosis.

21. The method according to claim 17, wherein the pulmonary inflammation disorder is chronic obstructive lung disease.

22. The method according to claim 18, wherein the animal is a human.

23. The method according to claim 19 wherein the animal is a human.

24. A process for preparing a compound of formula (I) according to claim 1:

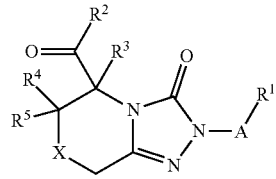

(I)

or a pharmaceutically acceptable salt thereof,
wherein:
(i) A is —$CD_2$- or —($C_1$-$C_4$) alkylene-, wherein the ($C_1$-$C_4$) alkylene is optionally substituted by 1 or more substituents independently selected from the group consisting of F, OH, and O($C_1$-$C_4$) alkyl; or
(ii) A is:

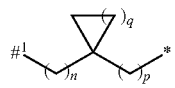

wherein:
n is 0 or 1;
p is 0 or 1;
q is 1 or 2;
$^1$ is the point of attachment to the nitrogen atom of the 5-oxo-4,5-dihydro-1H-1,2,4-triazol-1-yl ring; and
* is the point of attachment to $R^1$;
X is —N($R^{10}$)—, —N[C(O)$R^8$]—, —N[C(O)N$R^6R^7$]—, or —N[C(O)O$R^9$]—;
$R^1$ is ($C_3$-$C_7$) cycloalkyl, phenyl, or 5- to 10-membered heteroaryl;
wherein the ($C_3$-$C_7$) cycloalkyl is optionally substituted by 1, 2, or 3 substituents independently selected from the group consisting of halogen, CN, ($C_1$-$C_4$) alkyl, $CF_3$, and O($C_1$-$C_4$) alkyl;
wherein the phenyl is substituted by 1, 2, 3, or 4 substituents independently selected from the group consisting of halogen, CN, ($C_1$-$C_4$) alkyl, $CF_3$, C(O)$NH_2$, C(O)NH($C_1$-$C_4$) alkyl, C(O)N[($C_1$-$C_4$) alkyl]$_2$, C(O)NH($C_3$-$C_5$) cycloalkyl, C(O)OH, C(O)O($C_1$-$C_4$) alkyl, $NH_2$, NH($C_1$-$C_4$) alkyl, N[($C_1$-$C_4$) alkyl]$_2$, O($C_1$-$C_4$) alkyl, $OCH_2$F, $OCHF_2$, $OCF_3$, S($C_1$-$C_4$) alkyl, S(O)($C_1$-$C_4$) alkyl, S(O)$_2$($C_1$-$C_4$) alkyl, S(O)$_2$$NH_2$, S(O)$_2$NH($C_1$-$C_4$) alkyl, S(O)$_2$N[($C_1$-$C_4$) alkyl]$_2$, S(O)$_2$($C_3$-$C_4$) cycloalkyl, ($C_3$-$C_6$) cycloalkyl, and ($C_3$-$C_5$) cycloalkoxy;
wherein the 5- to 10-membered heteroaryl is substituted by 1, 2, 3, or 4 substituents independently selected from the group consisting of halogen, CN, ($C_1$-$C_4$) alkyl, $CF_3$, C(O)$NH_2$, C(O)NH($C_1$-$C_4$) alkyl, C(O)N[($C_1$-$C_4$) alkyl]$_2$, C(O)NH($C_3$-$C_5$) cycloalkyl, C(O)OH, C(O)O($C_1$-$C_4$) alkyl, $NH_2$, NH($C_1$-$C_4$) alkyl, N[($C_1$-$C_4$) alkyl]$_2$, O($C_1$-$C_4$) alkyl, $OCHF_2$, $OCF_3$, $OCH_2CF_3$, S($C_1$-$C_4$) alkyl, S(O)($C_1$-$C_4$) alkyl, S(O)$_2$($C_1$-$C_4$) alkyl, S(O)$_2$$NH_2$, S(O)$_2$NH($C_1$-$C_4$) alkyl, S(O)$_2$N[($C_1$-$C_4$) alkyl]$_2$, S(O)$_2$($C_3$-$C_4$) cycloalkyl, ($C_3$-$C_6$) cycloalkyl, ($C_3$-$C_5$) cycloalkoxy, and phenyl; and
wherein each phenyl substituent of the 5- to 10-membered heteroaryl is optionally and independently substituted by 1, 2, 3, 4, or 5 substituents independently selected from the group consisting of F, Cl, $CH_3$, $CH_2CH_3$, and $OCH_3$;

(iii) R² is:

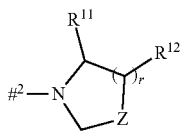

wherein:
r is 0 or 1;
Z is —CR$^{13A}$R$^{13B}$—, —NR$^{14}$—, —O—, —S—, —S(O)—, or —S(O)$_2$—;
R$^{11}$ is H, CN, (C$_1$-C$_4$) alkyl, C(O)H, or C(O)CH$_3$;
  wherein the (C$_1$-C$_4$) alkyl is optionally substituted by 1, 2, 3, 4, or 5 substituents independently selected from the group consisting of F and OH; and
  wherein the C(O)CH$_3$ is optionally substituted by 1, 2, or 3 substituents independently selected from the group consisting of F and OH;
R$^{12}$ is H, F, or (C$_1$-C$_4$) alkyl;
R$^{13A}$ is H, halogen, CN, (C$_1$-C$_4$) alkyl, CH$_2$F, CHF$_2$, CF$_3$, OH, O(C$_1$-C$_4$) alkyl, OCHF$_2$, OCF$_3$, OCH$_2$CF$_3$, (C$_3$-C$_6$) cycloalkyl, or (C$_3$-C$_5$) cycloalkoxy:
  wherein the (C$_1$-C$_4$) alkyl is optionally substituted by 1, 2, 3, 4, or 5 substituents independently selected from the group consisting of NH$_2$, NH(C$_1$-C$_4$) alkyl, N[(C$_1$-C$_4$) alkyl]$_2$, and OH;
R$^{13B}$ is H, F, or (C$_1$-C$_4$) alkyl,
  wherein the (C$_1$-C$_4$) alkyl is optionally substituted by 1, 2, 3, 4, or 5 F substituents; or
R$^{11}$ and R$^{12}$, together with the carbon atoms to which they are attached, form cyclopropyl or cyclobutyl;
  wherein the cyclopropyl or cyclobutyl is optionally substituted by 1 or 2 F substituents; or
R$^{12}$ and R$^{13A}$, together with the carbon atoms to which they are attached, form cyclopropyl or cyclobutyl;
  wherein the cyclopropyl or cyclobutyl is optionally substituted by 1 or 2 F substituents; or
R$^{13A}$ and R$^{13B}$, together with the carbon atoms to which they are attached, form cyclopropyl or cyclobutyl;
  wherein the cyclopropyl or cyclobutyl is optionally substituted by 1 or 2 F substituents;
R$^{14}$ is H or CH$_3$; and
² is the point of attachment to —C(O)—; or
(iv) R² is:

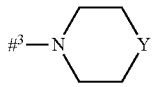

wherein:
Y is —CR$^{16A}$R$^{16B}$—, —NR$^{15}$—, —O—, or —S—;
R$^{15}$ is H or CH$_3$;
R$^{16A}$ is H or CH$_3$;
R$^{16B}$ is H or CH$_3$; and
³ is the point of attachment to —C(O)—;
R³ is H;
R⁴ is H or (C$_1$-C$_4$) alkyl;
  wherein the (C$_1$-C$_4$) alkyl is optionally substituted by 1, 2, 3, 4, or 5 substituents independently selected from the group consisting of F, NH(C$_1$-C$_4$) alkyl, N[(C$_1$-C$_4$) alkyl]$_2$, OH, and O(C$_1$-C$_4$) alkyl;
R⁵ is H;
R⁶ is (C$_1$-C$_6$) alkyl, (C$_3$-C$_6$) cycloalkyl, phenyl, or 5- or 6-membered heteroaryl;

wherein the (C$_1$-C$_6$) alkyl is optionally substituted by 1, 2, 3, 4, or 5 substituents independently selected from the group consisting of F, CN, OH, and O(C$_1$-C$_4$) alkyl; and
  wherein the (C$_3$-C$_6$) cycloalkyl, phenyl, or 5- or 6-membered heteroaryl is optionally substituted by 1, 2, or 3 substituents independently selected from the group consisting of halogen, CN, CF$_3$, (C$_1$-C$_4$) alkyl, and O(C$_1$-C$_4$) alkyl;
R⁷ is H or (C$_1$-C$_4$) alkyl;
  wherein the (C$_1$-C$_4$) alkyl is optionally substituted by 1, 2, 3, 4, or 5 F substituents;
R⁸ is (C$_1$-C$_4$) alkyl, (C$_3$-C$_6$) cycloalkyl, phenyl, or 5- or 6-membered heteroaryl;
  wherein the (C$_1$-C$_4$) alkyl is optionally substituted by 1, 2, 3, 4, or 5 substituents independently selected from the group consisting of F, CN, OH, and O(C$_1$-C$_4$) alkyl; and
  wherein the (C$_3$-C$_6$) cycloalkyl, phenyl, or 5- or 6-membered heteroaryl is optionally substituted by 1, 2, or 3 substituents independently selected from the group consisting of halogen, CN, CF$_3$, (C$_1$-C$_4$) alkyl, and O(C$_1$-C$_4$) alkyl;
R⁹ is (C$_1$-C$_4$) alkyl, (C$_3$-C$_6$) cycloalkyl, or phenyl;
  wherein the (C$_1$-C$_4$) alkyl is optionally substituted by 1, 2, 3, 4, or 5 F substituents; and
  wherein the (C$_3$-C$_6$) cycloalkyl or phenyl is optionally substituted by 1, 2, or 3 substituents independently selected from the group consisting of halogen, CN, CF$_3$, (C$_1$-C$_4$) alkyl, and O(C$_1$-C$_4$) alkyl; and
R$^{10}$ is H, (C$_1$-C$_4$) alkyl, (C$_3$-C$_6$) cycloalkyl, or phenyl;
  wherein the (C$_1$-C$_4$) alkyl is optionally substituted by 1, 2, 3, 4, or 5 substituents independently selected from the group consisting of F, CN, OH, O(C$_1$-C$_4$) alkyl, and (C$_3$-C$_6$) cycloalkyl; and
  wherein the (C$_3$-C$_6$) cycloalkyl or phenyl is optionally substituted by 1, 2, or 3 substituents independently selected from the group consisting of halogen, CN, CF$_3$, (C$_1$-C$_4$) alkyl, and O(C$_1$-C$_4$) alkyl;
with the provisos that:
(1) if R$^{11}$ is H, then at least one of R$^{12}$, R$^{13A}$, or R$^{13B}$ is not H; and
(2) if R$^{11}$ is CN, (C$_1$-C$_4$) alkyl, C(O)H, or C(O)CH$_3$, then R$^{12}$, R$^{13A}$, and R$^{13B}$ are H;
wherein the process comprises the following steps:
(A) reacting a compound of formula (II):

(II)

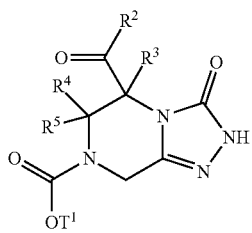

wherein:
(iii) R² is:

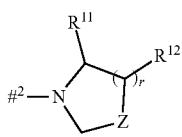

wherein:
r is 0 or 1;
Z is —$CR^{13A}R^{13B}$—, —$NR^{14}$—, —O—, —S—, —S(O)—, or —$S(O)_2$—;
$R^{11}$ is H, CN, ($C_1$-$C_4$) alkyl, C(O)H, or C(O)$CH_3$;
  wherein the ($C_1$-$C_4$) alkyl is optionally substituted by 1, 2, 3, 4, or 5 substituents independently selected from the group consisting of F and OH; and
  wherein the C(O)$CH_3$ is optionally substituted by 1, 2, or 3 substituents independently selected from the group consisting of F and OH;
$R^{12}$ is H, F, or ($C_1$-$C_4$) alkyl;
$R^{13A}$ is H, halogen, CN, ($C_1$-$C_4$) alkyl, $CH_2F$, $CHF_2$, $CF_3$, OH, O($C_1$-$C_4$) alkyl, $OCHF_2$, $OCF_3$, $OCH_2CF_3$, ($C_3$-$C_6$) cycloalkyl, or ($C_3$-$C_5$) cycloalkoxy:
  wherein the ($C_1$-$C_4$) alkyl is optionally substituted by 1, 2, 3, 4, or 5 substituents independently selected from the group consisting of $NH_2$, NH($C_1$-$C_4$) alkyl, N[($C_1$-$C_4$) alkyl]$_2$, and OH;
$R^{13B}$ is H, F, or ($C_1$-$C_4$) alkyl,
  wherein the ($C_1$-$C_4$) alkyl is optionally substituted by 1, 2, 3, 4, or 5 F substituents; or
$R^{11}$ and $R^{12}$, together with the carbon atoms to which they are attached, form cyclopropyl or cyclobutyl;
  wherein the cyclopropyl or cyclobutyl is optionally substituted by 1 or 2 F substituents; or
$R^{12}$ and $R^{13A}$, together with the carbon atoms to which they are attached, form cyclopropyl or cyclobutyl;
  wherein the cyclopropyl or cyclobutyl is optionally substituted by 1 or 2 F substituents; or
$R^{13A}$ and $R^{13B}$, together with the carbon atoms to which they are attached, form cyclopropyl or cyclobutyl;
  wherein the cyclopropyl or cyclobutyl is optionally substituted by 1 or 2 F substituents;
$R^{14}$ is H or $CH_3$; and
$\#^2$ is the point of attachment to —C(O)—; or
(iv) $R^2$ is:

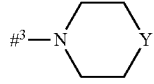

wherein:
Y is —$CR^{16A}R^{16B}$—, —$NR^{15}$—, —O—, or —S—;
$R^{15}$ is H or $CH_3$;
$R^{16A}$ is H or $CH_3$;
$R^{16B}$ is H or $CH_3$; and
$\#^3$ is the point of attachment to —C(O)—;
$R^3$ is H;
$R^4$ is H or ($C_1$-$C_4$) alkyl;
  wherein the ($C_1$-$C_4$) alkyl is optionally substituted by 1, 2, 3, 4, or 5 substituents independently selected from the group consisting of F, NH($C_1$-$C_4$) alkyl, N[($C_1$-$C_4$) alkyl]$_2$, OH, and O($C_1$-$C_4$) alkyl;
$R^5$ is H; and
$T^1$ is $C_{1-4}$ alkyl or $CH_2Ph$;

with the provisos that:
(1) if $R^{11}$ is H, then at least one of $R^{12}$, $R^{13A}$, or $R^{13B}$ is not H; and
(2) if $R^{11}$ is CN, ($C_1$-$C_4$) alkyl, C(O)H, or C(O)$CH_3$, then $R^{12}$, $R^{13A}$ and $R^{13B}$ are H;
with a compound of formula (III):

$X^1$-A-$R^1$  (III)

wherein:
(i) A is —$CD_2$- or —($C_1$-$C_4$) alkylene-, wherein the ($C_1$-$C_4$) alkylene is optionally substituted by 1 or more substituents independently selected from the group consisting of F, OH, and O($C_1$-$C_4$) alkyl; or
(ii) A is:

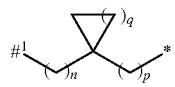

wherein:
n is 0 or 1;
p is 0 or 1;
q is 1 or 2;
$\#^1$ is the point of attachment to the nitrogen atom of the 5-oxo-4,5-dihydro-1H-1,2,4-triazol-1-yl ring; and
* is the point of attachment to $R^1$;
$R^1$ is ($C_3$-$C_7$) cycloalkyl, phenyl, or 5- to 10-membered heteroaryl;
  wherein the ($C_3$-$C_7$) cycloalkyl is optionally substituted by 1, 2, or 3 substituents independently selected from the group consisting of halogen, CN, ($C_1$-$C_4$) alkyl, $CF_3$, and O($C_1$-$C_4$) alkyl;
  wherein the phenyl is substituted by 1, 2, 3, or 4 substituents independently selected from the group consisting of halogen, CN, ($C_1$-$C_4$) alkyl, $CF_3$, C(O)$NH_2$, C(O)NH($C_1$-$C_4$) alkyl, C(O)N[($C_1$-$C_4$) alkyl]$_2$, C(O)NH($C_3$-$C_5$) cycloalkyl, C(O)OH, C(O)O($C_1$-$C_4$) alkyl, $NH_2$, NH($C_1$-$C_4$) alkyl, N[($C_1$-$C_4$) alkyl]$_2$, O($C_1$-$C_4$) alkyl, $OCH_2F$, $OCHF_2$, $OCF_3$, S($C_1$-$C_4$) alkyl, S(O)($C_1$-$C_4$) alkyl, $S(O)_2$($C_1$-$C_4$) alkyl, $S(O)_2NH_2$, $S(O)_2$NH($C_1$-$C_4$) alkyl, $S(O)_2$N[($C_1$-$C_4$) alkyl]$_2$, $S(O)_2$($C_3$-$C_4$) cycloalkyl, ($C_3$-$C_6$) cycloalkyl, and ($C_3$-$C_5$) cycloalkoxy;
  wherein the 5- to 10-membered heteroaryl is substituted by 1, 2, 3, or 4 substituents independently selected from the group consisting of halogen, CN, ($C_1$-$C_4$) alkyl, $CF_3$, C(O)$NH_2$, C(O)NH($C_1$-$C_4$) alkyl, C(O)N[($C_1$-$C_4$) alkyl]$_2$, C(O)NH($C_3$-$C_5$) cycloalkyl, C(O)OH, C(O)O($C_1$-$C_4$) alkyl, $NH_2$, NH($C_1$-$C_4$) alkyl, N[($C_1$-$C_4$) alkyl]$_2$, O($C_1$-$C_4$) alkyl, $OCHF_2$, $OCF_3$, $OCH_2CF_3$, S($C_1$-$C_4$) alkyl, S(O)($C_1$-$C_4$) alkyl, $S(O)_2$($C_1$-$C_4$) alkyl, $S(O)_2NH_2$, $S(O)_2$NH($C_1$-$C_4$) alkyl, $S(O)_2$N[($C_1$-$C_4$) alkyl]$_2$, $S(O)_2$($C_3$-$C_4$) cycloalkyl, ($C_3$-$C_6$) cycloalkyl, ($C_3$-$C_5$) cycloalkoxy, and phenyl; and
  wherein each phenyl substituent of the 5- to 10-membered heteroaryl is optionally and independently substituted by 1, 2, 3, 4, or 5 substituents independently selected from the group consisting of F, Cl, $CH_3$, $CH_2CH_3$, and $OCH_3$; and $X^1$ is Cl, Br, I, OH, OS(O)$_2$CH$_3$, OS(O)$_2$CF$_3$, OS(O)$_2$CF$_2$CF$_2$CF$_3$, OS(O)$_2$-(4-methylphenyl), or OS(O)$_2$-(4-nitrophenyl);

in the presence of a base and an inert solvent, to give a compound of formula (IV):

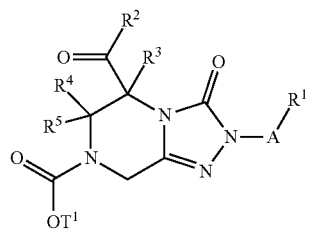

(IV)

wherein:
(i) A is —CD$_2$- or —(C$_1$-C$_4$) alkylene-, wherein the (C$_1$-C$_4$) alkylene is optionally substituted by 1 or more substituents independently selected from the group consisting of F, OH, and O(C$_1$-C$_4$) alkyl; or
(ii) A is:

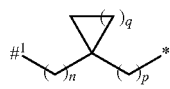

wherein:
n is 0 or 1;
p is 0 or 1;
q is 1 or 2;
$^1$ is the point of attachment to the nitrogen atom of the 5-oxo-4,5-dihydro-1H-1,2,4-triazol-1-yl ring; and
* is the point of attachment to R$^1$;
R$^1$ is (C$_3$-C$_7$) cycloalkyl, phenyl, or 5- to 10-membered heteroaryl;
wherein the (C$_3$-C$_7$) cycloalkyl is optionally substituted by 1, 2, or 3 substituents independently selected from the group consisting of halogen, CN, (C$_1$-C$_4$) alkyl, CF$_3$, and O(C$_1$-C$_4$) alkyl;
wherein the phenyl is substituted by 1, 2, 3, or 4 substituents independently selected from the group consisting of halogen, CN, (C$_1$-C$_4$) alkyl, CF$_3$, C(O)NH$_2$, C(O)NH(C$_1$-C$_4$) alkyl, C(O)N[(C$_1$-C$_4$) alkyl]$_2$, C(O)NH(C$_3$-C$_5$) cycloalkyl, C(O)OH, C(O)O(C$_1$-C$_4$) alkyl, NH$_2$, NH(C$_1$-C$_4$) alkyl, N[(C$_1$-C$_4$) alkyl]$_2$, O(C$_1$-C$_4$) alkyl, OCH$_2$F, OCHF$_2$, OCF$_3$, S(C$_1$-C$_4$) alkyl, S(O)(C$_1$-C$_4$) alkyl, S(O)$_2$(C$_1$-C$_4$) alkyl, S(O)$_2$NH$_2$, S(O)$_2$NH(C$_1$-C$_4$) alkyl, S(O)$_2$N[(C$_1$-C$_4$) alkyl]$_2$, S(O)$_2$(C$_3$-C$_4$) cycloalkyl, (C$_3$-C$_6$) cycloalkyl, and (C$_3$-C$_5$) cycloalkoxy;
wherein the 5- to 10-membered heteroaryl is substituted by 1, 2, 3, or 4 substituents independently selected from the group consisting of halogen, CN, (C$_1$-C$_4$) alkyl, CF$_3$, C(O)NH$_2$, C(O)NH(C$_1$-C$_4$) alkyl, C(O)N[(C$_1$-C$_4$) alkyl]$_2$, C(O)NH(C$_3$-C$_5$) cycloalkyl, C(O)OH, C(O)O(C$_1$-C$_4$) alkyl, NH$_2$, NH(C$_1$-C$_4$) alkyl, N[(C$_1$-C$_4$) alkyl]$_2$, O(C$_1$-C$_4$) alkyl, OCHF$_2$, OCF$_3$, OCH$_2$CF$_3$, S(C$_1$-C$_4$) alkyl, S(O)(C$_1$-C$_4$) alkyl, S(O)$_2$(C$_1$-C$_4$) alkyl, S(O)$_2$NH$_2$, S(O)$_2$NH(C$_1$-C$_4$) alkyl, S(O)$_2$N[(C$_1$-C$_4$) alkyl]$_2$, S(O)$_2$(C$_3$-C$_4$) cycloalkyl, (C$_3$-C$_6$) cycloalkyl, (C$_3$-C$_5$) cycloalkoxy, and phenyl; and
wherein each phenyl substituent of the 5- to 10-membered heteroaryl is optionally and independently substituted by 1, 2, 3, 4, or 5 substituents independently selected from the group consisting of F, Cl, CH$_3$, CH$_2$CH$_3$, and OCH$_3$;
(iii) R$^2$ is:

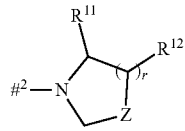

wherein:
r is 0 or 1;
Z is —CR$^{13A}$R$^{13B}$—, —NR$^{14}$—, —O—, —S—, —S(O)—, or —S(O)$_2$—;
R$^{11}$ is H, CN, (C$_1$-C$_4$) alkyl, C(O)H, or C(O)CH$_3$;
wherein the (C$_1$-C$_4$) alkyl is optionally substituted by 1, 2, 3, 4, or 5 substituents independently selected from the group consisting of F and OH; and
wherein the C(O)CH$_3$ is optionally substituted by 1, 2, or 3 substituents independently selected from the group consisting of F and OH;
R$^{12}$ is H, F, or (C$_1$-C$_4$) alkyl;
R$^{13A}$ is H, halogen, CN, (C$_1$-C$_4$) alkyl, CH$_2$F, CHF$_2$, CF$_3$, OH, O(C$_1$-C$_4$) alkyl, OCHF$_2$, OCF$_3$, OCH$_2$CF$_3$, (C$_3$-C$_6$) cycloalkyl, or (C$_3$-C$_5$) cycloalkoxy:
wherein the (C$_1$-C$_4$) alkyl is optionally substituted by 1, 2, 3, 4, or 5 substituents independently selected from the group consisting of NH$_2$, NH(C$_1$-C$_4$) alkyl, N[(C$_1$-C$_4$) alkyl]$_2$, and OH;
R$^{13B}$ is H, F, or (C$_1$-C$_4$) alkyl,
wherein the (C$_1$-C$_4$) alkyl is optionally substituted by 1, 2, 3, 4, or 5 F substituents; or
R$^{11}$ and R$^{12}$, together with the carbon atoms to which they are attached, form cyclopropyl or cyclobutyl;
wherein the cyclopropyl or cyclobutyl is optionally substituted by 1 or 2 F substituents; or
R$^{12}$ and R$^{13A}$, together with the carbon atoms to which they are attached, form cyclopropyl or cyclobutyl;
wherein the cyclopropyl or cyclobutyl is optionally substituted by 1 or 2 F substituents; or
R$^{13A}$ and R$^{13B}$, together with the carbon atoms to which they are attached, form cyclopropyl or cyclobutyl;
wherein the cyclopropyl or cyclobutyl is optionally substituted by 1 or 2 F substituents;
R$^{14}$ is H or CH$_3$; and
$^2$ is the point of attachment to —C(O)—; or (iv) $R^2$ is:

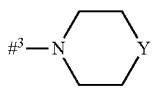

wherein:
Y is —$CR^{16A}R^{16B}$—, —$NR^{15}$—, —O—, or —S—;
$R^{15}$ is H or $CH_3$;
$R^{16A}$ is H or $CH_3$;
$R^{16B}$ is H or $CH_3$; and
$\#^3$ is the point of attachment to —C(O)—;
$R^3$ is H;
$R^4$ is H or ($C_1$-$C_4$) alkyl;
wherein the ($C_1$-$C_4$) alkyl is optionally substituted by 1, 2, 3, 4, or 5 substituents independently selected from the group consisting of F, $NH(C_1$-$C_4)$ alkyl, $N[(C_1$-$C_4)$ alkyl$]_2$, OH, and $O(C_1$-$C_4)$ alkyl;
$R^5$ is H; and
$T^1$ is $C_{1-4}$ alkyl or $CH_2Ph$;
with the provisos that:
(1) if $R^{11}$ is H, then at least one of $R^{12}$, $R^{13A}$, or $R^{13B}$ is not H; and
(2) if $R^{11}$ is CN, ($C_1$-$C_4$) alkyl, C(O)H, or C(O)$CH_3$, then $R^{12}$, $R^{13A}$, and $R^{13B}$ are H;
deprotecting the compound of formula (IV) above, in the presence of an acid or a base, to give a compound of formula (V):

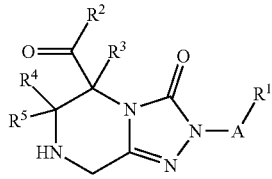

(V)

wherein:
(i) A is —$CD_2$- or —($C_1$-$C_4$) alkylene-, wherein the ($C_1$-$C_4$) alkylene is optionally substituted by 1 or more substituents independently selected from the group consisting of F, OH, and O($C_1$-$C_4$) alkyl; or
(ii) A is:

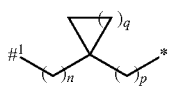

wherein:
n is 0 or 1;
p is 0 or 1;
q is 1 or 2;
$\#^1$ is the point of attachment to the nitrogen atom of the 5-oxo-4,5-dihydro-1H-1,2,4-triazol-1-yl ring; and
* is the point of attachment to $R^1$;
$R^1$ is ($C_3$-$C_7$) cycloalkyl, phenyl, or 5- to 10-membered heteroaryl;

wherein the ($C_3$-$C_7$) cycloalkyl is optionally substituted by 1, 2, or 3 substituents independently selected from the group consisting of halogen, CN, ($C_1$-$C_4$) alkyl, $CF_3$, and O($C_1$-$C_4$) alkyl;
wherein the phenyl is substituted by 1, 2, 3, or 4 substituents independently selected from the group consisting of halogen, CN, ($C_1$-$C_4$) alkyl, $CF_3$, C(O)$NH_2$, C(O)NH($C_1$-$C_4$) alkyl, C(O)N[($C_1$-$C_4$) alkyl$]_2$, C(O)NH($C_3$-$C_5$) cycloalkyl, C(O)OH, C(O)O($C_1$-$C_4$) alkyl, $NH_2$, NH($C_1$-$C_4$) alkyl, N[($C_1$-$C_4$) alkyl$]_2$, O($C_1$-$C_4$) alkyl, $OCH_2F$, $OCHF_2$, $OCF_3$, S($C_1$-$C_4$) alkyl, S(O)($C_1$-$C_4$) alkyl, $S(O)_2$($C_1$-$C_4$) alkyl, $S(O)_2NH_2$, $S(O)_2NH$($C_1$-$C_4$) alkyl, $S(O)_2N[$($C_1$-$C_4$) alkyl$]_2$, $S(O)_2$($C_3$-$C_4$) cycloalkyl, ($C_3$-$C_6$) cycloalkyl, and ($C_3$-$C_5$) cycloalkoxy;
wherein the 5- to 10-membered heteroaryl is substituted by 1, 2, 3, or 4 substituents independently selected from the group consisting of halogen, CN, ($C_1$-$C_4$) alkyl, $CF_3$, C(O)$NH_2$, C(O)NH($C_1$-$C_4$) alkyl, C(O)N[($C_1$-$C_4$) alkyl$]_2$, C(O)NH($C_3$-$C_5$) cycloalkyl, C(O)OH, C(O)O($C_1$-$C_4$) alkyl, $NH_2$, NH($C_1$-$C_4$) alkyl, N[($C_1$-$C_4$) alkyl$]_2$, O($C_1$-$C_4$) alkyl, $OCHF_2$, $OCF_3$, $OCH_2CF_3$, S($C_1$-$C_4$) alkyl, S(O)($C_1$-$C_4$) alkyl, $S(O)_2$($C_1$-$C_4$) alkyl, $S(O)_2NH_2$, $S(O)_2NH$($C_1$-$C_4$) alkyl, $S(O)_2N[$($C_1$-$C_4$) alkyl$]_2$, $S(O)_2$($C_3$-$C_4$) cycloalkyl, ($C_3$-$C_6$) cycloalkyl, ($C_3$-$C_5$) cycloalkoxy, and phenyl; and
wherein each phenyl substituent of the 5- to 10-membered heteroaryl is optionally and independently substituted by 1, 2, 3, 4, or 5 substituents independently selected from the group consisting of F, Cl, $CH_3$, $CH_2CH_3$, and $OCH_3$;
(iii) $R^2$ is:

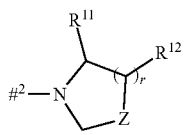

wherein:
r is 0 or 1;
Z is —$CR^{13A}R^{13B}$—, —$NR^{14}$—, —O—, —S—, —S(O)—, or —$S(O)_2$—;
$R^{11}$ is H, CN, ($C_1$-$C_4$) alkyl, C(O)H, or C(O)$CH_3$;
wherein the ($C_1$-$C_4$) alkyl is optionally substituted by 1, 2, 3, 4, or 5 substituents independently selected from the group consisting of F and OH; and
wherein the C(O)$CH_3$ is optionally substituted by 1, 2, or 3 substituents independently selected from the group consisting of F and OH;
$R^{12}$ is H, F, or ($C_1$-$C_4$) alkyl;
$R^{13A}$ is H, halogen, CN, ($C_1$-$C_4$) alkyl, $CH_2F$, $CHF_2$, $CF_3$, OH, O($C_1$-$C_4$) alkyl, $OCHF_2$, $OCF_3$, $OCH_2CF_3$, ($C_3$-$C_6$) cycloalkyl, or ($C_3$-$C_5$) cycloalkoxy:
wherein the ($C_1$-$C_4$) alkyl is optionally substituted by 1, 2, 3, 4, or 5 substituents independently selected from the group consisting of $NH_2$, NH($C_1$-$C_4$) alkyl, N[($C_1$-$C_4$) alkyl]-, and OH;
$R^{13B}$ is H, F, or ($C_1$-$C_4$) alkyl,
wherein the ($C_1$-$C_4$) alkyl is optionally substituted by 1, 2, 3, 4, or 5 F substituents; or $R^{11}$ and $R^{12}$, together with the carbon atoms to which they are attached, form cyclopropyl or cyclobutyl;
  wherein the cyclopropyl or cyclobutyl is optionally substituted by 1 or 2 F substituents; or
$R^{12}$ and $R^{13A}$, together with the carbon atoms to which they are attached, form cyclopropyl or cyclobutyl;
  wherein the cyclopropyl or cyclobutyl is optionally substituted by 1 or 2 F substituents; or
$R^{13A}$ and $R^{13B}$, together with the carbon atoms to which they are attached, form cyclopropyl or cyclobutyl;
  wherein the cyclopropyl or cyclobutyl is optionally substituted by 1 or 2 F substituents;
$R^{14}$ is H or $CH_3$; and
$\#^2$ is the point of attachment to —C(O)—; or
(iv) $R^2$ is:

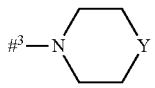

wherein:
  Y is $-CR^{16A}R^{16B}-$, $-NR^{15}-$, $-O-$, or $-S-$;
  $R^{15}$ is H or $CH_3$;
  $R^{16A}$ is H or $CH_3$;
  $R^{16B}$ is H or $CH_3$; and
  $\#^3$ is the point of attachment to —C(O)—;
$R^3$ is H;
$R^4$ is H or $(C_1\text{-}C_4)$ alkyl;
  wherein the $(C_1\text{-}C_4)$ alkyl is optionally substituted by 1, 2, 3, 4, or 5 substituents independently selected from the group consisting of F, $NH(C_1\text{-}C_4)$ alkyl, $N[(C_1\text{-}C_4)$ alkyl$]_2$, OH, and $O(C_1\text{-}C_4)$ alkyl; and
$R^5$ is H;
with the provisos that:
(1) if $R^{11}$ is H, then at least one of $R^{12}$, $R^{13A}$, or $R^{13B}$ is not H; and
(2) if $R^{11}$ is CN, $(C_1\text{-}C_4)$ alkyl, C(O)H, or $C(O)CH_3$, then $R^{12}$, $R^{13A}$ and $R^{13B}$ are H; and
(A1) reacting the compound of formula (V) above with a compound of the formula (VI):

wherein:
  $R^{10}$ is H, $(C_1\text{-}C_4)$ alkyl, $(C_3\text{-}C_6)$ cycloalkyl, or phenyl;
    wherein the $(C_1\text{-}C_4)$ alkyl is optionally substituted by 1, 2, 3, 4, or 5 substituents independently selected from the group consisting of F, CN, OH, $O(C_1\text{-}C_4)$ alkyl, and $(C_3\text{-}C_6)$ cycloalkyl; and
    wherein the $(C_3\text{-}C_6)$ cycloalkyl or phenyl is optionally substituted by 1, 2, or 3 substituents independently selected from the group consisting of halogen, CN, $CF_3$, $(C_1\text{-}C_4)$ alkyl, and $O(C_1\text{-}C_4)$ alkyl;
  $X^2$ is Cl, Br, I, OH, $OS(O)_2CH_3$, $OS(O)_2CF_3$, $OS(O)_2CF_2CF_2CF_2CF_3$, $OS(O)_2$-(4-methylphenyl), or $OS(O)_2$-(4-nitrophenyl);
in the presence of a base and optionally an inert solvent, to give the compound of formula (I) above; or (A2) reacting the compound of formula (V) above with a compound of the formula (VII):

wherein:
  $R^6$ is $(C_1\text{-}C_6)$ alkyl, $(C_3\text{-}C_6)$ cycloalkyl, phenyl, or 5- or 6-membered heteroaryl;
    wherein the $(C_1\text{-}C_6)$ alkyl is optionally substituted by 1, 2, 3, 4, or 5 substituents independently selected from the group consisting of F, CN, OH, and $O(C_1\text{-}C_4)$ alkyl; and
    wherein the $(C_3\text{-}C_6)$ cycloalkyl, phenyl, or 5- or 6-membered heteroaryl is optionally substituted by 1, 2, or 3 substituents independently selected from the group consisting of halogen, CN, $CF_3$, $(C_1\text{-}C_4)$ alkyl, and $O(C_1\text{-}C_4)$ alkyl;
in the presence of a base, to give the compound of formula (I) above; or
(A3) reacting the compound of formula (V) above with a compound of the formula (VIII):

wherein:
  $R^8$ is $(C_1\text{-}C_4)$ alkyl, $(C_3\text{-}C_6)$ cycloalkyl, phenyl, or 5- or 6-membered heteroaryl;
    wherein the $(C_1\text{-}C_4)$ alkyl is optionally substituted by 1, 2, 3, 4, or 5 substituents independently selected from the group consisting of F, CN, OH, and $O(C_1\text{-}C_4)$ alkyl; and
    wherein the $(C_3\text{-}C_6)$ cycloalkyl, phenyl, or 5- or 6-membered heteroaryl is optionally substituted by 1, 2, or 3 substituents independently selected from the group consisting of halogen, CN, $CF_3$, $(C_1\text{-}C_4)$ alkyl, and $O(C_1\text{-}C_4)$ alkyl; and
  $X^3$ is Cl, Br, I, OH, $OS(O)_2CH_3$, $OS(O)_2CF_3$, $OS(O)_2CF_2CF_2CF_2CF_3$, $OS(O)_2$-(4-methylphenyl), or $OS(O)_2$-(4-nitrophenyl);
in the presence of a base, to give the compound of formula (I) above; and
optionally reacting the compound of formula (I) above with a pharmaceutically acceptable acid or a pharmaceutically acceptable base, optionally in the presence of an inert solvent, to give a pharmaceutically acceptable salt of the compound of formula (I) above.

25. The process according to claim 24, wherein $X^1$ is Cl, Br, I, OH, $OS(O)_2CH_3$, $OS(O)_2CF_3$, $OS(O)_2CF_2CF_2CF_2CF_3$, or $OS(O)_2$-(4-methylphenyl).

26. The process according to claim 24, wherein $X^2$ is Cl, Br, I, OH, $OS(O)_2CH_3$, $OS(O)_2CF_3$, $OS(O)_2CF_2CF_2CF_2CF_3$, or $OS(O)_2$-(4-methylphenyl).

27. The process according to claim 24, wherein $X^3$ is Cl, Br, or OH.

28. A process for preparing a compound of formula (I) according to claim 1:

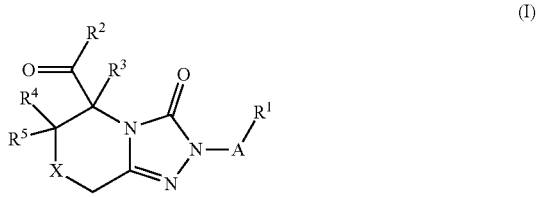

or a pharmaceutically acceptable salt thereof, wherein:
(i) A is —CD$_2$- or —(C$_1$-C$_4$) alkylene-, wherein the (C$_1$-C$_4$) alkylene is optionally substituted by 1 or more substituents independently selected from the group consisting of F, OH, and O(C$_1$-C$_4$) alkyl; or
(ii) A is:

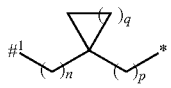

wherein:
n is 0 or 1;
p is 0 or 1;
q is 1 or 2;
$^1$ is the point of attachment to the nitrogen atom of the 5-oxo-4,5-dihydro-1H-1,2,4-triazol-1-yl ring; and
* is the point of attachment to R$^1$;
X is —N(R$^{10}$)—, —N[C(O)R$^8$]—, —N[C(O)NR$^6$R$^7$]—, or —N[C(O)OR$^9$]—;
R$^1$ is (C$_3$-C$_7$) cycloalkyl, phenyl, or 5- to 10-membered heteroaryl;
wherein the (C$_3$-C$_7$) cycloalkyl is optionally substituted by 1, 2, or 3 substituents independently selected from the group consisting of halogen, CN, (C$_1$-C$_4$) alkyl, CF$_3$, and O(C$_1$-C$_4$) alkyl;
wherein the phenyl is substituted by 1, 2, 3, or 4 substituents independently selected from the group consisting of halogen, CN, (C$_1$-C$_4$) alkyl, CF$_3$, C(O)NH$_2$, C(O)NH(C$_1$-C$_4$) alkyl, C(O)N[(C$_1$-C$_4$) alkyl]$_2$, C(O)NH(C$_3$-C$_5$) cycloalkyl, C(O)OH, C(O)O(C$_1$-C$_4$) alkyl, NH$_2$, NH(C$_1$-C$_4$) alkyl, N[(C$_1$-C$_4$) alkyl]$_2$, O(C$_1$-C$_4$) alkyl, OCH$_2$F, OCHF$_2$, OCF$_3$, S(C$_1$-C$_4$) alkyl, S(O)(C$_1$-C$_4$) alkyl, S(O)$_2$(C$_1$-C$_4$) alkyl, S(O)$_2$NH$_2$, S(O)$_2$NH(C$_1$-C$_4$) alkyl, S(O)$_2$N[(C$_1$-C$_4$) alkyl]$_2$, S(O)$_2$(C$_3$-C$_4$) cycloalkyl, (C$_3$-C$_6$) cycloalkyl, and (C$_3$-C$_5$) cycloalkoxy;
wherein the 5- to 10-membered heteroaryl is substituted by 1, 2, 3, or 4 substituents independently selected from the group consisting of halogen, CN, (C$_1$-C$_4$) alkyl, CF$_3$, C(O)NH$_2$, C(O)NH(C$_1$-C$_4$) alkyl, C(O)N[(C$_1$-C$_4$) alkyl]$_2$, C(O)NH(C$_3$-C$_5$) cycloalkyl, C(O)OH, C(O)O(C$_1$-C$_4$) alkyl, NH$_2$, NH(C$_1$-C$_4$) alkyl, N[(C$_1$-C$_4$) alkyl]$_2$, O(C$_1$-C$_4$) alkyl, OCHF$_2$, OCF$_3$, OCH$_2$CF$_3$, S(C$_1$-C$_4$) alkyl, S(O)(C$_1$-C$_4$) alkyl, S(O)$_2$(C$_1$-C$_4$) alkyl, S(O)$_2$NH$_2$, S(O)$_2$NH(C$_1$-C$_4$) alkyl, S(O)$_2$N[(C$_1$-C$_4$) alkyl]$_2$, S(O)$_2$(C$_3$-C$_4$) cycloalkyl, (C$_3$-C$_6$) cycloalkyl, (C$_3$-C$_5$) cycloalkoxy, and phenyl; and
wherein each phenyl substituent of the 5- to 10-membered heteroaryl is optionally and independently substituted by 1, 2, 3, 4, or 5 substituents independently selected from the group consisting of F, Cl, CH$_3$, CH$_2$CH$_3$, and OCH$_3$;
(iii) R$^2$ is:

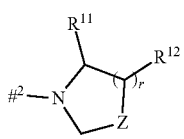

wherein:
r is 0 or 1;
Z is —CR$^{13A}$R$^{13B}$—, —NR$^{14}$—, —O—, —S—, —S(O)—, or —S(O)$_2$—;
R$^{11}$ is H, CN, (C$_1$-C$_4$) alkyl, C(O)H, or C(O)CH$_3$;
wherein the (C$_1$-C$_4$) alkyl is optionally substituted by 1, 2, 3, 4, or 5 substituents independently selected from the group consisting of F and OH; and
wherein the C(O)CH$_3$ is optionally substituted by 1, 2, or 3 substituents independently selected from the group consisting of F and OH;
R$^{12}$ is H, F, or (C$_1$-C$_4$) alkyl;
R$^{13A}$ is H, halogen, CN, (C$_1$-C$_4$) alkyl, CH$_2$F, CHF$_2$, CF$_3$, OH, O(C$_1$-C$_4$) alkyl, OCHF$_2$, OCF$_3$, OCH$_2$CF$_3$, (C$_3$-C$_6$) cycloalkyl, or (C$_3$-C$_5$) cycloalkoxy:
wherein the (C$_1$-C$_4$) alkyl is optionally substituted by 1, 2, 3, 4, or 5 substituents independently selected from the group consisting of NH$_2$, NH(C$_1$-C$_4$) alkyl, N[(C$_1$-C$_4$) alkyl]$_2$, and OH;
R$^{13B}$ is H, F, or (C$_1$-C$_4$) alkyl,
wherein the (C$_1$-C$_4$) alkyl is optionally substituted by 1, 2, 3, 4, or 5 F substituents; or
R$^{11}$ and R$^{12}$, together with the carbon atoms to which they are attached, form cyclopropyl or cyclobutyl;
wherein the cyclopropyl or cyclobutyl is optionally substituted by 1 or 2 F substituents; or
R$^{12}$ and R$^{13A}$, together with the carbon atoms to which they are attached, form cyclopropyl or cyclobutyl;
wherein the cyclopropyl or cyclobutyl is optionally substituted by 1 or 2 F substituents; or
R$^{13A}$ and R$^{13B}$, together with the carbon atoms to which they are attached, form cyclopropyl or cyclobutyl;
wherein the cyclopropyl or cyclobutyl is optionally substituted by 1 or 2 F substituents;
R$^{14}$ is H or CH$_3$; and
$^2$ is the point of attachment to —C(O)—; or
(iv) R$^2$ is:

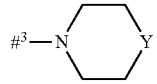

wherein:
Y is —CR$^{16A}$R$^{16B}$—, —NR$^{15}$—, —O—, or —S—;
R$^{15}$ is H or CH$_3$;
R$^{16A}$ is H or CH$_3$;
R$^{16B}$ is H or CH$_3$; and
$^3$ is the point of attachment to —C(O)—;
R$^3$ is H;
R$^4$ is H or (C$_1$-C$_4$) alkyl;
wherein the (C$_1$-C$_4$) alkyl is optionally substituted by 1, 2, 3, 4, or 5 substituents independently selected from the group consisting of F, NH(C$_1$-C$_4$) alkyl, N[(C$_1$-C$_4$) alkyl]$_2$, OH, and O(C$_1$-C$_4$) alkyl;
R$^5$ is H;
R$^6$ is (C$_1$-C$_6$) alkyl, (C$_3$-C$_6$) cycloalkyl, phenyl, or 5- or 6-membered heteroaryl;
wherein the (C$_1$-C$_6$) alkyl is optionally substituted by 1, 2, 3, 4, or 5 substituents independently selected from the group consisting of F, CN, OH, and O(C$_1$-C$_4$) alkyl; and
wherein the (C$_3$-C$_6$) cycloalkyl, phenyl, or 5- or 6-membered heteroaryl is optionally substituted by 1, 2, or 3 substituents independently selected from the group consisting of halogen, CN, CF$_3$, (C$_1$-C$_4$) alkyl, and O(C$_1$-C$_4$) alkyl;
R$^7$ is H or (C$_1$-C$_4$) alkyl;
wherein the (C$_1$-C$_4$) alkyl is optionally substituted by 1, 2, 3, 4, or 5 F substituents;

$R^8$ is $(C_1-C_4)$ alkyl, $(C_3-C_6)$ cycloalkyl, phenyl, or 5- or 6-membered heteroaryl;
  wherein the $(C_1-C_4)$ alkyl is optionally substituted by 1, 2, 3, 4, or 5 substituents independently selected from the group consisting of F, CN, OH, and $O(C_1-C_4)$ alkyl; and
  wherein the $(C_3-C_6)$ cycloalkyl, phenyl, or 5- or 6-membered heteroaryl is optionally substituted by 1, 2, or 3 substituents independently selected from the group consisting of halogen, CN, $CF_3$, $(C_1-C_4)$ alkyl, and $O(C_1-C_4)$ alkyl;
$R^9$ is $(C_1-C_4)$ alkyl, $(C_3-C_6)$ cycloalkyl, or phenyl;
  wherein the $(C_1-C_4)$ alkyl is optionally substituted by 1, 2, 3, 4, or 5 F substituents; and
  wherein the $(C_3-C_6)$ cycloalkyl or phenyl is optionally substituted by 1, 2, or 3 substituents independently selected from the group consisting of halogen, CN, $CF_3$, $(C_1-C_4)$ alkyl, and $O(C_1-C_4)$ alkyl; and
$R^{10}$ is H, $(C_1-C_4)$ alkyl, $(C_3-C_6)$ cycloalkyl, or phenyl;
  wherein the $(C_1-C_4)$ alkyl is optionally substituted by 1, 2, 3, 4, or 5 substituents independently selected from the group consisting of F, CN, OH, $O(C_1-C_4)$ alkyl, and $(C_3-C_6)$ cycloalkyl; and
  wherein the $(C_3-C_6)$ cycloalkyl or phenyl is optionally substituted by 1, 2, or 3 substituents independently selected from the group consisting of halogen, CN, $CF_3$, $(C_1-C_4)$ alkyl, and $O(C_1-C_4)$ alkyl;
with the provisos that:
(1) if $R^{11}$ is H, then at least one of $R^{12}$, $R^{13A}$, or $R^{13B}$ is not H; and
(2) if $R^{11}$ is CN, $(C_1-C_4)$ alkyl, C(O)H, or $C(O)CH_3$, then $R^{12}$, $R^{13A}$, and $R^{13B}$ are H;
wherein the process comprises the following steps:
(B) reacting a compound of formula (IX):

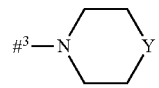

(IX)

wherein:
(iii) $R^2$ is:

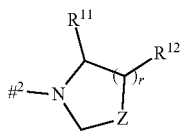

wherein:
r is 0 or 1;
Z is $-CR^{13A}R^{13B}-$, $-NR^{14}-$, $-O-$, $-S-$, $-S(O)-$, or $-S(O)_2-$;
$R^{11}$ is H, CN, $(C_1-C_4)$ alkyl, C(O)H, or $C(O)CH_3$;
  wherein the $(C_1-C_4)$ alkyl is optionally substituted by 1, 2, 3, 4, or 5 substituents independently selected from the group consisting of F and OH; and
  wherein the $C(O)CH_3$ is optionally substituted by 1, 2, or 3 substituents independently selected from the group consisting of F and OH;

$R^{12}$ is H, F, or $(C_1-C_4)$ alkyl;
$R^{13A}$ is H, halogen, CN, $(C_1-C_4)$ alkyl, $CH_2F$, $CHF_2$, $CF_3$, OH, $O(C_1-C_4)$ alkyl, $OCHF_2$, $OCF_3$, $OCH_2CF_3$, $(C_3-C_6)$ cycloalkyl, or $(C_3-C_5)$ cycloalkoxy;
  wherein the $(C_1-C_4)$ alkyl is optionally substituted by 1, 2, 3, 4, or 5 substituents independently selected from the group consisting of $NH_2$, $NH(C_1-C_4)$ alkyl, $N[(C_1-C_4) alkyl]_2$, and OH;
$R^{13B}$ is H, F, or $(C_1-C_4)$ alkyl,
  wherein the $(C_1-C_4)$ alkyl is optionally substituted by 1, 2, 3, 4, or 5 F substituents; or
$R^{11}$ and $R^{12}$, together with the carbon atoms to which they are attached, form cyclopropyl or cyclobutyl;
  wherein the cyclopropyl or cyclobutyl is optionally substituted by 1 or 2 F substituents; or
$R^{12}$ and $R^{13A}$, together with the carbon atoms to which they are attached, form cyclopropyl or cyclobutyl;
  wherein the cyclopropyl or cyclobutyl is optionally substituted by 1 or 2 F substituents; or
$R^{13A}$ and $R^{13B}$, together with the carbon atoms to which they are attached, form cyclopropyl or cyclobutyl;
  wherein the cyclopropyl or cyclobutyl is optionally substituted by 1 or 2 F substituents;
$R^{14}$ is H or $CH_3$; and
² is the point of attachment to —C(O)—; or
(iv) $R^2$ is:

wherein:
Y is $-CR^{16A}R^{16B}-$, $-NR^{15}-$, $-O-$, or $-S-$;
$R^{15}$ is H or $CH_3$;
$R^{16A}$ is H or $CH_3$;
$R^{16B}$ is H or $CH_3$; and
³ is the point of attachment to —C(O)—; and
$R^4$ is H or $(C_1-C_4)$ alkyl;
  wherein the $(C_1-C_4)$ alkyl is optionally substituted by 1, 2, 3, 4, or 5 substituents independently selected from the group consisting of F, $NH(C_1-C_4)$ alkyl, $N[(C_1-C_4) alkyl]_2$, OH, and $O(C_1-C_4)$ alkyl;
with the provisos that:
(1) if $R^{11}$ is H, then at least one of $R^{12}$, $R^{13A}$, or $R^{13B}$ is not H; and
(2) if $R^{11}$ is CN, $(C_1-C_4)$ alkyl, C(O)H, or $C(O)CH_3$, then $R^{12}$, $R^{13A}$, and $R^{13B}$ are H;
with a compound of formula (III):

$X^1$-A-$R^1$ (III)

wherein:
(i) A is $-CD_2-$ or $-(C_1-C_4)$ alkylene-, wherein the $(C_1-C_4)$ alkylene is optionally substituted by 1 or more substituents independently selected from the group consisting of F, OH, and $O(C_1-C_4)$ alkyl; or
(ii) A is:

wherein:
  n is 0 or 1;
  p is 0 or 1;
  q is 1 or 2;
  $\#^1$ is the point of attachment to the nitrogen atom of the 5-oxo-4,5-dihydro-1H-1,2,4-triazol-1-yl ring; and
  * is the point of attachment to $R^1$;
  $R^1$ is ($C_3$-$C_7$) cycloalkyl, phenyl, or 5- to 10-membered heteroaryl;
  wherein the ($C_3$-$C_7$) cycloalkyl is optionally substituted by 1, 2, or 3 substituents independently selected from the group consisting of halogen, CN, ($C_1$-$C_4$) alkyl, $CF_3$, and O($C_1$-$C_4$) alkyl;
  wherein the phenyl is substituted by 1, 2, 3, or 4 substituents independently selected from the group consisting of halogen, CN, ($C_1$-$C_4$) alkyl, $CF_3$, C(O)$NH_2$, C(O)NH($C_1$-$C_4$) alkyl, C(O)N[($C_1$-$C_4$) alkyl]$_2$, C(O)NH($C_3$-$C_5$) cycloalkyl, C(O)OH, C(O)O($C_1$-$C_4$) alkyl, $NH_2$, NH($C_1$-$C_4$) alkyl, N[($C_1$-$C_4$) alkyl]$_2$, O($C_1$-$C_4$) alkyl, $OCH_2F$, $OCHF_2$, $OCF_3$, S($C_1$-$C_4$) alkyl, S(O)($C_1$-$C_4$) alkyl, S(O)$_2$($C_1$-$C_4$) alkyl, S(O)$_2$$NH_2$, S(O)$_2$NH($C_1$-$C_4$) alkyl, S(O)$_2$N[($C_1$-$C_4$) alkyl]$_2$, S(O)$_2$($C_3$-$C_4$) cycloalkyl, ($C_3$-$C_6$) cycloalkyl, and ($C_3$-$C_5$) cycloalkoxy;
  wherein the 5- to 10-membered heteroaryl is substituted by 1, 2, 3, or 4 substituents independently selected from the group consisting of halogen, CN, ($C_1$-$C_4$) alkyl, $CF_3$, C(O)$NH_2$, C(O)NH($C_1$-$C_4$) alkyl, C(O)N[($C_1$-$C_4$) alkyl]$_2$, C(O)NH($C_3$-$C_5$) cycloalkyl, C(O)OH, C(O)O($C_1$-$C_4$) alkyl, $NH_2$, NH($C_1$-$C_4$) alkyl, N[($C_1$-$C_4$) alkyl]$_2$, O($C_1$-$C_4$) alkyl, $OCHF_2$, $OCF_3$, $OCH_2CF_3$, S($C_1$-$C_4$) alkyl, S(O)($C_1$-$C_4$) alkyl, S(O)$_2$($C_1$-$C_4$) alkyl, S(O)$_2$$NH_2$, S(O)$_2$NH($C_1$-$C_4$) alkyl, S(O)$_2$N[($C_1$-$C_4$) alkyl]$_2$, S(O)$_2$($C_3$-$C_4$) cycloalkyl, ($C_3$-$C_6$) cycloalkyl, ($C_3$-$C_5$) cycloalkoxy, and phenyl; and
  wherein each phenyl substituent of the 5- to 10-membered heteroaryl is optionally and independently substituted by 1, 2, 3, 4, or 5 substituents independently selected from the group consisting of F, Cl, $CH_3$, $CH_2CH_3$, and $OCH_3$; and
  $X^1$ is Cl, Br, I, OH, OS(O)$_2$$CH_3$, OS(O)$_2$$CF_3$, OS(O)$_2$$CF_2CF_2CF_2CF_3$, OS(O)$_2$-(4-methylphenyl), or OS(O)$_2$-(4-nitrophenyl);
in the presence of a base and an inert solvent, to give a compound of formula (X):

(X)

wherein:
(i) A is —$CD_2$- or —($C_1$-$C_4$) alkylene-, wherein the ($C_1$-$C_4$) alkylene is optionally substituted by 1 or more substituents independently selected from the group consisting of F, OH, and O($C_1$-$C_4$) alkyl; or (ii) A is:

wherein:
  n is 0 or 1;
  p is 0 or 1;
  q is 1 or 2;
  $\#^1$ is the point of attachment to the nitrogen atom of the 5-oxo-4,5-dihydro-1H-1,2,4-triazol-1-yl ring; and
  * is the point of attachment to $R^1$;
  $R^1$ is ($C_3$-$C_7$) cycloalkyl, phenyl, or 5- to 10-membered heteroaryl;
  wherein the ($C_3$-$C_7$) cycloalkyl is optionally substituted by 1, 2, or 3 substituents independently selected from the group consisting of halogen, CN, ($C_1$-$C_4$) alkyl, $CF_3$, and O($C_1$-$C_4$) alkyl;
  wherein the phenyl is substituted by 1, 2, 3, or 4 substituents independently selected from the group consisting of halogen, CN, ($C_1$-$C_4$) alkyl, $CF_3$, C(O)$NH_2$, C(O)NH($C_1$-$C_4$) alkyl, C(O)N[($C_1$-$C_4$) alkyl]$_2$, C(O)NH($C_3$-$C_5$) cycloalkyl, C(O)OH, C(O)O($C_1$-$C_4$) alkyl, $NH_2$, NH($C_1$-$C_4$) alkyl, N[($C_1$-$C_4$) alkyl]$_2$, O($C_1$-$C_4$) alkyl, $OCH_2F$, $OCHF_2$, $OCF_3$, S($C_1$-$C_4$) alkyl, S(O)($C_1$-$C_4$) alkyl, S(O)$_2$($C_1$-$C_4$) alkyl, S(O)$_2$$NH_2$, S(O)$_2$NH($C_1$-$C_4$) alkyl, S(O)$_2$N[($C_1$-$C_4$) alkyl]$_2$, S(O)$_2$($C_3$-$C_4$) cycloalkyl, ($C_3$-$C_6$) cycloalkyl, and ($C_3$-$C_5$) cycloalkoxy;
  wherein the 5- to 10-membered heteroaryl is substituted by 1, 2, 3, or 4 substituents independently selected from the group consisting of halogen, CN, ($C_1$-$C_4$) alkyl, $CF_3$, C(O)$NH_2$, C(O)NH($C_1$-$C_4$) alkyl, C(O)N[($C_1$-$C_4$) alkyl]$_2$, C(O)NH($C_3$-$C_5$) cycloalkyl, C(O)OH, C(O)O($C_1$-$C_4$) alkyl, $NH_2$, NH($C_1$-$C_4$) alkyl, N[($C_1$-$C_4$) alkyl]$_2$, O($C_1$-$C_4$) alkyl, $OCHF_2$, $OCF_3$, $OCH_2CF_3$, S($C_1$-$C_4$) alkyl, S(O)($C_1$-$C_4$) alkyl, S(O)$_2$($C_1$-$C_4$) alkyl, S(O)$_2$$NH_2$, S(O)$_2$NH($C_1$-$C_4$) alkyl, S(O)$_2$N[($C_1$-$C_4$) alkyl]$_2$, S(O)$_2$($C_3$-$C_4$) cycloalkyl, ($C_3$-$C_6$) cycloalkyl, ($C_3$-$C_5$) cycloalkoxy, and phenyl; and
  wherein each phenyl substituent of the 5- to 10-membered heteroaryl is optionally and independently substituted by 1, 2, 3, 4, or 5 substituents independently selected from the group consisting of F, Cl, $CH_3$, $CH_2CH_3$, and $OCH_3$;
(iii) $R^2$ is:

wherein:
  r is 0 or 1;
  Z is —$CR^{13A}R^{13B}$—, —$NR^{14}$—, —O—, —S—, —S(O)—, or —S(O)$_2$—;
  $R^{11}$ is H, CN, ($C_1$-$C_4$) alkyl, C(O)H, or C(O)$CH_3$;

wherein the (C$_1$-C$_4$) alkyl is optionally substituted by 1, 2, 3, 4, or 5 substituents independently selected from the group consisting of F and OH; and wherein the C(O)CH$_3$ is optionally substituted by 1, 2, or 3 substituents independently selected from the group consisting of F and OH;

R$^{12}$ is H, F, or (C$_1$-C$_4$) alkyl;

R$^{13A}$ is H, halogen, CN, (C$_1$-C$_4$) alkyl, CH$_2$F, CHF$_2$, CF$_3$, OH, O(C$_1$-C$_4$) alkyl, OCHF$_2$, OCF$_3$, OCH$_2$CF$_3$, (C$_3$-C$_6$) cycloalkyl, or (C$_3$-C$_5$) cycloalkoxy:

wherein the (C$_1$-C$_4$) alkyl is optionally substituted by 1, 2, 3, 4, or 5 substituents independently selected from the group consisting of NH$_2$, NH(C$_1$-C$_4$) alkyl, N[(C$_1$-C$_4$) alkyl]$_2$, and OH;

R$^{13B}$ is H, F, or (C$_1$-C$_4$) alkyl, wherein the (C$_1$-C$_4$) alkyl is optionally substituted by 1, 2, 3, 4, or 5 F substituents; or R$^{11}$ and R$^{12}$, together with the carbon atoms to which they are attached, form cyclopropyl or cyclobutyl;

wherein the cyclopropyl or cyclobutyl is optionally substituted by 1 or 2 F substituents; or R$^{12}$ and R$^{13A}$, together with the carbon atoms to which they are attached, form cyclopropyl or cyclobutyl;

wherein the cyclopropyl or cyclobutyl is optionally substituted by 1 or 2 F substituents; or R$^{13A}$ and R$^{13B}$, together with the carbon atoms to which they are attached, form cyclopropyl or cyclobutyl;

wherein the cyclopropyl or cyclobutyl is optionally substituted by 1 or 2 F substituents;

R$^{14}$ is H or CH$_3$; and

$^2$ is the point of attachment to —C(O)—; or (iv) R$^2$ is:

$^3$—N⌒Y wherein:
Y is —CR$^{16A}$R$^{16B}$—, —NR$^{15}$—, —O—, or —S—;
R$^{15}$ is H or CH$_3$;
R$^{16A}$ is H or CH$_3$;
R$^{16B}$ is H or CH$_3$; and
$^3$ is the point of attachment to —C(O)—; and R$^4$ is H or (C$_1$-C$_4$) alkyl;

wherein the (C$_1$-C$_4$) alkyl is optionally substituted by 1, 2, 3, 4, or 5 substituents independently selected from the group consisting of F, NH(C$_1$-C$_4$) alkyl, N[(C$_1$-C$_4$) alkyl]$_2$, OH, and O(C$_1$-C$_4$) alkyl;

with the provisos that:
(1) if R$^{11}$ is H, then at least one of R$^{12}$, R$^{13A}$, or R$^{13B}$ is not H; and
(2) if R$^{11}$ is CN, (C$_1$-C$_4$) alkyl, C(O)H, or C(O)CH$_3$, then R$^{12}$, R$^{13A}$, and R$^{13B}$ are H;

hydrogenating the compound of formula (X) above, in the presence of a palladium catalyst in a hydrogen atmosphere, to give a compound of formula (V):

(V)

wherein:
(i) A is —CD$_2$- or —(C$_1$-C$_4$) alkylene-, wherein the (C$_1$-C$_4$) alkylene is optionally substituted by 1 or more substituents independently selected from the group consisting of F, OH, and O(C$_1$-C$_4$) alkyl; or
(ii) A is:

wherein:
n is 0 or 1;
p is 0 or 1;
q is 1 or 2;
$^1$ is the point of attachment to the nitrogen atom of the 5-oxo-4,5-dihydro-1H-1,2,4-triazol-1-yl ring; and
* is the point of attachment to R$^1$;

R$^1$ is (C$_3$-C$_7$) cycloalkyl, phenyl, or 5- to 10-membered heteroaryl;

wherein the (C$_3$-C$_7$) cycloalkyl is optionally substituted by 1, 2, or 3 substituents independently selected from the group consisting of halogen, CN, (C$_1$-C$_4$) alkyl, CF$_3$, and O(C$_1$-C$_4$) alkyl;

wherein the phenyl is substituted by 1, 2, 3, or 4 substituents independently selected from the group consisting of halogen, CN, (C$_1$-C$_4$) alkyl, CF$_3$, C(O)NH$_2$, C(O)NH(C$_1$-C$_4$) alkyl, C(O)N[(C$_1$-C$_4$) alkyl]$_2$, C(O)NH(C$_3$-C$_5$) cycloalkyl, C(O)OH, C(O)O(C$_1$-C$_4$) alkyl, NH$_2$, NH(C$_1$-C$_4$) alkyl, N[(C$_1$-C$_4$) alkyl]$_2$, O(C$_1$-C$_4$) alkyl, OCH$_2$F, OCHF$_2$, OCF$_3$, S(C$_1$-C$_4$) alkyl, S(O)(C$_1$-C$_4$) alkyl, S(O)$_2$(C$_1$-C$_4$) alkyl, S(O)$_2$NH$_2$, S(O)$_2$NH(C$_1$-C$_4$) alkyl, S(O)$_2$N[(C$_1$-C$_4$) alkyl]$_2$, S(O)$_2$(C$_3$-C$_4$) cycloalkyl, (C$_3$-C$_6$) cycloalkyl, and (C$_3$-C$_5$) cycloalkoxy;

wherein the 5- to 10-membered heteroaryl is substituted by 1, 2, 3, or 4 substituents independently selected from the group consisting of halogen, CN, (C$_1$-C$_4$) alkyl, CF$_3$, C(O)NH$_2$, C(O)NH(C$_1$-C$_4$) alkyl, C(O)N[(C$_1$-C$_4$) alkyl]$_2$, C(O)NH(C$_3$-C$_5$) cycloalkyl, C(O)OH, C(O)O (C$_1$-C$_4$) alkyl, NH$_2$, NH(C$_1$-C$_4$) alkyl, N[(C$_1$-C$_4$) alkyl]$_2$, O(C$_1$-C$_4$) alkyl, OCHF$_2$, OCF$_3$, OCH$_2$CF$_3$, S(C$_1$-C$_4$) alkyl, S(O)(C$_1$-C$_4$) alkyl, S(O)$_2$(C$_1$-C$_4$) alkyl, S(O)$_2$NH$_2$, S(O)$_2$NH(C$_1$-C$_4$) alkyl, S(O)$_2$N[(C$_1$-C$_4$) alkyl]$_2$, S(O)$_2$(C$_3$-C$_4$) cycloalkyl, (C$_3$-C$_6$) cycloalkyl, (C$_3$-C$_5$) cycloalkoxy, and phenyl; and wherein each phenyl substituent of the 5- to 10-membered heteroaryl is optionally and independently substituted by 1, 2, 3, 4, or 5 substituents independently selected from the group consisting of F, Cl, CH$_3$, CH$_2$CH$_3$, and OCH$_3$;

(iii) $R^2$ is:

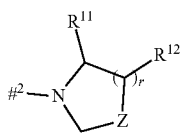

wherein:
r is 0 or 1;
Z is —$CR^{13A}R^{13B}$—, —$NR^{14}$—, —O—, —S—, —S(O)—, or —S(O)$_2$—;
$R^{11}$ is H, CN, (C$_1$-C$_4$) alkyl, C(O)H, or C(O)CH$_3$;
  wherein the (C$_1$-C$_4$) alkyl is optionally substituted by 1, 2, 3, 4, or 5 substituents independently selected from the group consisting of F and OH; and
  wherein the C(O)CH$_3$ is optionally substituted by 1, 2, or 3 substituents independently selected from the group consisting of F and OH;
$R^{12}$ is H, F, or (C$_1$-C$_4$) alkyl;
$R^{13A}$ is H, halogen, CN, (C$_1$-C$_4$) alkyl, CH$_2$F, CHF$_2$, CF$_3$, OH, O(C$_1$-C$_4$) alkyl, OCHF$_2$, OCF$_3$, OCH$_2$CF$_3$, (C$_3$-C$_6$) cycloalkyl, or (C$_3$-C$_5$) cycloalkoxy:
  wherein the (C$_1$-C$_4$) alkyl is optionally substituted by 1, 2, 3, 4, or 5 substituents independently selected from the group consisting of NH$_2$, NH(C$_1$-C$_4$) alkyl, N[(C$_1$-C$_4$) alkyl]$_2$, and OH;
$R^{13B}$ is H, F, or (C$_1$-C$_4$) alkyl,
  wherein the (C$_1$-C$_4$) alkyl is optionally substituted by 1, 2, 3, 4, or 5 F substituents; or
$R^{11}$ and $R^{12}$, together with the carbon atoms to which they are attached, form cyclopropyl or cyclobutyl;
  wherein the cyclopropyl or cyclobutyl is optionally substituted by 1 or 2 F substituents; or
$R^{12}$ and $R^{13A}$, together with the carbon atoms to which they are attached, form cyclopropyl or cyclobutyl;
  wherein the cyclopropyl or cyclobutyl is optionally substituted by 1 or 2 F substituents; or
$R^{13A}$ and $R^{13B}$, together with the carbon atoms to which they are attached, form cyclopropyl or cyclobutyl;
  wherein the cyclopropyl or cyclobutyl is optionally substituted by 1 or 2 F substituents;
$R^{14}$ is H or CH$_3$; and
$^2$ is the point of attachment to —C(O)—; or
(iv) $R^2$ is:

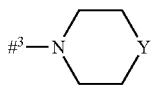

wherein:
Y is —$CR^{16A}R^{16B}$—, —$NR^{15}$—, —O—, or —S—;
$R^{15}$ is H or CH$_3$;
$R^{16A}$ is H or CH$_3$;
$R^{16B}$ is H or CH$_3$; and
$^3$ is the point of attachment to —C(O)—;
$R^3$ is H;
$R^4$ is H or (C$_1$-C$_4$) alkyl;
  wherein the (C$_1$-C$_4$) alkyl is optionally substituted by 1, 2, 3, 4, or 5 substituents independently selected from the group consisting of F, NH(C$_1$-C$_4$) alkyl, N[(C$_1$-C$_4$) alkyl]$_2$, OH, and O(C$_1$-C$_4$) alkyl; and
$R^5$ is H;
with the provisos that:
(1) if $R^{11}$ is H, then at least one of $R^{12}$, $R^{13A}$, or $R^{13B}$ is not H; and
(2) if $R^{11}$ is CN, (C$_1$-C$_4$) alkyl, C(O)H, or C(O)CH$_3$, then $R^{12}$, $R^{13A}$, and $R^{13B}$ are H; and
(B1) reacting the compound of formula (V) above with a compound of the formula (VI):

wherein:
$R^{10}$ is H, (C$_1$-C$_4$) alkyl, (C$_3$-C$_6$) cycloalkyl, or phenyl;
  wherein the (C$_1$-C$_4$) alkyl is optionally substituted by 1, 2, 3, 4, or 5 substituents independently selected from the group consisting of F, CN, OH, O(C$_1$-C$_4$) alkyl, and (C$_3$-C$_6$) cycloalkyl; and
  wherein the (C$_3$-C$_6$) cycloalkyl or phenyl is optionally substituted by 1, 2, or 3 substituents independently selected from the group consisting of halogen, CN, CF$_3$, (C$_1$-C$_4$) alkyl, and O(C$_1$-C$_4$) alkyl;
$X^2$ is Cl, Br, I, OH, OS(O)$_2$CH$_3$, OS(O)$_2$CF$_3$, OS(O)$_2$CF$_2$CF$_2$CF$_2$CF$_3$, OS(O)$_2$-(4-methylphenyl), or OS(O)$_2$-(4-nitrophenyl);
in the presence of a base and optionally an inert solvent, to give the compound of formula (I) above; or
(B2) reacting the compound of formula (V) above with a compound of the formula (VII):

wherein:
$R^6$ is (C$_1$-C$_6$) alkyl, (C$_3$-C$_6$) cycloalkyl, phenyl, or 5- or 6-membered heteroaryl;
  wherein the (C$_1$-C$_6$) alkyl is optionally substituted by 1, 2, 3, 4, or 5 substituents independently selected from the group consisting of F, CN, OH, and O(C$_1$-C$_4$) alkyl; and
  wherein the (C$_3$-C$_6$) cycloalkyl, phenyl, or 5- or 6-membered heteroaryl is optionally substituted by 1, 2, or 3 substituents independently selected from the group consisting of halogen, CN, CF$_3$, (C$_1$-C$_4$) alkyl, and O(C$_1$-C$_4$) alkyl;
in the presence of a base, to give the compound of formula (I) above; or
(B3) reacting the compound of formula (V) above with a compound of the formula (VIII):

wherein:
$R^8$ is (C$_1$-C$_4$) alkyl, (C$_3$-C$_6$) cycloalkyl, phenyl, or 5- or 6-membered heteroaryl;
  wherein the (C$_1$-C$_4$) alkyl is optionally substituted by 1, 2, 3, 4, or 5 substituents independently selected from the group consisting of F, CN, OH, and O(C$_1$-C$_4$) alkyl; and
  wherein the (C$_3$-C$_6$) cycloalkyl, phenyl, or 5- or 6-membered heteroaryl is optionally substituted by 1, 2, or 3 substituents independently selected from the group consisting of halogen, CN, CF$_3$, (C$_1$-C$_4$) alkyl, and O(C$_1$-C$_4$) alkyl; and $X^3$ is Cl, Br, I, OH, $OS(O)_2CH_3$, $OS(O)_2CF_3$, $OS(O)_2CF_2CF_2CF_2CF_3$, $OS(O)_2$-(4-methylphenyl), or $OS(O)_2$-(4-nitrophenyl);

in the presence of a base, to give the compound of formula (I) above; and optionally reacting the compound of formula (I) above with a pharmaceutically acceptable acid or a pharmaceutically acceptable base, optionally in the presence of an inert solvent, to give a pharmaceutically acceptable salt of the compound of formula (I) above.

29. The process according to claim 28, wherein $X^1$ is Cl, Br, I, OH, $OS(O)_2CH_3$, $OS(O)_2CF_3$, $OS(O)_2CF_2CF_2CF_2CF_3$, or $OS(O)_2$-(4-methylphenyl).

30. The process according to claim 28, wherein $X^2$ is Cl, Br, I, OH, $OS(O)_2CH_3$, $OS(O)_2CF_3$, $OS(O)_2CF_2CF_2CF_2CF_3$, or $OS(O)_2$-(4-methylphenyl).

31. The process according to claim 28, wherein $X^3$ is Cl, Br, or OH.

* * * * *